(12) United States Patent
Raff

(10) Patent No.: US 10,918,676 B2
(45) Date of Patent: Feb. 16, 2021

(54) EGG PROTEIN FORMULATIONS AND METHODS OF MANUFACTURE THEREOF

(71) Applicant: Aimmune Therapeutics, Inc., Brisbane, CA (US)

(72) Inventor: Howard V. Raff, Mill Valley, CA (US)

(73) Assignee: Aimmune Therapeutics, Inc., Brisbane, CA (US)

(*) Notice: Subject to any disclaimer, the term of this patent is extended or adjusted under 35 U.S.C. 154(b) by 0 days.

(21) Appl. No.: 16/396,493

(22) Filed: Apr. 26, 2019

(65) Prior Publication Data

US 2019/0247444 A1 Aug. 15, 2019

Related U.S. Application Data

(62) Division of application No. 14/835,336, filed on Aug. 25, 2015.

(60) Provisional application No. 62/041,362, filed on Aug. 25, 2014.

(51) Int. Cl.

| | | |
|---|---|---|
| A61K 35/57 | (2015.01) | |
| A61K 38/55 | (2006.01) | |
| A61K 9/48 | (2006.01) | |
| A61P 37/08 | (2006.01) | |
| A61K 38/17 | (2006.01) | |
| A61K 38/38 | (2006.01) | |
| A61K 38/47 | (2006.01) | |

(52) U.S. Cl.
CPC ............ *A61K 35/57* (2013.01); *A61K 9/4866* (2013.01); *A61K 38/1735* (2013.01); *A61K 38/38* (2013.01); *A61K 38/47* (2013.01); *A61K 38/55* (2013.01); *A61P 37/08* (2018.01); *C12Y 302/01017* (2013.01)

(58) Field of Classification Search
CPC .................................. A61K 36/57; A61K 35/57
USPC ......................................................... 424/581
See application file for complete search history.

(56) References Cited

U.S. PATENT DOCUMENTS

| | | | |
|---|---|---|---|
| 4,112,074 | A | 9/1978 | Truffier |
| 4,340,591 | A | 7/1982 | Lucotte |
| 9,198,869 | B2 | 12/2015 | Walser |
| 9,492,535 | B2 | 11/2016 | Walser |
| 10,086,068 | B2 | 10/2018 | Walser |
| 2004/0068018 | A1 | 4/2004 | Lee |
| 2014/0271721 | A1 | 9/2014 | Walser |
| 2014/0271836 | A1 | 9/2014 | Walser |
| 2016/0030289 | A1 | 2/2016 | Walser |
| 2016/0051593 | A1 | 2/2016 | Raff |
| 2017/0021012 | A1 | 1/2017 | Walser |
| 2018/0042816 | A1 | 2/2018 | Walser |
| 2018/0200361 | A1 | 7/2018 | Simon |
| 2019/0167785 | A1 | 6/2019 | Dilly |

FOREIGN PATENT DOCUMENTS

| | | |
|---|---|---|
| CN | 102715542 A | 10/2012 |
| CN | 103734478 A | 4/2014 |
| EP | 1340493 A1 | 9/2003 |
| JP | 2006514540 A | 5/2006 |
| JP | 2010535232 A | 11/2010 |
| JP | 2012525427 A | 10/2012 |
| JP | 2013523177 A | 6/2013 |
| JP | 2013544239 A | 12/2013 |
| JP | 2014097989 A | 5/2014 |
| JP | 2014139231 A | 7/2014 |
| WO | WO02072069 A1 | 9/2002 |
| WO | WO2004014155 A2 | 2/2004 |
| WO | WO2004014155 A3 | 4/2004 |
| WO | WO2005000243 A2 | 1/2005 |
| WO | WO2005000243 A3 | 4/2005 |
| WO | WO2009018233 A1 | 2/2009 |
| WO | WO2010127125 A1 | 11/2010 |
| WO | WO2011067667 A2 | 6/2011 |
| WO | WO2011130195 A1 | 10/2011 |
| WO | WO2011067667 A3 | 1/2012 |
| WO | WO2012061061 A1 | 5/2012 |
| WO | WO2012123759 A1 | 9/2012 |
| WO | WO2014159607 A1 | 10/2014 |
| WO | WO2014159609 A1 | 10/2014 |

OTHER PUBLICATIONS

Mine et al. The allergenicity of ovomucoid and the effect of its elimination from hen's egg white (Journal of the Science of Food and Agriculture, 81: 1540-1546, 2001). (Year: 2001).*
Abeyrathne, E.D.N.S. et al. (Mar. 28, 2014). "Sequential Separation of Lysozyme, Ovomucin, Ovotransferrin, and Ovalbumin From Egg White," Poultry Science Association, Inc. 93(4):1001-1009.
Bartnikas, L.M. et al. (2013). "Ovomucoid is Not Superior to Egg White Testing in Predicting Tolerance to Baked Egg," J. Allergy Clin. Immunol. Pract. 1(4):354-360, 15 pages.
Bernhisel-Broadbent, J. et al. (1994). "Allergenicity and Antigenicity of Chicken Egg Ovomucoid (Gal d III) Compared With Ovalbumin (Gal d I) in Children With Egg Allergy and in Mice," J. Allergy Clin. Immunol. 93(6):1047-1059.
Blom, W.M. et al. (2013, e-pub. Nov. 27, 2012). "Threshold Dose Distributions for 5 Major Allergenic Foods in Children," J. Allergy Clin. Immunol. 131(1):172-179.
Buchannan, A.D. et al. (2007). "Egg Oral Immunotherapy in Nonanaphylactic Children With Egg Allergy," J. Allergy Clin. Immunol. 119(1):199-207.
Burks, W.A, et al. (Jul. 19, 2012). "Oral Immunotherapy for Treatment of Egg Allergy in Children," N. Engl. J. Med. 367(3):233-243.

(Continued)

*Primary Examiner* — Michael Barker
*Assistant Examiner* — Deborah A Davis
(74) *Attorney, Agent, or Firm* — Morrison & Foerster, LLP

(57) ABSTRACT

The present technology relates generally to formulations comprising egg white protein, methods of manufacturing egg protein formulations and uses for egg protein formulations. In particular, several embodiments are directed to egg protein formulations for oral administration in immunotherapy of subjects affected by egg allergies.

21 Claims, 25 Drawing Sheets

(56) References Cited

OTHER PUBLICATIONS

Cminiti, L. et al. (Jul. Aug. 2015, e-pub. Feb. 25, 2015). "Oral Immunotherapy for Egg Allergy: A Double-Blind Placebo-Controlled Study, With Postdesensitization Follow-Up," J. Allergy Clin. Immunol. Pract. 3(4):532-539.

Caubet, J.C. et al. (Apr. 1, 2011). "Current Understanding of Egg Allergy," Pediatr. Clin. North Am. 58(2):427-443, 19 pages.

Clark, A. et al. (2011). "A Longitudinal Study of Resolution of Allergy to Well-Cooked and Uncooked Egg," Clin. Exp. Allergy 41(5):706-712.

Colás, C. et al. (2012). "Nonhistaminergic Idiopathic Angioedema: Clinical Response to Icatibant," J. Investig Allergol. Clin. Immunol, 22(7):520-521.

Cooke, S.K. et al. (Aug. 15, 1997). "Allergenic Properties of Ovomucoid in Man," J. Immunol. 159(4):2026-2032.

Eller, E. et al. (May 2012). "Clinical thresholds to Egg, Hazelnut, Milk and Peanut: Results From a Single-Center Study Using Standardized Challenges," Ann. Allergy Asthma Immunol. 108(5):332-336.

Encalada, M.E.L. et al. "Ovo-Des Nm®, A Future Treatment for Egg Allergy," Abstract 324, J. Allergy Clin Immunol. (Feb. 2013), 1 page.

Escudero, C. et al. (Jan. 15, 2013). "Dehydrated Egg White: An Allergen Source for Improving Efficacy and Safety in the Diagnosis and Treatment for Egg Allergy," Pediatr. Allergy Immunol. 24:263-269.

Escudero, C.L. et al. (Dec. 2015, e-pub. Aug. 3, 2015). "Early Sustained Unresponsiveness After Short-Course Egg Oral Immunotherapy: A Randomized Controlled Study in Egg-Allergic Children," Clin. Exp. Allergy. 45(12):1833-1843.

Everberg, H. et al. (2011, e-pub. Jul. 24, 2010). "Affinity Purification of Egg-White Allergens for Improved Component-Resolved Diagnostics," International Archives of Allergy and Immunology 154(1):33-41.

Fleischer, D.M. et al. (Jul. 2012). "Allergic Reactions to Foods in Preschool-Aged Children in a Prospective Observational Food Allergy Study," Pediatrics 130(1):e25-32.

Garcia. M.R. et al. (2012). "Commercial Dehydrated Egg White for Special Oral Tolerance Induction (SOTI): An Easier Treatment for Egg Allergy," Journal of Investigational Allergology & Clinical Immunology 22(7):529-531.

Ibáñez, M.D. et al. (2015). "Comprehensive Review of Current Knowledge on Egg Oral Immunotherapy," J. Investig. Allergol. Clin. Immunol. 25(5):316 328.

Itoh, N. et al. (2010). "Rush Specific Oral Tolerance Induction in School-Age Children With Severe Egg Allergy: One Year Follow Up," Allergol. Int. 59(1):43-51.

Jacobsen, B. et al. (Nov. 2, 2008). The Panel of Egg Allergens, Gal d 1-Gal d 5: Their Improved Purification and Characterization, Mol. Nutr. Food Res. 52(Suppl. 2):S176-S185.

Jones, S.M. et al. (2014). "State of the Art on Food Allergen Immunotherapy: Oral, Sublingual, and Epicutaneous," J. Allergy Clin. Immunol. 133(2):318-323.

Joo, K. et al. (2006). "Assessment of Allergenic Activity of a Heat-Coagulated Ovalbumin After In Vivo Digestion," Biosci. Biotechnol. Biochem. 70(3):591-597.

Järvinen, K.M. et al. (Jul. 2007). "Specificity of IgE antibodies to Sequential Epitopes of Hen's Egg Ovomucoid as a Marker for Persistence of Egg Allergy," Allergy 62(7):758-765.

Keet, C.A. et. al. (Feb. 2012). "The Safety and Efficacy of Sublingual and Oral Immunotherapy for Milk Allergy," J. Allergy Clin Immunol. 129(2):448-455, 22 pages.

Krieg, A.M. et al. (Apr. 6, 1995). "CpG Motifs in Bacterial DNA Trigger Direct B-Cell Activation," Nature 374:546-549.

Kulis, M. et al. (Jun. 15, 2013, e-pub. Oct. 22, 2012). "Oral Immunotherapy for Food Allergy: Clinical and Preclinical Studies," Adv. Drug Deily. Rev. 65(6):774-781.

Lemon-Mulé, H. et al. (2008, e-pub. Oct. 13, 2008). "Immunologic Changes in Children With Egg Allergy Ingesting Extensively Heated Egg," J. Allergy Clin. Immunol. 122(5):977-983.

Leonard, S.A. et al. (Jan.-Feb. 2015). "Baked Milk- and Egg-Containing Diet in the Management of Milk and Egg Allergy," J. Allergy Clin. Immunol. Pract. 3(1):13-23.

Lieberman, J.A. et al. (2012). "Outcomes of 100 Consecutive Open, Baked-Egg Oral Food Challenges in the Allergy Office," J. Allergy Clin. Immunol. 129(6):1682-1684.

Mine, Y. et al. (2008, e-pub. Jun. 11, 2008). "Recent Advances in the Understanding of Egg Allergens: Basic, Industrial, and Clinical Perspectives," J. Agric. Food Chem. 56:4874-4900.

Osborne, N.J. et al. (2011). "Prevalence of Challenge Proven IgE Mediated Food Allergy Using Population Based Sampling and Predetermined Challenge Criteria in Infants," J. Allergy Clin. Immunol. 127(3):668-676.

Ovo-Des, N.M. Cantabria labs Product Sheet, retrieved from https://nutricionmedica.com/en/portfolio-view/ovodes-nm, last visited Mar. 15, 2018.

Pisetsky, D.S. (Oct. 1996). "Immune Activation by Bacterial DNA: A New Genetic Code," Immunity 5:303-310.

Ruiz-Garcia, G. M. et al. (2012). "Commercial Dehydrated Egg White for Specific Oral Tolerance Induction (SOTI): an Easier Treatment for Egg Allergy," J. Investig. Allergol. Clin. Immunol. 22(7):529-531.

Sampson, H.A. et al. (2012). "Standardizing Double Blind, Placebo Controlled Oral Food Challenges: American Academy of Allergy, Asthma & Immunology European Academy of Allergy and Clinical Immunology Practall Consensus Report," J. Allergy Clin. Immunol. 130(6):1260 1274.

Savage, J.H. et. al. (Dec. 2007). "The Natural History of Egg Allergy," J. Allergy Clin Immunol. 120(6):1413-1417.

Sicherer, S.H. et al. (2014). "The Natural History of Egg Allergy in an Observational Cohort," J.Allergy Clin. Immunol. 133(2):492-499.

Sicherer, S.H. et al. (Feb. 2014, e-pub. Dec. 31, 2013). "Food Allergy: Epidemiology, Pathogenesis, Diagnosis, and Treatment," J. Allergy Clin. Immunol. 133:291-307.

Sicherer, S.H. et al. (May 2010). "Immunologic Features of Infants with Milk or Egg Allergy Enrolled in an Observational Study (CoFAR) of Food Allergy," J. Allergy Clin. Immunol. 125(5):1077-1083, 14 pages.

Skripak, J.M. et. al. (Dec. 2008). "A Randomized, Double-Blind, Placebo-Controlled Study of Milk Oral Immunotherapy for Cow's Milk Allergy," J. Allergy Clin Immunol. 122(6): 1154-1160, 20 pages.

Tan, J.W. et al. (Oct. 2013). "Baked Egg Food Challenges—Clinical Utility of Skin Test to Baked Egg and Ovomucoid in Children With Egg Allergy," Clin. Exp. Allergy 43(10):1189-1195.

Turner, P.J, et al. (Aug. 2013, e-pub. Jun. 16, 2013). Safety of Food Challenges to Extensively Heated Egg in Egg Allergic Children: A Prospective Cohort Study, Pediatr. Allergy Immunol. 24(5):450-455.

Urisu, A, et al. (1997). "Allergenic Activity of Heated and Ovomucoid-Depleted Egg White," J. Allergy Clin. Immunol. 100(2):171-176.

Vazquez-Ortiz, M. et al. (Jan. 2014). "Baseline Specific IgE Levels Are Useful to Predict Safety of Oral Immunotherapy in Egg-Allergic Children," Clin. Exp. Allergy 44(1):130-141.

Vickery, B.P. et al. (Dec. 1, 2011). "Individualized, IgE-Based Dosing of Egg Oral Immunotherapy Is Associated With the Development of Tolerance," Ann. Allergy Asthma Immunol. 105(6):444-450, 13 pages.

Walsh, B.J. et al. (2005). "Detection of Four Distinct Groups of Hen Egg Allergens Binding IgE in the Sera of Children With Egg Allergy," Allergol et Immunopathol. 33(4):183-191.

Yamamoto, S. et al. (1992). "DNA From Bacteria, But Not From Vertebrates, Induces Interferons, Activates Natural Killer Cells and Inhibits Tumor Growth," Microbiol. Immunol. 36(9):983-997.

Zhu, J. et al. (Jun. 2015, e-pub. Mar. 5, 2015). "A Retrospective Analysis of Allergic Reaction Severities and Minimal Eliciting Doses for Peanut, Milk, Egg, and Soy Oral Food Challenges," Food Chem. Toxicol. 80:92-100.

(56) References Cited

OTHER PUBLICATIONS

Zimmermann, S. et al. (1998). "Cutting Edge: CpG Oligodeoxynucleotides Trigger Protective and Curative Th1 Responses in Lethal Murine Leishmaniasis," J. Immunol. 160:3627-3630.
U.S. Appl. No. 16/111,102, Walser et al., filed Aug. 23, 2018.
U.S. Appl. No. 16/289,370, Walser et al., filed Feb. 28, 2019.
U.S. Appl. No. 16/178,502, Dilly et al., filed Feb. 27, 2019.
Sun, C. et al. (2017). "Divergent Proteome Patterns of Egg Albumen From Domestic Chicken, Duck, Goose, Turkey, Quail and Pigeon," Proteomics 17(1700145):1-12.
Ovo-Des NM (Jun. 22, 2014). Nutrición Médica—"Allergies," Retrieved from https://web.archive.org/web/20140622025328/http://nutricionmedia.com/productos/alergias, last visited Jun. 15, 2020, 2 pages, with Machine Transaction.

* cited by examiner

FIG. 2

|  | Target RH (%) | Change In Mass (%) - ref | | |
|---|---|---|---|---|
|  |  | Sorption | Desorption | Hysteresis |
| Cycle 1 | 0.0 | 0.00 | 0.27 |  |
|  | 10.0 | 2.72 | 3.40 | 0.68 |
|  | 20.0 | 4.47 | 5.60 | 1.13 |
|  | 30.0 | 5.71 | 7.69 | 1.98 |
|  | 40.0 | 6.71 | 9.82 | 3.12 |
|  | 50.0 | 8.02 | 12.31 | 4.29 |
|  | 60.0 | 12.49 | 15.58 | 3.10 |
|  | 70.0 | 17.93 | 20.44 | 2.50 |
|  | 80.0 | 25.34 | 28.63 | 3.29 |
|  | 90.0 | 36.89 | 36.89 |  |
| Cycle 2 | 0.0 | 0.27 | 0.26 |  |
|  | 10.0 | 2.93 | 3.39 | 0.47 |
|  | 20.0 | 4.98 | 5.59 | 0.61 |
|  | 30.0 | 6.83 | 7.56 | 0.73 |
|  | 40.0 | 8.81 | 9.64 | 0.84 |
|  | 50.0 | 11.20 | 12.13 | 0.93 |
|  | 60.0 | 14.34 | 15.39 | 1.05 |
|  | 70.0 | 18.84 | 20.22 | 1.38 |
|  | 80.0 | 25.73 | 28.39 | 2.66 |
|  | 90.0 | 36.80 | 36.80 |  |

Table 6: Microtiter Dilutions

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    | Blank |
| B |   |   |   |   |   |   |   |   |   |    |    | Blank |
| C |   |   |   |   |   |   |   |   |   |    |    | Blank |
| D |   |   |   |   |   |   |   |   |   |    |    | Blank |
| E |   |   |   |   |   |   |   |   |   |    |    | Blank |
| F |   |   |   |   |   |   |   |   |   |    |    | Blank |
| G |   |   |   |   |   |   |   |   |   |    |    | Blank |
| H |   |   |   |   |   |   |   |   |   |    |    | Blank |

Diluted Primary Antibody in PBS at 3 fold dilutions starting at 1:250.

Diluted Coating Antigen at 3 fold dilutions starting at 0.125 mg/mL for Ovomucoid protein, 0.100 mg/mL for Lysozyme and OvAlbumin proteins and 0.5 mg/mL for egg white protein. (OvAlbumin in NaHCO3, pH 9.5, Lysozyme and Ovomucoid in PBS).

*FIGURE 25*

EGG PROTEIN FORMULATIONS AND METHODS OF MANUFACTURE THEREOF

CROSS-REFERENCE TO RELATED APPLICATIONS

This application is a divisional of U.S. application Ser. No. 14/835,336, filed Aug. 25, 2015; which claims priority to U.S. Provisional Patent Application No. 62/041,362, filed Aug. 25, 2014, the disclosure of each of which is herein incorporated by reference in its entirety.

TECHNICAL FIELD

The present technology relates generally to formulations comprising egg protein, methods of manufacturing egg protein formulations and uses for dried egg protein formulations. In particular, several embodiments are directed to egg protein formulations for oral administration in immunotherapy of subjects affected by allergies.

BACKGROUND

Food allergies, or the body's immunological reaction to allergenic epitopes from proteins in the food, can severely impact the quality of life for both adults and children. Egg, milk, and peanut are the greatest sources of allergic response in affected individuals, and can account for approximately 80% of all food allergy cases. The severity of allergic reactions can vary between individuals and can range from between mild irritation to anaphylaxis, which can be so severe as to be life threatening, and egg allergy has an approximate prevalence of 2.6% by age 2.5 years. The current therapy for egg allergy is to place the child on an egg-free diet until the allergy is outgrown (approximately 30% of children), or to maintain the person on an egg-free diet indefinitely. However, because egg is prevalent in processed foods and vaccines, compliance can be difficult and creates a constant challenge for egg-allergic individuals and their caregivers.

Allergic reactions result when a subject's immune system responds to a foreign substance (e.g., allergen). Typically, there is no allergic reaction the first time a subject is exposed to a particular allergen. However, it is the initial response to an allergen that primes the system for subsequent allergic reactions. In particular, the allergen is taken up by antigen presenting cells (APCs; e.g., macrophages and dendritic cells) that degrade the allergen and then display allergen fragments to T-cells. T-cells, in particular CD4+ "helper" T-cells, respond by secreting a collection of cytokines that have effects on other immune system cells. The profile of cytokines secreted by responding CD4+ T-cells determines whether subsequent exposures to the allergen will induce allergic reactions. Two classes of CD4+ T-cells (Th1 and Th2; T-lymphocyte helper type) influence the type of immune response that is mounted against an allergen.

The Th1-type immune response involves the stimulation of cellular immunity to allergens and infectious agents and is characterized by the secretion of IL-2, IL-6, IL-12, IFN-gamma, and TNF-beta by CD4+ T helper cells and the production of IgG antibodies. Exposure of CD4+ T-cells to allergens can also activate the cells to develop into Th2 cells, which secrete IL-4, IL-5, IL-10, and IL-13. IL-4 production stimulates maturation of B cells that produce IgE antibodies specific for the allergen. These allergen-specific IgE antibodies attach to mast cell and basophil receptors, where they initiate a rapid immune response to the next exposure to allergen. When the subject encounters the allergen a second time, the allergen is quickly bound by these surface-associated. IgE molecules, resulting in the release of histamines and other substances that trigger allergic reactions. Subjects with high levels of IgE antibodies are known to be particularly prone to allergies.

SUMMARY

Provided herein are egg protein formulations for use in the treatment of egg allergy. Also provided herein is a method for identifying and manufacturing egg protein formulations.

The egg protein formulations provided herein may comprise (a) egg white protein, (b) one or more of a diluent, lubricant, or filling agent, and (c) a capsule shell or pouch. Optionally, the formulations may comprise one or more glidants.

In some embodiments, the egg protein formulations have characterized levels of ovomucoid protein, ovalbumin protein, and lysozyme protein.

In other embodiments, the egg protein formulations are stable over a period of 3, 6, 9, 11, 12, 18, 24, or 36 months. In other embodiments, the egg protein formulations have improved shelf life and flow compared to pure egg white powder.

In some embodiments, the egg protein formulation comprises about 0.1% to 50% (w/w) egg white protein; about 40% to 90% (w/w) of one or more diluents; about 1% to 30% (w/w) of one or more filling agents; about 0.01% to 10% (w/w) of one or more lubricants; and a capsule shell or pouch.

In some embodiments, the egg protein formulation comprises about 0.1% to 21% (w/w) egg protein.

In some embodiments, the egg protein formulation comprises about 0.2 mg to about 1000 mg egg protein per capsule or pouch; In other embodiments, the egg protein formulation comprises about 0.2 mg egg white protein; In other embodiments, the egg protein formulation comprises about 1.0 mg egg white protein; In other embodiments, the egg protein formulation comprises about 10.0 mg egg white protein; In other embodiments, the egg protein formulation comprises about 20.0 mg egg white protein; In other embodiments, the egg protein formulation comprises about 100.0 mg egg white protein. In other embodiments, the egg protein formulation comprises about 200.0 mg egg white protein. In other embodiments, the egg protein formulation comprises about 1000.0 mg egg white protein.

In some embodiments, an egg protein formulation for the treatment of egg allergy in a subject may be identified by a) determining the concentrations of ovomucoid, ovalbumin, and/or lysozyme proteins in a composition of egg white protein by one or more analytical methods; b) comparing the concentrations of the proteins to the concentrations of a reference standard; and; c) identifying a composition for treatment of egg allergy in a subject, wherein the same contains at least the concentrations of ovomucoid, ovalbumin, and lysozyme protein as the reference standard;

In other embodiments, one analytical method used to determine the concentrations of ovomucoid, ovalbumin, and lysozyme proteins in a composition of egg white protein is size exclusion chromatography.

In some embodiments, a low dose egg protein formulation may be manufactured by: a) mixing an amount of egg white protein comprising characterized ovomucoid, ovalbumin, and lysozyme proteins and a diluent in a first blend; b) adding between 50-99% diluent in a second blend; c) adding a diluent, filling agent and/or lubricant in a final blend; and
d) encapsulating blended protein in a capsule or sachet.

In some embodiments, the levels of ovomucoid, ovalbumin, and lysozyme protein are stable for 3, 6, 9, 11, 12, 18, 24, or 36 or more months.

In some embodiments, the egg protein formulation comprises a diluent selected from the group consisting of alginic acid and salts thereof; cellulose derivatives; silicified microcrystalline cellulose; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tmgacanth, dextrin, a sugar; dicalcium phosphate; a natural or synthetic gum; polyvinylpyrrolidone, larch arabogalactan, Veegum®, polyethylene glycol, waxes, sodium alginate, a starch; a cross-linked starch; a cross-linked polymer; a cross-linked polyvinylpyrrolidone; alginate; a clay; a gum; sodium starch glycolate; bentonite; a natural sponge; a surfactant; a resin; citrus pulp; sodium lauryl sulfate; and sodium lauryl sulfate in combination starch.

In some embodiments, the egg protein formulation comprises a filling agent selected from the group consisting of lactose, calcium carbonate, calcium phosphate, dibasic calcium phosphate, calcium sulfate, microciystalline cellulose, cellulose powder, dextrose, dextrates, dextran, starches, pregelatinized starch, sucrose, xylitol, lactitol, mannitol, sorbitol, sodium chloride, and polyethylene glycol.

In some embodiments, the egg protein formulation comprises a lubricant selected from the group consisting of stearic acid, calcium hydroxide, talc, corn starch, sodium stearyl fumeratc, alkali-metal and alkaline earth metal salts, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol, propylene glycol, sodium oleate, glyceryl behenate, glyceryl palmitostearate, glyceryl benzoate, and magnesium or sodium lauryl sulfate.

BRIEF DESCRIPTION OF THE DRAWINGS

FIG. 2 is a table showing a DVS Isotherm analysis of rate of moisture uptake in egg white protein in accordance with aspects of the present technology.

FIG. 25 shows an example of a microtiter plate.

DETAILED DESCRIPTION

I. Overview

Figure 1:
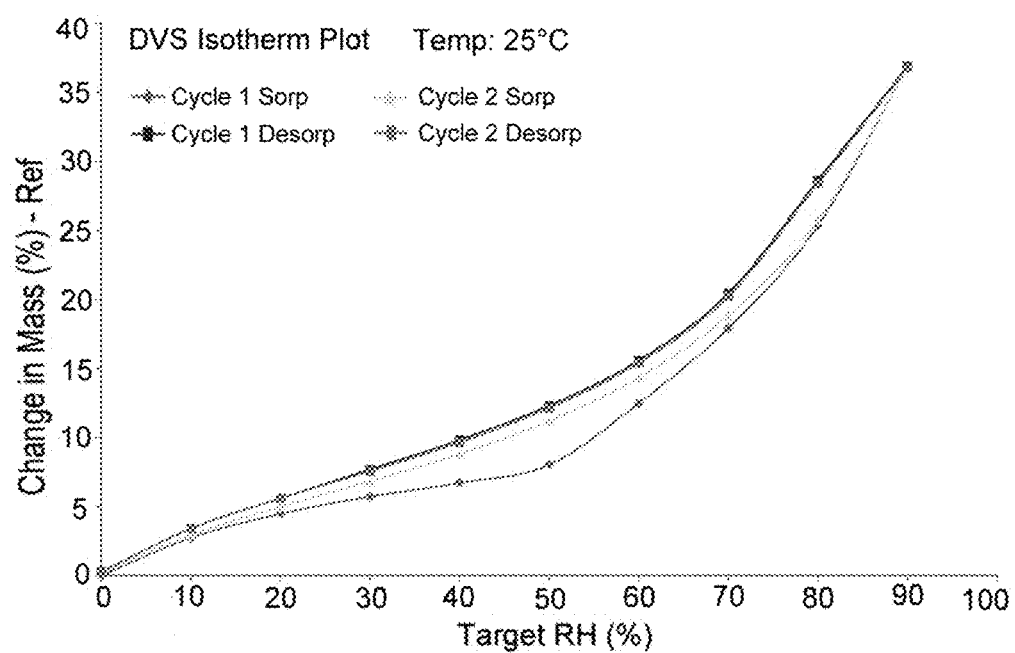
FIG. 1 is a dynamic vapor sorption (DVS) Isotherm Plot showing the rate of change in mass of a sample (rate of moisture uptake) in accordance with aspects of the present technology. Organic and water sorption isotherms are measured for egg white powder.

Food allergies are caused, in most cases, by a reaction to proteins in the food. In the early years of life the immune system is still developing and may fail to develop tolerance to dietary antigens (this may also be described as insufficient induction of oral tolerance). The result is that the baby or child or young animal mounts an exaggerated immune response to the dietary protein and develops an allergic response to it. The most common food allergies in children are milk, eggs, peanuts, and tree nuts. Currently there are no effective treatments available for food allergy. Avoiding the offending allergen has been the only accepted strategy to manage food allergy. However, strict avoidance diets can be complicated due to difficulty in interpreting labels and by the presence of undeclared or hidden allergens in commercially prepared foods.

Symptoms experienced by subjects with allergy to egg proteins can be physiologically diverse as well as have varying severity. For example, symptoms may involve skin (atopic dermatitis, hives/angioedema, rashes), gastrointestinal tract (growth failure, severe gastro-esophageal reflux, chronic diarrhea, persistent constipation, malabsorption syndromes, recurrent vomiting, enterocolitis, anoproctite) or potentially life-threatening anaphylactic reactions (glottis edema, hypotension up to shock, tight asthma, acute skin and gastrointestinal symptoms). In most cases histopathological lesions of the intestinal mucosa are found that are very similar to the typical ones of celiac disease (intestinal villous atrophy of various degrees), anatomo-pathologic index of the malabsorption condition. The intensity and the number of symptoms is variable over time, not only from subject to subject, but also in the individual patient.

Because individuals severely allergic to eggs can have life-threatening reactions after consuming small amounts of egg proteins, their quality of life can be severely impacted by their allergy. Despite the need for treatments, clinical development of oral immunotherapy for food allergy has proceeded slowly and no FDA-approved oral immunotherapy treatments currently exist. The use of food/processed food products in immunotherapy is not ideal as the allergen, levels present in foods may be inconsistent; may degrade over time and under certain conditions; and in the case of powdered food products, may clump or adhere to capsules or other packaging. Because tiny amounts of food allergens can cause severe allergic reaction, fluctuations in active ingredient for any of these reasons could render the oral immunotherapy treatment unpredictable.

Chemical stability is a critical aspect in the design and manufacture, as well as regulatory review and approval, of pharmaceutical compositions. The rate of decomposition of these compositions may be affected by numerous environmental factors, including temperature, light, radiation, enzyme or other catalysts, pH and ionic strength of the solution, solvent type, and buffer species. Such degradation may decrease efficacy and shorten effective shelf life.

The egg protein formulations provided herein may provide for increased shelf life and stability and may lessen the risks associated with oral immunotherapy treatment of egg allergy by providing for consistent dosing of egg allergens. Consistent dosing is achieved both through the detailed characterization of the protein levels present in the egg protein formulations (and selection of lots meeting defined criteria), and through the improvement in stability of the egg allergens present in such compositions.

Specific immunotherapy for food allergy, including egg allergy, in the forms of oral immunotherapy (OIT) and sublingual immunotherapy (SLIT) has been studied in recent years and has demonstrated encouraging safety and efficacy results in early clinical trials, including beneficial immunologic changes. OIT has shown evidence for inducing desensitization in most subjects with immunologic changes over time indicating progression toward clinical tolerance (Skripak et. al., J. Allergy Clin Immunol. 122(6): 1154-1160, 2008; Keet et. al., J. Allergy Clin Immunol. 129(2): 448-455, 2012).

Various aspects of the present technology provide formulations comprising egg white protein protein that may be formulated into a pharmaceutical composition. These presently disclosed formulations, when administered to a patient according, to a treatment regimen, can provide oral immunotherapy (OIT) for subjects that are allergic to eggs and egg products. Following treatment, subjects administered an oral food challenge (OFC) may be partially or fully desensitized to egg protein in accordance with aspects of the present technology.

Provided herein are compositions (i.e., formulations) and methods for oral immunotherapy of egg and egg protein products in accordance with aspects of the present technology.

Various aspects of the present technology provide egg protein protein formulations, methods of manufacturing egg protein protein formulations and uses thereof. In some embodiments, an egg protein composition can comprise one or more glidants, one or more lubricants, and one or more diluents and/or filling agents. For example, in other embodiments, an egg protein composition can comprise one or more glidants, one or more lubricants, and one or more diluents and one or more filling agents.

Specific details of several embodiments of the technology are described below in the Detailed Description and the Examples. Although many of the embodiments are described below with respect to compositions (i.e., formulations) for oral immunotherapy and/or for use in clinical trials for oral immunotherapy of egg protein, other applications and other embodiments in addition to those described herein are within the scope of the technology. Additionally, several other embodiments of the technology can have different components or procedures than those described herein. A person of ordinary skill in the art, therefore, will accordingly understand that the technology can have other embodiments with additional components, or the technology can have other embodiments without several of the aspects shown and described below.

All references, including publications, patent applications, and patents, cited herein are hereby incorporated by reference to the same extent as if each reference were individually and specifically indicated to be incorporated by reference and were set forth in its entirety herein.

II. Definitions

Unless defined otherwise, all technical and scientific terms used herein have the same meaning as is commonly understood by one of skill in the art to which the present technology described herein belong. All patents and publications referred to herein are incorporated by reference.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the particular subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it there individually recited herein.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. In other embodiments, the use of the term "about" indicates values slightly outside the cited values, i.e., plus or minus 0.1% to 5%, which are also effective and safe. In other embodiments, the use of the term "about" indicates values slightly outside the cited values, i.e., plus or minus 0.1% to 2%, which are also effective and safe.

It is to be understood that any ranges, ratios and ranges of ratios that can be formed by, or use of the terms "a" and "an" and "the" and similar referents in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the technology or the claims. No language in the specification should be construed as indicating any non-claimed element as essential to the present technology.

The term "absorption" typically refers to the process of movement of egg allergen(s) from the gastrointestinal tract into a blood vessel.

The term "animal", as used herein, refers to humans as well as non-human animals, including, for example, mammals, birds, reptiles, amphibians, and fish. In some embodiments, the non-human animal is a mammal (e.g., a rodent, a mouse, a rat, a rabbit, a monkey, a dog, a cat, a primate, or a pig). An animal may be a transgenic animal.

The term "antigen", as used herein, refers to a molecule that elicits production of an antibody response (i.e., a humoral response) and/or an antigen-specific reaction with T-cells (i.e., a cellular response) in an animal.

The term "allergen", as used herein, refers to a subset of antigens which elicit the production of IgE in addition to other isotypes of antibodies. The terms "allergen", "natural allergen", and "wild-type allergen" may be used interchangeably. Some examples of allergens for the purpose of the present technology are protein allergens.

The phrase "allergic reaction", as used herein, relates to an immune response that is IgE mediated with clinical symptoms primarily involving the cutaneous (e.g., uticana, angiodema, pruritus), respiratory (e.g., wheezing, coughing, laryngeal edema, rhinorrhea, watery/itching eyes), gastrointestinal (e.g., vomiting, abdominal pain, diarrhea), and cardiovascular (i.e., if a systemic reaction occurs) systems. For the purposes of the present technology, an asthmatic reaction is considered to be a form of allergic reaction.

The phrase "anaphylactic allergen", as used herein, refers to a subset of allergens that are recognized to present a risk of anaphylactic reaction in allergic individuals when encountered in its natural state, under natural conditions. For example, as described herein pollen allergens, mite allergens, allergens in animal danders or excretions (e.g., saliva, urine), and fungi allergens are not considered to be anaphylactic allergens. On the other hand, food allergens, insect allergens, and rubber allergens (e.g., from latex) are generally considered to be anaphylactic allergens. Food allergens, in particular, are anaphylactic allergens for use in the practice of the present technology. In particular, nut allergens (e.g., from egg, walnut, almond, pecan, cashew, hazelnut, pistachio, pine nut, brazil nut), dairy allergens (e.g., from egg, milk), seed allergens (e.g., from sesame, poppy, mustard), soybean, wheat, and fish allergens (e.g., from shrimp, crab, lobster, clams, mussels; oysters, scallops, crayfish) are anaphylactic food allergens according to the present technology. Particularly interesting anaphylactic allergens are those to which reactions are commonly so severe as to create a risk of death.

The phrase "anaphylaxis" or "anaphylactic reaction", as used herein, refers to a subset of allergic reactions characterized by mast cell degranulation secondary to cross-linking of the high-affinity IgE receptor on mast cells and basophils induced by an anaphylactic allergen with subsequent mediator release and the production of severe systemic pathological responses in target organs, e.g., airway, skin, digestive tract, and cardiovascular system. As is known in the art, the severity of an anaphylactic reaction may be monitored, for example, by assaying cutaneous reactions, puffiness around the eyes and mouth, vomiting, and/or diarrhea, followed by respiratory reactions such as wheezing and labored respiration. The most severe anaphylactic reactions can result in loss of consciousness and/or death.

The phrase "antigen presenting cell" or "APC", as used herein, refers to cells which process and present antigens to T-cells to elicit an antigen-specific response, e.g., macrophages and dendritic cells.

When two entities are "associated with" one another as described herein, they are linked by a direct or indirect covalent or non-covalent interaction. Preferably, the association is covalent. Desirable non-covalent interactions include, for example, hydrogen bonding, van der Walls interactions, hydrophobic interactions, magnetic interactions, etc.

"Bioavailability" refers to the percentage of the weight of egg allergen(s) dosed that is delivered into the general circulation of the animal or human being studied. The total exposure (AUC(0-∞)) of a drug when administered intravenously is usually defined as 100% Bioavailable (F %). "Oral bioavailability" refers to the extent to which egg allergen(s) are absorbed into the general circulation when the pharmaceutical composition is taken orally as compared to intravenous injection.

"Blood plasma concentration" refers to the concentration of an egg allergen(s) in the plasma component of blood of a subject. It is understood that the plasma concentration of egg allergen(s) may vary significantly between subjects, due to variability with respect to metabolism and/or possible interactions with other therapeutic agents. In accordance with one aspect of the present technology, the blood plasma concentration of egg allergen(s) may vary from subject to subject. Likewise, values such as maximum plasma concentration (Cmax) or time to reach maximum plasma concentration (Tmax), or total area under the plasma concentration time curve (AUC(0-∞)) may vary from subject to subject. Due to this variability, the amount necessary to constitute "a therapeutically effective amount" of egg allergen(s) may vary from subject to subject.

"Carrier materials" include any commonly used excipients in pharmaceutics and should be selected on the basis of compatibility with egg allergen(s) and the release profile properties of the desired dosage form. Particular examples of carrier materials can include binders, suspending agents, disintegration agents, filling agents, surfactants, solubilizers, stabilizers, lubricants, wetting agents, diluents, and the like.

"Excipients," as used herein are substances that can facilitate drug delivery, absorption or solubility. Excipients can include diluents, filling agents, lubricants, and glidants.

"Pharmaceutically compatible carrier materials" may comprise, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

As used herein, the terms "comprising," "including," and "such as" are used in their open, non-limiting sense.

The phrase "decreased anaphylactic reaction", as used herein, relates to a decrease in clinical symptoms following treatment of symptoms associated with exposure to an, anaphylactic allergen, which can involve exposure via cutaneous, respiratory, gastrointestinal, and mucosal (e.g., ocular, nasal, and aural) surfaces or a subcutaneous injection (e.g., via a bee sting).

"Desensitization" or "desensitize" refers to the ability of a patient to consume small to large amounts of the allergic food source without demonstrating an allergic reaction. Desensitization differs from "tolerance" in that it requires chronic treatment with the food source to maintain the "allergic-free" state. Whereas in the "tolerance" state, treatment is no longer required.

"Diluents" are inert agents typically used for bulking or dilution that do not have pharmacologic activity. Diluents can be added to a small mass. Diluents for use in the formulations provided herein include, but are not limited to, alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), microcrystalline cellulose (e.g., Avicel®); silicified microcrystalline cellulose (e.g., Prosolv SMCC 50®, Prosolv HD 90®); microcrystalline dextrose; amylase; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, sorbitol, xylitol (e.g., Xylitab®), lactose (e.g., lactose monohydrate, lactose anhydrous, etc.); dicalcium phosphate; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, a starch, e.g., a natural starch such as corn starch or potato starch, a pregelatinized starch such as Colorcon (Starch 1500), National 1551 or Amijel®, or sodium starch glycolate such as Promogel® or Explotab®; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and combinations thereof. In some embodiments, the formulation comprises microcrystalline cellulose or starch 1500. In other embodiments, the formulation comprises microcrystalline cellulose and starch 1500.

The term "epitope", as used herein, refers to a binding site including an amino acid motif of between approximately six and fifteen amino acids which can be bound by an immunoglobulin (e.g., IgE, IgG, etc.) or recognized by a T-cell receptor when presented by an APC in conjunction with the major histocompatibility complex (MHC). A linear epitope is one where the amino acids are recognized in the context of a simple linear sequence. A conformational epitope is one where the amino acids are recognized in the context of a particular three dimensional structure.

"Filling agents," as used herein refers to bulking agents. For example, inert substances that can be put into a capsule. Filling agents for use in the formulations provided herein include, but are not limited to, compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and combinations thereof.

An allergen "fragment" according to the present technology is any part or portion of the allergen that is smaller than the intact natural allergen. In certain embodiments of the present technology, the allergen is a protein and the fragment is a peptide.

"Glidants" are anti-caking agents and act to enhance the flow of a granular mixture by reducing interparticle friction used in the pharmaceutical production of, for example, capsules. Glidants for use in the formulations provided herein include, but are not limited to, colloidal silicon dioxide (Cab-O-Sil) and talc (e.g., Ultra Talc 4000). In some embodiments, the composition comprises talc.

The phrase "immunodominant epitope", as used herein, refers to an epitope which is bound by antibody in a large percentage of the sensitized population or where the titer of the antibody is high, relative to the percentage or titer of antibody reaction to other epitopes present in the same antigen. In some embodiments, an immunodominant epitope is bound by antibody in more than 50% of the sensitive population and, in further examples more than 60%, 70%, 80%, 90%, 95%, or 99%.

The phrase "immunostimulatory sequences" or "ISS", as used herein, relates to oligodeoxynucleotides of bacterial, viral, or invertebrate origin that are taken-up by APCs and activate them to express certain membrane receptors (e.g., B7-1 and B7-2) and secrete various cytokines (e.g., IL-1, IL-6, IL-12, TNF). These oligodeoxynucleotides contain unmethylated CpG motifs and when injected into animals in conjunction with an antigen, appear to skew the immune response towards a Th1-type response. See, for example, Yamamoto et al., Microbiol. Immunol. 36:983, 1992; Krieg et al., Nature 374:546, 1995; Pisetsky, Immunity 5:303, 1996; and Zimmerman et al., J. Immunol. 160:3627, 1998.

"Isolated" (used interchangeably with "substantially pure") when applied to polypeptides means a polypeptide or a portion thereof, which has been separated from other proteins with which it naturally occurs. Typically, the polypeptide is also substantially (i.e., from at least about 70% to about 99%) separated from substances such as antibodies or gel matrices (polyacrylamide) which are used to purify it.

"Lubricants," as used herein are substances that prevent ingredients from clumping together and from sticking to the wall of a pharmaceutical capsule or other container. Lubricants, allow a capsule to be emptied without undue loss of active ingredients. Lubricants for use in the formulations provided herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and combinations thereof.

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Oral food challenge" refers to a highly accurate diagnostic test for food allergy. During the food challenge, the allergist feeds the patient the suspect food in measured doses, starting with very small amounts that are unlikely to trigger symptoms. Following each dose, the patient is observed for a period of time for any signs of a reaction. If there are no symptoms, the patient gradually receives increasingly larger doses. If any signs of a reaction are evident, the food challenge is stopped and the patient is, characterized as failing the food challenge and is allergic to the food at the sensitivity level determined by the amount of food triggering the allergic response.

"Oral immunotherapy" refers to an orally-administered medical treatment for patients suffering from allergies, involving administering increasing doses of allergens to the patients in order to desensitize or provide tolerance to a patient for that allergen.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds which may be used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide and combinations thereof.

The total egg protein, ovomucoid protein, ovalbumin protein, and/or lysozyme protein in the egg protein formulations provided herein may be considered "stable" if its concentration is ±10% the original concentration of such protein(s) in the egg protein formulation immediately after manufacture.

The compositions described herein can be formulated for administration to a subject via any conventional means including, but not limited to, oral administration routes. As used herein, the term "subject" is used to mean an animal, such as a mammal, including a human or non-human. The formulations are for prevention and treatment of symptoms associated with exposure to limited amounts of egg allergen in children and adults. In some embodiments, a subject is from about 1 to about 35 years of age, including from 4 to about 26 years of age.

A "therapeutically effective amount" or "effective amount" is that amount of egg allergen(s) needed to achieve a pharmacological effect. The term "therapeutically effective amount" includes, for example, a prophylactically effective amount. An "effective amount" of egg allergen(s) is an amount effective to achieve a desired pharmacologic effect or therapeutic improvement without undue adverse side effects. The effective amount of an egg allergen(s) will be selected by those skilled in the art depending on the particular subject and the disease level. It is understood that "an effect amount" or "a therapeutically effective amount" can vary from subject to subject, due to variation in metabolism, age, weight, general condition of the subject, the condition being treated, the severity of the condition being treated, and the judgment of the prescribing physician.

"Tolerance" to an allergen refers to the relatively long-lasting effects of immunotherapy, presumably due to effects on T cell responsiveness, that persist even after the treatment is discontinued (although tolerance may not always be permanent).

"Treat" or "treatment" as used in the context of an allergy-related disorder refers to any treatment of a disorder or disease related to allergy, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

III. Compositions/Formulations

Provided herein are egg formulations and/or egg protein formulations for use in oral immunotherapy. In some embodiments, the formulation comprises egg protein powder, or alternatively, one or more proteins isolated from egg powder, blended with one or more excipients. For example, in addition to egg protein or protein(s) isolated from egg powder, the formulations can comprise one or more of each of diluents, filling agents, glidants, lubricants, colorants, and capsule shell components.

In some embodiments, egg white protein comprises ovomucoid, ovalbumin, and lysozyme proteins. In other embodiments, egg white protein contains as active ingredients: ovomucoid, ovalbumin, and lysozyme proteins.

In some embodiments, an egg protein formulation comprises one or more diluents. In some embodiments, an egg protein formulation comprises one or more glidants. In some embodiments, an egg protein formulation comprises one or more lubricants. In some embodiments, an egg protein formulation comprises one or more filling agents.

In some embodiments, a final egg protein formulation comprises egg white protein (containing characterized egg allergen proteins ovomucoid, ovalbumin and lysozyme) formulated with a diluent, a filling agent, and a lubricant in graduated doses, having total egg white protein doses of 0.2 mg, 1 mg, 10 mg, 20 mg, 100 mg, 200 mg and 1000 mg each of egg white protein. Each capsule or container formulation (e.g., sachet) may be opened and the content mixed into taste-masking food immediately prior to administration.

In other embodiments, a final formulation comprises egg white protein (containing characterized egg allergen proteins ovomucoid, ovalbumin and lysozyme) formulated with a diluent and a filling agent in graduated doses, having total egg white protein doses of 0.2 mg, 1.0 mg, 10 mg, 20 mg, 100 mg, 200 mg, 300 mg, 500 mg, or 1000 mg of egg white protein. Each capsule or container (e.g., pouch) may be opened and the content mixed into taste-masking food immediately prior to administration.

In some embodiments, the formulation comprising egg protein is encapsulated (e.g., 0.2 mg, 1.0 mg, 10 mg, 20 mg, and 100 mg doses). In other embodiments, the formulation comprising egg protein is sachet packaged (e.g., 100 mg, 200 mg, 300 mg, 500 mg, and 1000 mg doses).

The product is intended to deliver increasing concentrations of dry egg powder, yielding egg protein at dosages of 0.2 mg, 1.0 mg, 10.0 mg, 20 mg, 100.0 mg, 200.0 mg, 500.0 mg, and 1000.0 mg. The 0.2 mg through the 100.0 mg dosages may be encapsulated. The 300 mg, 500.0 mg and 1000 mg dosages may be sachet (pouched) packaged. In some embodiments, a sachet can be a multi-layered pouch lined, for example, with a pharmaceutically accepted and/or compatible liner (e.g., foil). In conventional practice, and in some embodiments, the sachet is machine-formed following filling of the material with the desired amount of the pharmaceutical composition. It is desired that the capsule and sachet pack contents, at each dosage strength, empty as cleanly and completely as possible from the capsule shells or sachet pack film as the intent, in some embodiments, is to add the capsule or sachet pack contents, as a powder, to food for consumption by the patient. A placebo will be developed for each of the dosage strengths. Each placebo will be encapsulated or sachet packaged to match its corresponding active dosage.

In yet other embodiments, degradation of egg protein, as measured by size exclusion chromatography, may be used to determine stability. In a further embodiment, an egg protein formulation that does not have significant changes in moisture content, appearance and odor for over three months of storage (e.g., storage at 5° C./60% relative humidity, storage at 25° C./60% relative humidity, storage at 40° C./75% relative humidity) can be determined to be stable. In some embodiments, the levels of egg protein are stable for 3, 6, 9, 11, 12, 18, 24, or 36 or more months. In a further embodiment, the levels of ovomucoid, ovalbumin and lysozyme proteins are stable for 3, 6, 9, 11, 12, 18, 24, or 36 or more months.

Various sources of egg white protein are commercially available. For example, the egg white protein can be Deb El Egg White Protein from Deb El Food. Products, Elizabeth N.J. or EWP from Michael Foods, Minnetonka, Minn. The egg white protein may be further processed under cGMP conditions. In other embodiments, the egg white protein (approximately 85% egg protein w/w) comprises particles, wherein the particles can have diameters in the range of about 10 μm to about 250 μm, including 75 μm and 150 μm.

Under cGMP manufacturing conditions, the egg white protein is formulated with a diluent, a filling agent, a glidant, and/or a lubricant, and is subsequently encapsulated as 0.2, 1, 10, 20, 100, 200, 300, 500 or 1000 mg of egg protein in size 3 or 00 Hydroxypropyl Methyl Cellulose (HPMC) capsules or sachet packaged (for higher doses). In certain embodiments, the concentration of egg protein can be from about 0.05% to about 50% w/w, or any integer therein. In other embodiments, a composition described herein comprises one or more egg proteins in a concentration from about 0.1% to about 25% w/w. In other embodiments, a composition described herein comprises one or more egg proteins in a concentration from about 0.2%, about 1%, about 2%, about 4%, or about 50% w/w. In other embodiments, at higher doses, the sachets comprise one or more egg white proteins in a concentration from about 40% to about 100%, including, but not limited to 50%, 60%, 70%, 80%, 90%, 91%, 92%, 93%, 94%, 95%, 96%, 97%, 98%, and 99%. In other embodiments, a composition described herein comprises one or more egg proteins in a concentration from about 0.1%, about 0.67%, about 2.1%, about 4%, or about 21% w/w of formulation.

In some embodiments, a composition described herein comprises one or more egg proteins in a target unit weight from about 0.2 mg/capsule to about 1000 mg/sachet, or any integer therein. In yet other embodiments, a composition described herein comprises one or more egg proteins in a target unit weight of about 0.2 mg/capsule to about 1 mg/capsule, about 10 mg/capsule, about 100 mg/capsule or pouch, about 300 mg/capsule or pouch, or about 1000 mg/sachet or pouch.

Compositions for use in the methods described herein include, but are not limited to, about 0.2 mg, about 1.0 mg, about 10 mg, about 20 mg, about 100 mg, about 200 mg, about 300 mg, about 500 mg, and/or about 1000 mg doses of total egg protein.

In some embodiments, the final formulation comprising egg white protein is in a dose of 0.2 mg and the concentration of ovomucoid comprises from about 0.032 to about 0.048 mg. In other embodiments, the dose of the composition is 1.0 mg and the concentration of ovomucoid comprises from about 0.16 to about 0.24 mg; In other embodiments, the dose of the composition is 10.0 mg and the concentration of ovomucoid comprises from about 1.6 to about 2.4 mg; or In other embodiments, the dose of the composition is 100.0 mg and the concentration of ovomucoid comprises from about 16 to about 24 mg. In some embodiments, the dose of the composition is 0.2 mg and the concentration of ovalbumin comprises from about 0.092 to about 0.108 mg; In other embodiments, the dose of the composition is 1.0 mg and the concentration of ovalbumin comprises from about 0.46 to about 0.54 mg; In other embodiments, the dose of the composition is 10.0 mg and the concentration of ovalbumin comprises from about 4.6 to about 5.4 mg; or In other embodiments, the dose of the composition is 100.0 mg and the concentration of ovalbumin comprises from about 46 to about 54 mg. In some embodiments, the dose of the composition is 0.2 mg and the concentration of lysozyme comprises from about 0.002 to about 0.018 mg; In other embodiments, the dose of the composition is 1.0 mg and the concentration of lysozyme comprises from about 0.01 to about 0.09 mg; In other embodiments, the dose of the composition is 10.0 mg and the concentration of lysozyme comprises from about 0.1 to about 0.9 mg; or In other embodiments, the dose of the composition is 100.0 mg and the concentration of lysozyme comprises from about 1.0 to about 9.0 mg.

In some embodiments, a composition provided herein is contained within a capsule including, but not limited to a white opaque HPMC capsule shell (e.g., Capsugel) and may further contain, in some instances, a coloring agent (e.g., pigment blends, and/or color). In other embodiments, the capsule can be a clear or opaque HPMC capsule shell or a blue opaque HPMC capsule shell.

In some embodiments, a composition described herein comprises egg protein in a target unit weight from about 0.2 mg/capsule to about 1000 mg/sachet, or any integer therein. In yet other embodiments, a composition described herein comprises egg protein in a target unit weight of about 0.2 mg/capsule to about 1 mg/capsule, about 10 mg/capsule, about 20 mg/capsule, about 100 mg/capsule or sachet, about 200 mg/sachet, about 300 mg/sachet, about 500 mg/sachet, or about 1000 mg/sachet.

The diluent and/or filling agent provides the opportunity to formulate the low and high doses to contain adequate volume for dispersal from the opened capsule. The glidants and lubricant add flowability to the egg white protein such that the capsule can be reproducibly filled by automated encapsulation machines, and to optimize the efficiency by which the capsule is easily emptied of protein by the subject. For clinical trials, the capsules can be bulk packed into high density polyethylene (HDPE) bottles. At the time of use, capsule(s) comprising egg protein can be opened and the content mixed into taste-masking food immediately prior to administration.

The concentration of diluent in an egg protein formulation described herein may be from about 30% to about 99% w/w. In some embodiments, the concentration of diluent may be from about 40% to about 90% w/w of the composition. In some embodiments, the diluent may be silicified microcrystalline cellulose and the concentration may be about 50% to about 90% w/w of the composition. In other embodiments, the diluent may be silicified microcrystalline cellulose and the concentration may be about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, 87, about 88%, about 89%, or about 90% w/w of the composition. In some embodiments, more than one type of silicified microcrystalline cellulose is used to get the desired w/w of the composition.

The concentration of glidant in a composition described herein may be from about 0.01% to about 10% w/w of the composition. In some embodiments, the glidant in a composition described herein may be about 0.01% to about 3.0%. In some embodiments, the glidant is talc and the concentration of glidant in a composition described herein may be about 0.01%, about 0.05%, about 0.1%, about 0.25%, about 0.2%, about 0.75%, about 1.0%, about 1.25%, 1.5% or about 2.5% w/w of the composition.

The target unit weight of the glidant may be from about 0.05 to about 5 mg/capsule. In some embodiments, the glidant is talc and the target unit weight is about 0.725, about 2.625 or about 3.0 mg/capsule. In other embodiments, the glidant is colloidal silicon dioxide (e.g., Cab-O-Sil) and the target unit weight is about 0.5 mg, about 1.0 mg, about 2 mg, about 3.0 mg, or about 5 mg/capsule.

The concentration of lubricant in a composition described herein may be from about 0.01% to about 10% w/w of the composition. In some embodiments, the lubricant in a composition described herein may be about 0.1% to about 1.0%. In some embodiments, the lubricant is magnesium stearate and the concentration of lubricant in a composition described herein may be about 0.01%, about 0.05%, about 0.1%, about 0.25%, about 0.4%, about 0.5%, about 0.75%, about 1.0%, about 1.25%, or about 1.5% w/w of the composition.

The target unit weight of the lubricant may be from about 0.05 to about 5 mg/capsule. In some embodiments, the lubricant is magnesium stearate and the target unit weight is about 0.75, about 0.79 or about 2.4 mg/capsule.

The concentration of filling agent in a composition described herein may be from about. 1% to about 30% w/w of the composition. In some embodiments, the filling agent in a composition described herein may be about 10% to about 15%. In some embodiments, the filling agent is mannitol and the concentration of filling agent in a composition described herein may be about 5%, about 10%, about 15%, or about 20% w/w of the composition.

The target unit weight of the filling agent may be from about 15.0 to about 47.5 mg/capsule. In some embodiments, the filling agent is mannitol and the target unit weight is about 7.5, about 15, about 15.8, or about 47.5 mg/capsule.

It will be understood that quantitative formulas will be adjusted depending on manufacturing final fill weights. Final fill weights may vary from about 150 mg to about 450 mg to about 1000 mg. In some embodiments, an egg protein formulation containing about 0.2 mg egg protein is manufactured with a final fill weight of about 158 mg. In other embodiments, an egg protein formulation containing about 1.0 mg egg protein is manufactured with a final fill weight of about 150 mg. In other embodiments, an egg protein formulation containing about 10.0 mg egg protein is manufactured with a final fill weight of about 450 mg. In other embodiments, an egg protein formulation containing about 100 mg egg protein is manufactured with a final fill weight of about 450 mg.

In some embodiments, solid dosage forms may be in the form of a tablet, (including a suspension tablet, a fast-melt tablet, a bite-disintegration tablet, a rapid-disintegration tablet, an effervescent tablet, or a caplet), a pill, a powder (including a sterile packaged powder (such as a "stick pack" or foil pouch), a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, or granules. In other embodiments, the formulation is in the form of a powder. Additionally, formulations may be administered as a single capsule or in multiple capsule dosage form. In some embodiments, the formulation is administered in two, or three, or four, capsules or tablets or powder packages.

In some embodiments, solid dosage forms, e.g., tablets, effervescent tablets, and capsules, are prepared by mixing egg white protein comprising characterized egg allergens with one or more pharmaceutical excipients to form a bulk blend composition. When referring to these bulk blend compositions as homogeneous, it is meant that the particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., spray drying, pan coating, melt granulation, granulation, fluidized bed spray drying or coating (e.g., Wurster coating), tangential coating, top spraying, tableting, extruding and the like.

The pharmaceutical solid dosage forms described herein can comprise the compositions described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation. In some embodiments, some or all of the particles are coated. In other embodiments, some or all of the particles are microencapsulated. In yet other embodiments, some or all of the egg allergens are amorphous material coated and/or microencapsulated with inert excipients. In still other embodiments, the particles not microencapsulated and are uncoated.

Compressed tablets are solid dosage forms prepared by compacting the bulk blend formulations described above. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the formulation. In other embodiments, the film coating aids in subject compliance (e.g., Opadry® coatings or sugar coating). Film coatings comprising Opadry® typically range from about 1% to about 3% of the tablet weight. In other embodiments, the compressed tablets comprise one or more excipients.

A capsule may be prepared, e.g., by placing the bulk blend formulation, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulations are placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles and one or more excipients are dry blended and compressed into a mass, such as a tablet, having a hardness sufficient to provide a pharmaceutical composition that substantially disintegrates within less than about 30 minutes, less than about. 35 minutes, less than about 40 minutes, less than about 45 minutes, less than about 50 minutes, less than about 55 minutes, or less than about 60 minutes, after oral administration, thereby releasing the formulation into the gastrointestinal fluid.

In some aspects, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with egg allergens which sufficiently isolate egg allergens from other non-compatible excipients. Materials compatible with egg allergens are those that delay the release of the egg allergens in vivo.

Examples of microencapsulation materials useful for delaying the release of the formulations include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Endragit® S12.5, Eudragit® NE30D, and Eudragit® NE 40D, cellulose acetate phthalate, sepifilms such as mixtures of HPMC and stearic acid, cyclodextrins, and mixtures of these materials.

Microencapsulated egg allergens may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

The formulations described herein are administered and dosed in accordance with good medical practice, taking into account the clinical condition of the individual subject, the site and method of administration, scheduling of administration, and other factors known to medical practitioners.

IV. Methods of Use

The formulations described herein may be used in oral immunotherapy (OIT) to treat, a subject suffering from an egg allergy.

Eggs and egg white protein powder are common foods and additives found in many food products. The present egg protein formulations may include relatively small quantities (0.2 to 100 mg/capsule) of egg proteins compared to the quantities contained in many food products and may be delivered via the same route as orally ingested egg-containing products.

A subject treated with the formulations described herein may exhibit a decreased anaphylactic reaction, relating to a decrease in clinical symptoms following treatment of symptoms associated with exposure to an anaphylactic allergen, which can involve exposure via cutaneous, respiratory, gastrointestinal, and mucosal (e.g., ocular, nasal, and aural) surfaces or a subcutaneous injection (e.g., via a bee sting) following treatment. In some embodiments, a subject may exhibit a decreased anaphylactic reaction of about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

A subject treated with a composition described herein may exhibit a decreased humoral response and/or T cell response following treatment. In some embodiments, a subject may exhibit a decreased humoral response and/or T cell response of about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

A subject treated with a composition described herein may exhibit a decreased IgE response and/or a decreased mast cell response following treatment. In some embodiments, a subject may exhibit a decreased IgE response and/or a decreased mast cell response of about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

A subject treated with the formulation may also exhibit an increased IgG4 response which replaces the IgE antibodies and tempers the immune response to allergens thus lessening the likelihood of an allergic reaction.

A subject treated with the formulations described herein may be better able to withstand an oral food challenge (OFC) following treatment.

A subject treated with a composition described herein may be desensitized to egg allergy following treatment. In some embodiments, a subject may be desensitized by about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

The compositions described herein may be administered in an escalation schedule. In some embodiments, escalating doses are administered to the subject on day 1 of treatment. For example, a subject may be administered, 1, 2, 3, 4 or 5 doses of a composition described herein on day 1. In another example, a subject may be administered 5 doses of a composition described herein in 30 minute increments on day 1. Subjects return on day 2 and receive a maximum tolerated dose. Subjects with moderate symptoms observed on day 2 may return on day 3 for the next lower dose under observation in a monitored clinic setting. Subjects able to withstand treatment on the initial day of treatment may be administered one or more further doses of a composition described herein.

In some embodiments, a subject is further administered 1, 2, 3, 4, 5, 6, 7, 8 or 9 additional escalating doses of a composition described herein. The additional escalating doses may be administered to a subject in two-week intervals.

Following the final administration, the subject may, in some instances, be subject to an oral food challenge to determine if the subject has been desensitized to egg allergy.

In some embodiments, the initial day escalation schedule is shown in Table 1.

TABLE 1

Initial Day Escalation Schedule

| Dose # | Egg protein Formulation Dose | Cumulative Egg protein Formulation Dose if No De-escalation |
| --- | --- | --- |
| 1 | 0.2 mg | 0.2 mg |
| 2 | 0.4 mg | 0.6 mg |
| 3 | 0.8 mg | 1.4 mg |
| 4 | 1.6 mg | 3.0 mg |
| 5 | 3.0 mg | 6.0 mg |

Doses are administered at a frequency standard of every 30 minutes. Subjects at the end of the first day, tolerating less than 1.6 mg single dose may, in some cases, be considered an initial day escalation desensitization failure.

Subjects tolerating a 1.6 or 3 mg single dose may proceed with the greatest tolerated dose to be given daily (first dose given in clinic setting under observation). All escalations occur after at least 2 weeks and single dose increases in the clinic from 1.6 to 3 mg may be attempted.

All subjects return on day 2 and receive their maximum tolerated dose under direct observation. Subjects with moderate symptoms observed on day 2 will return on day 3 for the next lower dose under observation in monitored clinic setting. Doses on day 2, 3 and 4 may be at least 1.6 mg or the subject, in some instances, may be considered an escalation failure.

Following the initial escalation, and if a subject does not have an adverse event, the escalation dose schedule shown in Table 2 may be followed in some embodiments.

TABLE 2

Escalation Dose Schedule

| Dose # | Dose (Protein) | Interval (weeks) | % Increase |
| --- | --- | --- | --- |
| 6 | 6 mg | 2 | |
| 7 | 12 mg | 2 | 100% |
| 8 | 20 mg | 2 | 67% |
| 9 | 40 mg | 2 | 100% |
| 10 | 80 mg | 2 | 100% |
| 11 | 120 mg | 2 | 50% |
| 12 | 160 mg | 2 | 33% |
| 13 | 200 mg | 2 | 25% |
| 14 | 240 mg | 2 | 20% |
| 15 | 300 mg | 2 | 25% |

In other embodiments, an escalation dosing schedule can include day 1 escalation to 50 mg and a 32-week dose escalation with daily dosing as shown in Table 3.

TABLE 3

Initial Day and Escalation Dosing Schedule

| Dose # | Dose (Protein) | Interval (weeks) | % Increase |
| --- | --- | --- | --- |
| 1-10 | 50 mg | | Escalation to 50 mg dose |
| 11 | 80 mg | 2 | 60% |
| 12 | 100 mg | 2 | 25% |
| 13 | 120 mg | 2 | 20% |
| 14 | 160 mg | 2 | 33% |
| 15 | 200 mg | 2 | 25% |
| 16 | 250 mg | 2 | 25% |
| 17 | 300 mg | 2 | 30% |
| 18 | 360 mg | 2 | 20% |
| 19 | 440 mg | 2 | 22% |
| 20 | 500 mg | 2 | 14% |
| 21 | 700 mg | 2 | 40% |
| 22 | 1000 mg | 2 | 43% |
| 23 | 1200 mg | 2 | 20% |
| 24 | 1500 mg | 2 | 25% |
| 25 | 1800 mg | 2 | 20% |
| 26 | 2000 mg | 2 | 11% |

In some embodiments of such methods, immediately prior to administration, an encapsulated capsule formulation may be broken apart and the ingredients mixed into taste-masking food.

In other embodiments, subjects continue taking active treatment for a 3-, 6-, 12-, 24-month or longer maintenance period. In other embodiment, subjects are updosed to 300 mg (as per dose 17) and then they are maintained at 300 mg for a long period of time (minimum 3-6 months). In other embodiments, the subjects are updosed to 1000 mg and then maintained at 1000 mg for a long period of time (minimum 3-6 months) and up to years or a lifetime. These differ from continual updosing in that the subject is updosed to a specific dose and maintained for a long period of time.

Subjects may be monitored for onset of systemic symptoms including, for example, flushing, intensive itching on the skin, and sneezing and runny nose. Sense of heat, general discomfort and agitation/anxiety may also occur.

In some embodiments, the formulations provided herein are administered one or more days to a subject suffering from an egg allergy.

In some embodiments, the subject is able to increase the amount of protein they can consume without an allergic reaction by at least about 100% compared to a subject administered a placebo or not receiving treatment.

In other embodiments, the subject exhibits a reduced humoral response and/or a reduced T cell response. In other embodiments, the subject exhibits reduced anaphylaxis, a reduced mast cell response, a reduced IgE response, reduced hives, or a combination thereof.

In some embodiments, a formulation provided herein may be administered in conjunction with a food product.

A subject may be administered 1, 2, 3, 4 or 5 doses of a formulation provided herein on the first day of treatment. In some embodiments, a subject is administered 10 doses on the first day of treatment. In other embodiments, the subject is administered said doses in 30 minute intervals. The method may, in some instances further comprise one or more additional treatments. In some embodiments, the one or more additional treatments comprise administration of a composition in two-week intervals. In other embodiments, the one or more additional treatments comprise 1, 2, 3, 4, 5, 6, 7, 8, 9, or more doses of a composition.

Provided herein is a method of desensitizing a subject suffering from an egg allergy comprising administering one or more doses of a composition in accordance with aspects of the present technology, wherein the method can comprise the following steps: (a) administering to the subject escalating doses of 0.2 mg, 1.0 mg, 1.5 mg. 3.0 mg, and 6.0 mg in 30-minute intervals on day 1 of the treatment regimen; (b) optionally, administering to the patient a maximum tolerated dose on day 2 of the treatment regimen; and (c) administering to the subject single doses of 12 mg, 20 mg, 40 mg, 80 mg, 120 mg, 160 mg, 200 mg, 240 mg, 300 mg, 360 mg, 440 mg, 500 mg, 700 mg, 1000 mg, 1200 mg, 1500 mg, 1800 mg, and 2000 mg in two-week intervals.

In some embodiments, the method can further comprise administering an oral food challenge (OFC) following completion of the treatment regimen.

V. Combination Therapies

The formulations and methods described herein may also be used in conjunction with other well-known therapeutic compounds that are selected for their particular usefulness against the condition that is being treated. In general, the formulations described herein and, in embodiments where combinational therapy is employed, other compounds, do not have to be administered in the same formulation, and may, because of different physical and chemical characteristics, have to be administered by different routes, or they may be combined in a single formulation. The determination of the mode of administration and the advisability of administration, where possible, in the same formulation, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the subject and the appropriate treatment protocol. The compounds may be administered concurrently (e.g., simultaneously, essentially simultaneously or within the same treatment protocol) or sequentially, depending upon the condition of the subject, and the actual choice of compounds used. The determination of the order of administration, and the number of repetitions of administration of each therapeutic agent during a treatment protocol, is well within the knowledge of the skilled physician after evaluation of the severity of egg allergy being treated and the condition of the subject.

It is understood that the dosage regimen to treat, prevent, or ameliorate egg allergy, can be modified in accordance with a variety of factors. These factors include the age, weight, sex, diet, and/or medical condition of the subject. Thus, the dosage regimen actually employed can vary widely and therefore can deviate from the dosage regimens set forth herein.

The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In some embodiments, the formulation is administered with at least one other anti-histamine agent, corticosteroid, beta agonist, anti-inflammatory agent, an anti-IgE antibody (e.g., omalizumab) and/or epinephrine. In some embodiments, the formulation is administered with at least one membrane stabilizing agent (e.g., cromolyn). The membrane stabilizing agent acts to stabilize the membranes of mast cells so that they cannot release molecules that induce anaphylaxis.

VI. Examples

The present technology may be better understood by reference to the following non-limiting examples. The following examples are presented in order to more fully illustrate certain embodiments and should in no way be construed, however, as limiting the broad scope of the present technology. While certain embodiments of the present technology have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the methods described herein.

In the examples, egg white protein and formulations comprising egg white protein are tested for stability under various conditions. The total egg protein, ovomucoid protein, ovalbumin protein, and/or lysozyme protein in the egg protein formulations provided herein may be considered "stable" if its concentration is ±10% the original concentration of such protein(s) in the egg protein formulation immediately after manufacture.

Example 1: Evaluation of Egg White Powder

This example describes the physical characterization of the Egg white protein. Egg white protein (Deb El Egg White Powder Lot #PK049/2013) was used as the source of egg protein and was physically characterized by visual inspection for appearance and flow. Particle size studies were also performed using mesh filters. The egg white protein was found to have the following properties (see Table 4):

TABLE 4

| Egg white powder properties: | |
|---|---|
| Appearance (visual analysis) | |
| Color | Off white |
| Texture | Fine powder |
| Flowability | Cohesive |
| Flow Studies | |
| Bulk Density | 0.328 g/ml |
| Tap Density | 0.531 g/ml |
| Carr Index | 38.23 |
| (>25 = poor flowability) | |
| Particle Size Distribution | |
| 100% < 100 mesh (150 microns) | |
| ~82% < 200 mesh (75 microns) | |

Figure 3:
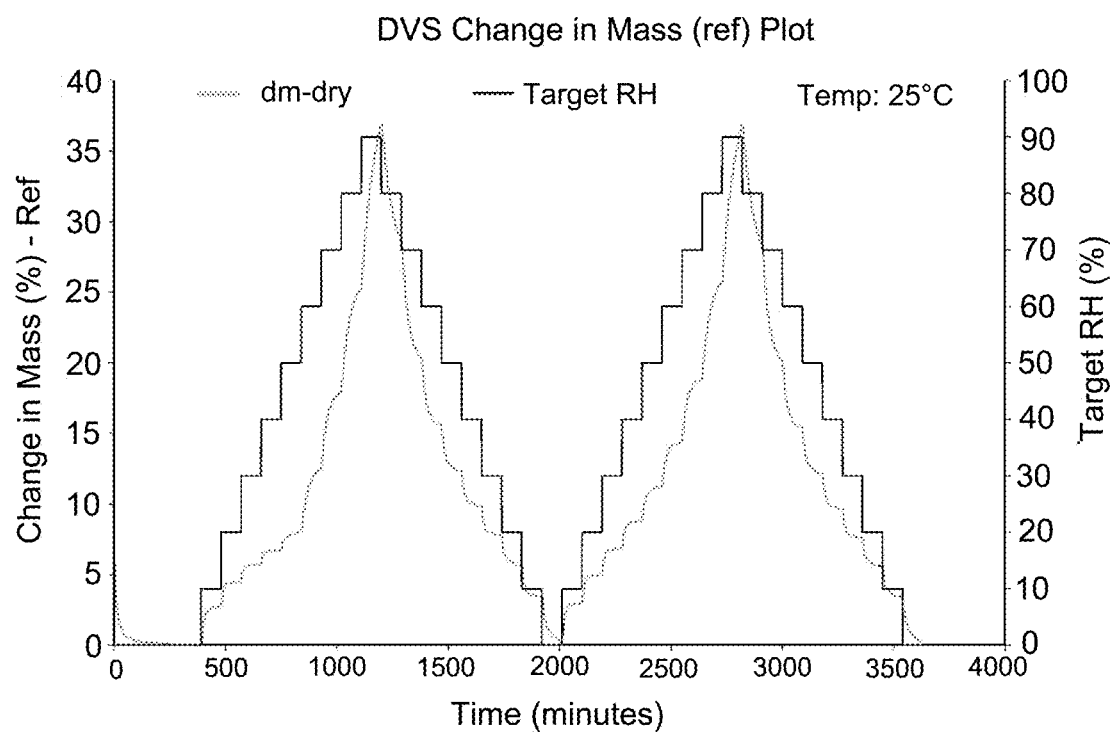
FIG. 3 is a plot showing DVS change in mass for egg white protein for analyzing a rate of moisture uptake in accordance with aspects of the present technology.
Figure 4:
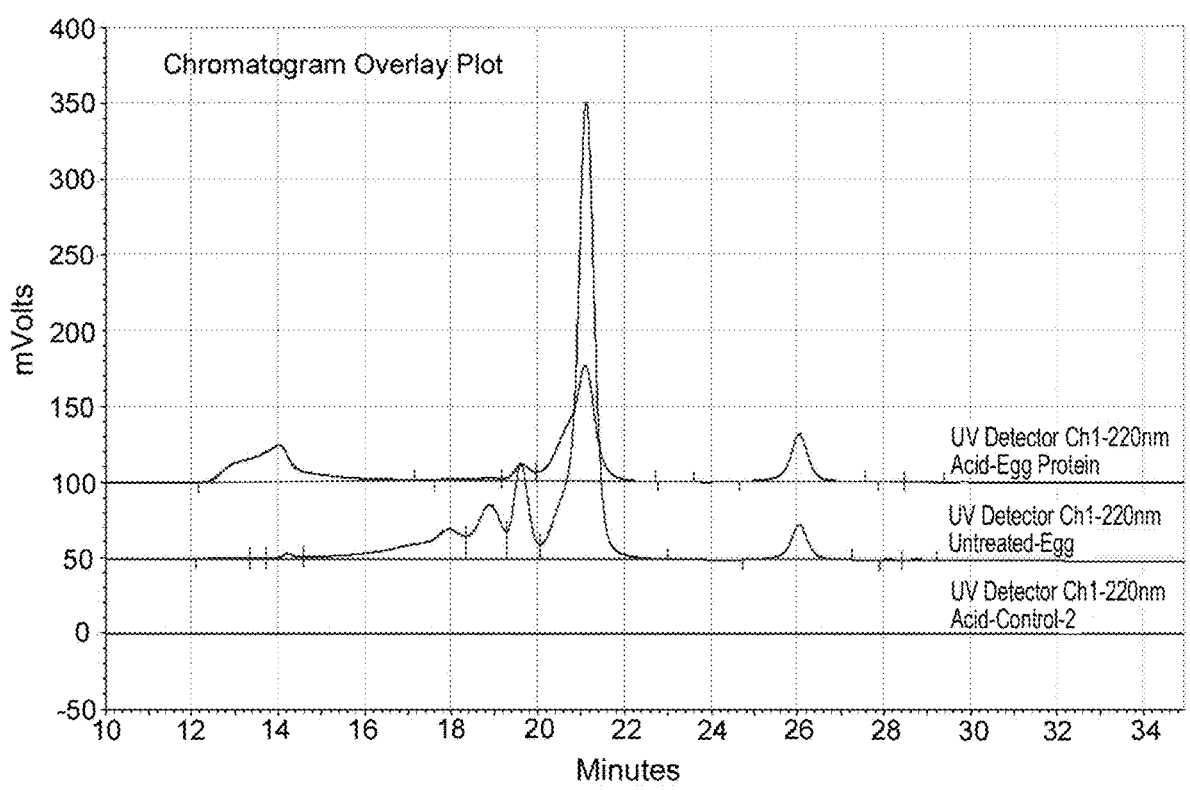
FIG. 4 is a chromatogram overlay of egg white protein (~1 mg/mL protein) exposed to 1 N HCl overnight, untreated egg white protein (~1 mg/mL protein stored @4° C.) and acid control sample in accordance with aspects of the present technology.
Figure 5:
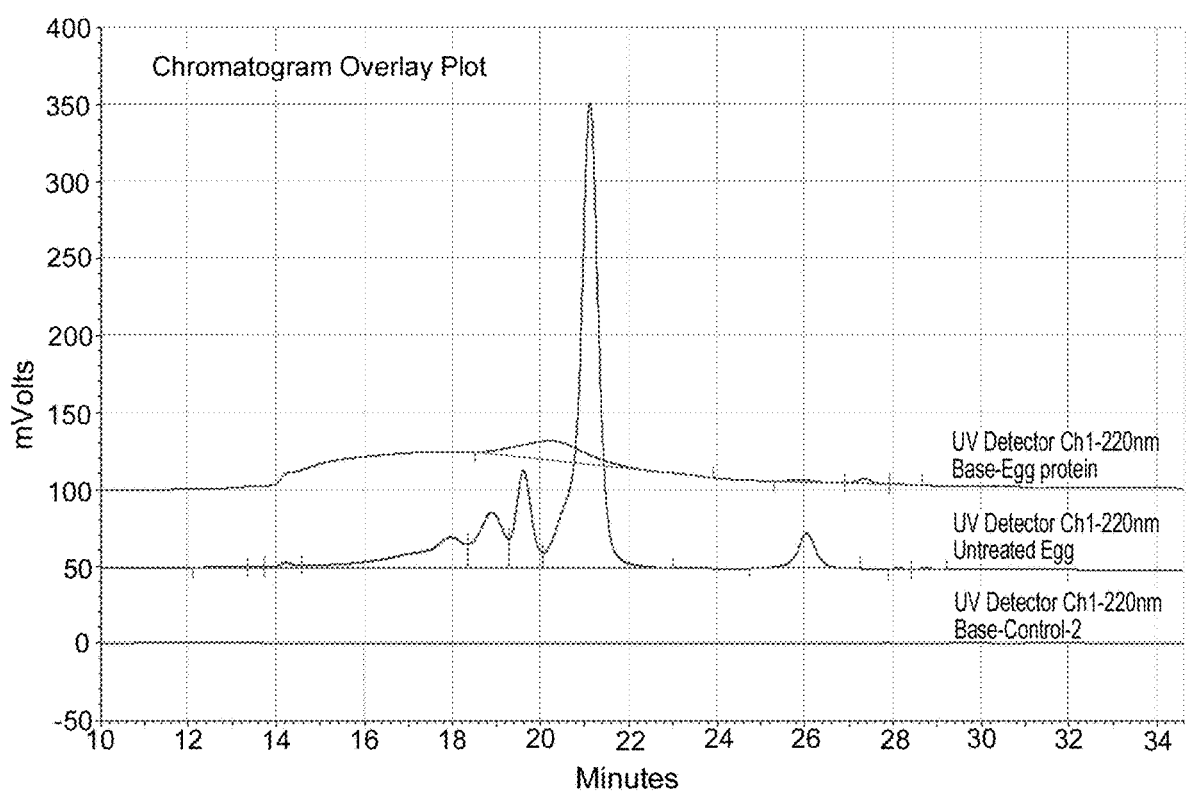
FIG. 5 is a chromatogram overlay of egg white protein (~1 mg/mL protein) exposed to 1 N NaOH overnight, untreated egg white protein (~1 mg/mL protein stored @4° C.) and base control sample in accordance with aspects of the present technology.
Figure 6:
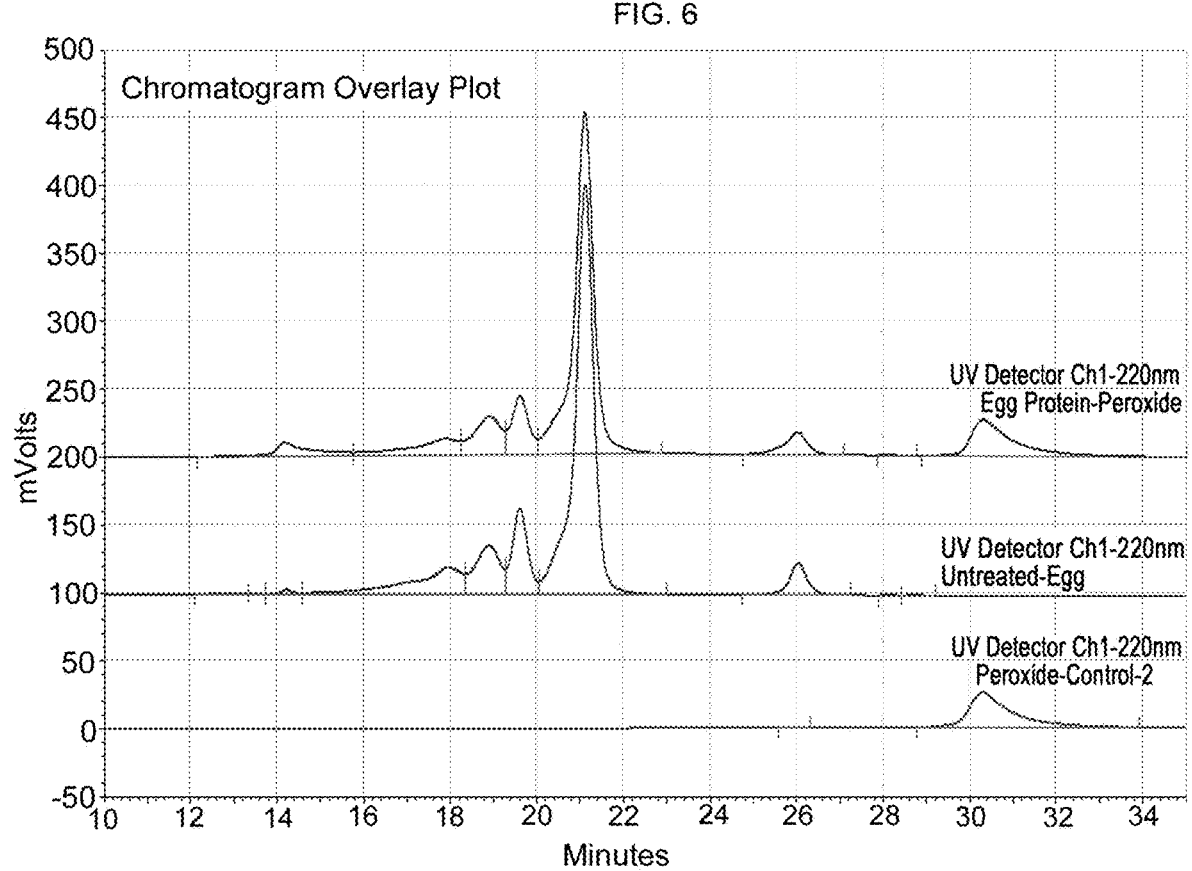
FIG. 6 is a chromatogram overlay of egg white protein (~1 mg/mL protein) exposed to 3% hydrogen peroxide overnight, untreated egg white protein (~1 mg/mL protein stored @4° C.) and base control sample in accordance with aspects of the present technology.
Figure 7:
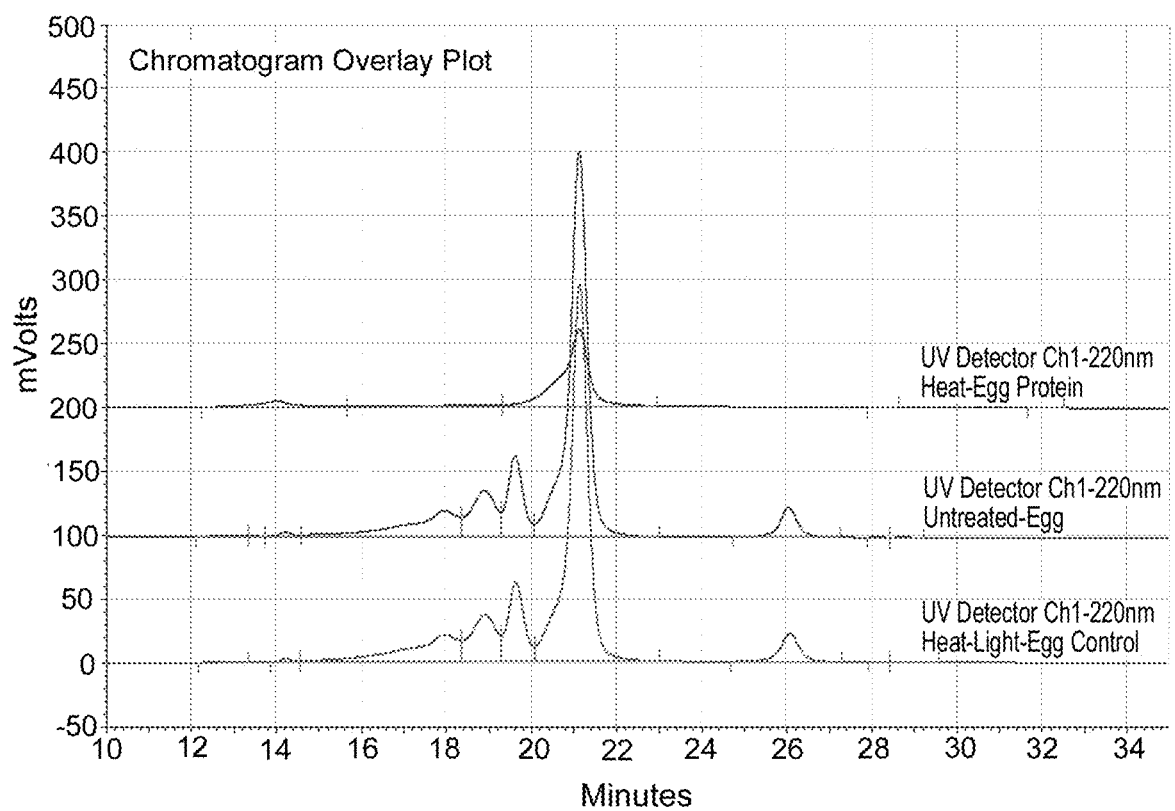
FIG. 7 is a chromatogram overlay of egg white protein (~1 mg/mL protein) exposed to 70° C. heat overnight, untreated egg white protein (~1 mg/mL protein stored @4° C.) and heat control sample in accordance with aspects of the present technology.
Figure 8:
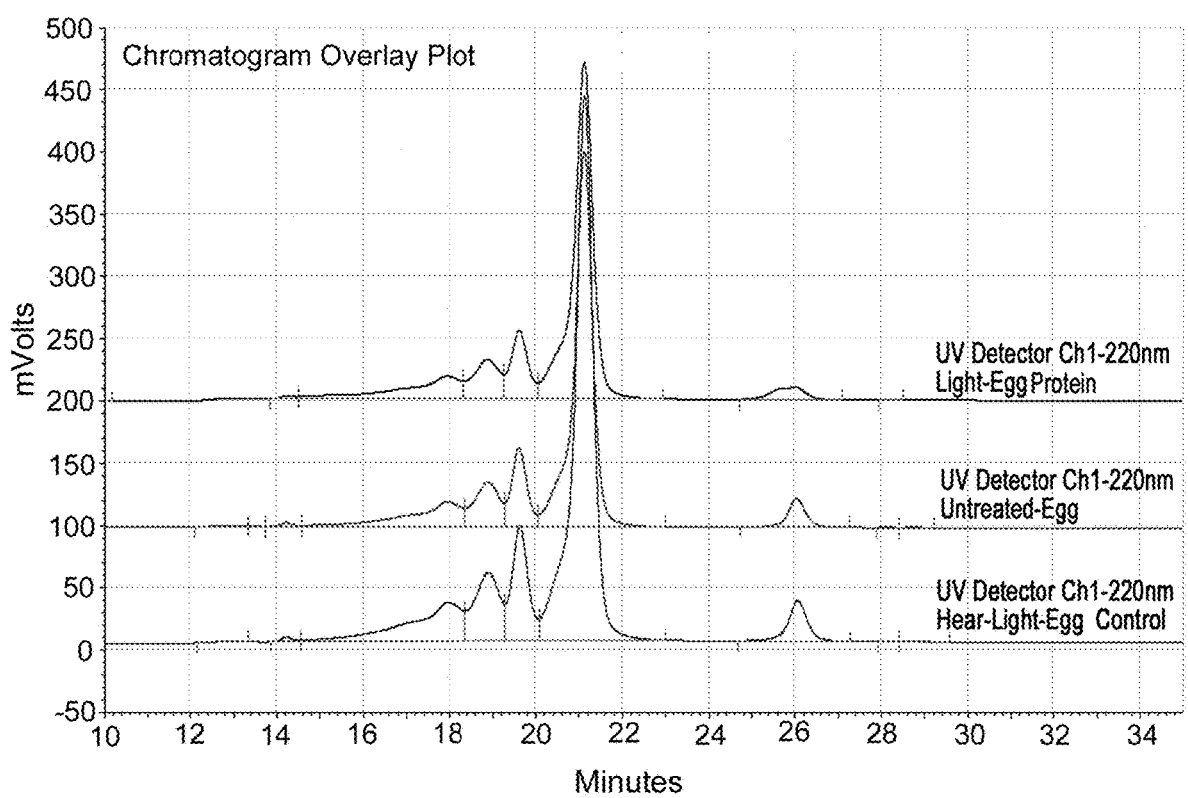
FIG. 8 is a chromatogram overlay of egg white protein (~1 mg/mL protein) exposed to light overnight, untreated egg white protein (~1 mg/mL protein stored @4° C.) and light control sample in accordance with aspects of the present technology.
Figure 9:
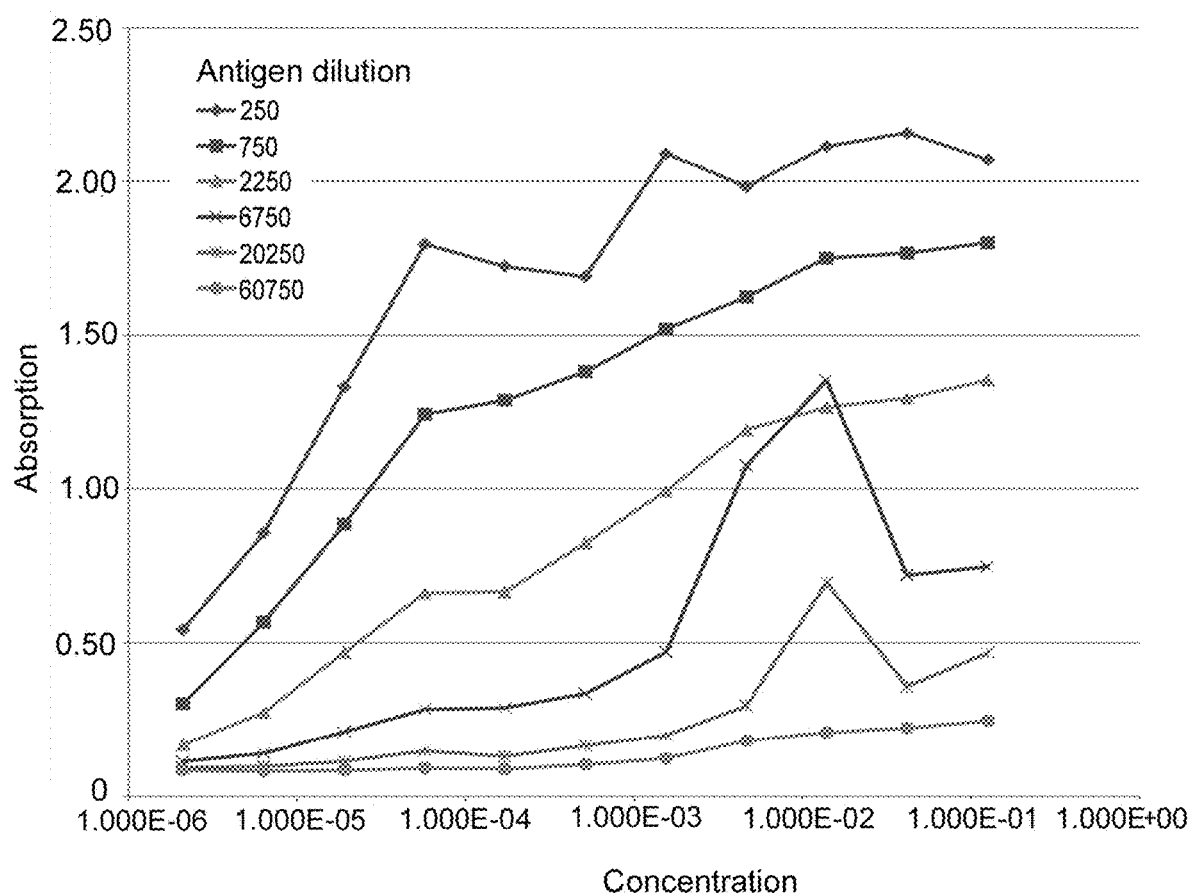
FIG. 9 is an Enzyme-linked immunosorbent assay (ELISA) plot showing primary antibody concentration versus absorbance at varying dilutions of coating antigen for ovomucoid protein standard in accordance with aspects of the present technology.
Figure 10:
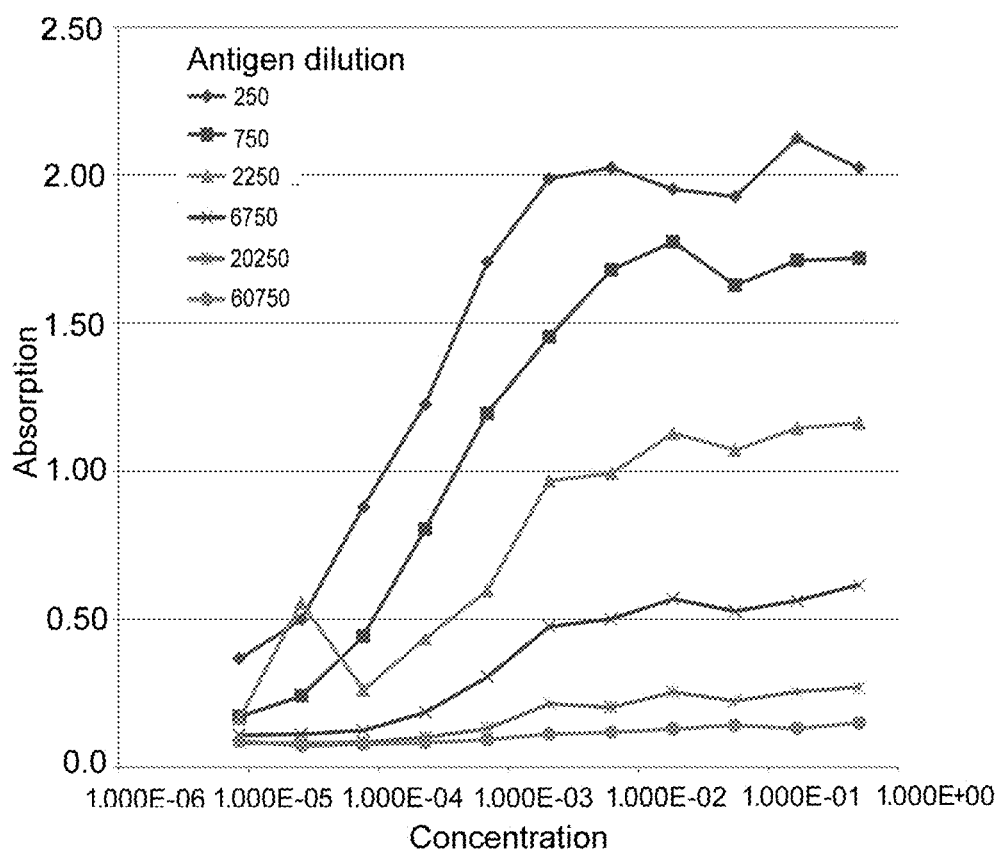
FIG. 10 is an ELISA plot showing primary antibody concentration versus absorbance at varying dilutions of coating antigen for ovomucoid protein sample in accordance with additional aspects of the present technology
Figure 11:
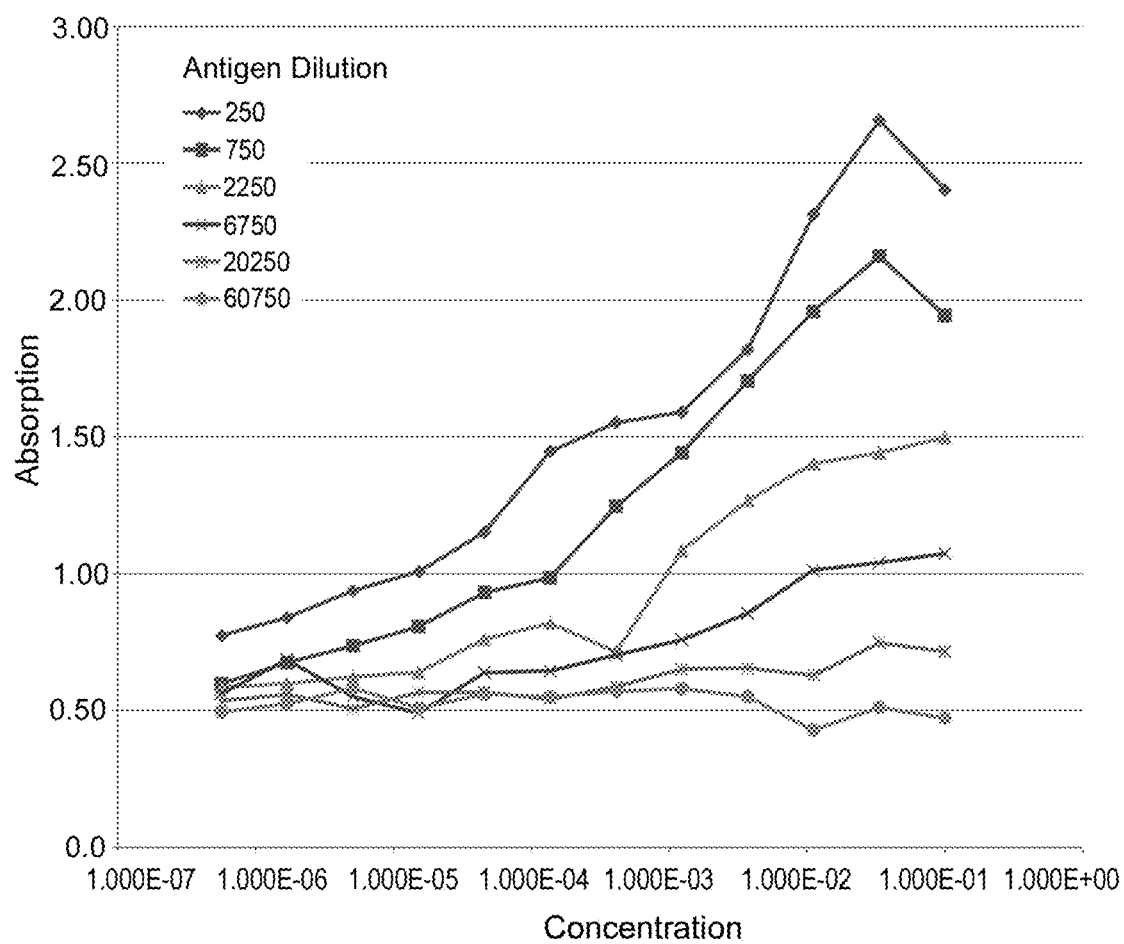
FIG. 11 is an ELISA plot showing primary antibody concentration versus absorbance at varying dilutions of coating antigen for Ovalbumin protein standard in accordance with aspects of the present technology.
Figure 12:
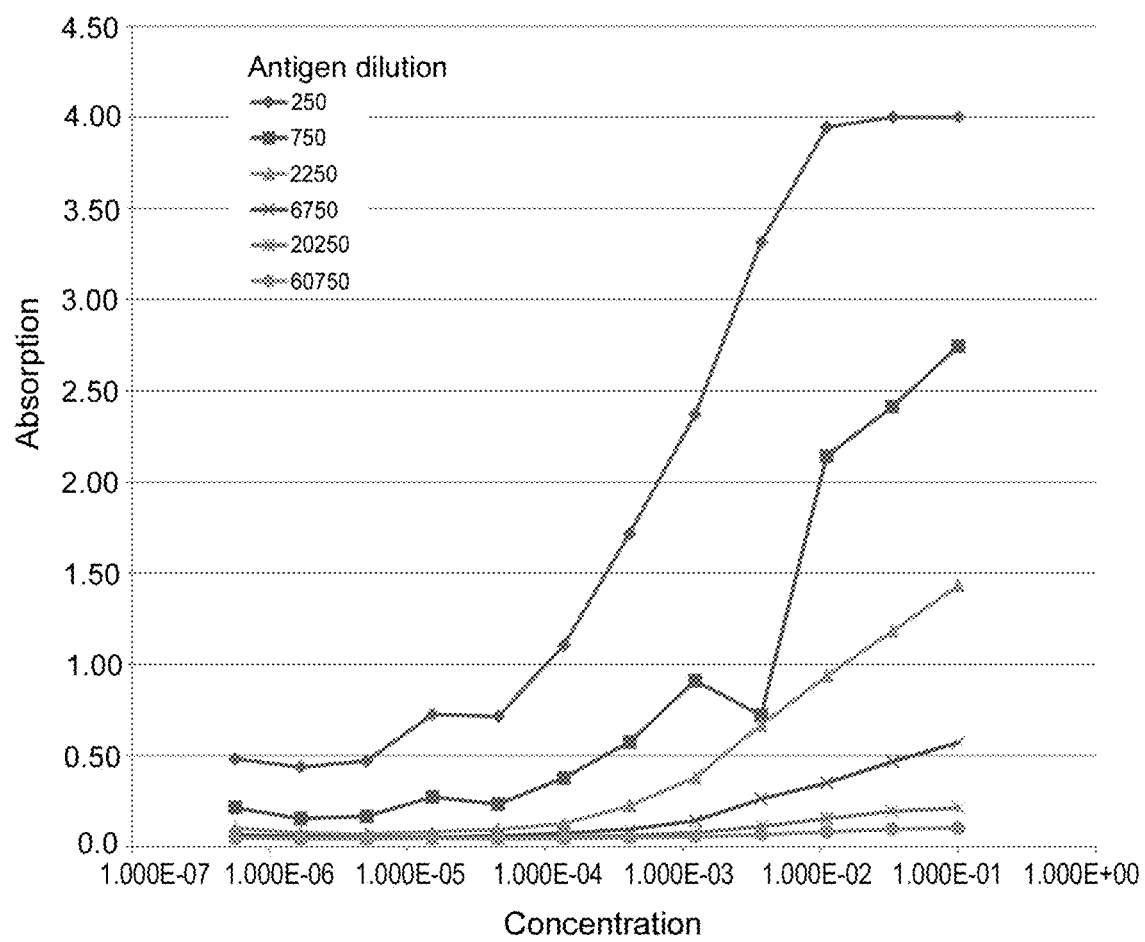
FIG. 12 is an ELISA plot showing primary antibody concentration versus absorbance at varying dilutions of coating antigen for Ovalbumin protein standard, with no secondary antibody and in accordance with additional aspects of the present technology.
Figure 13:
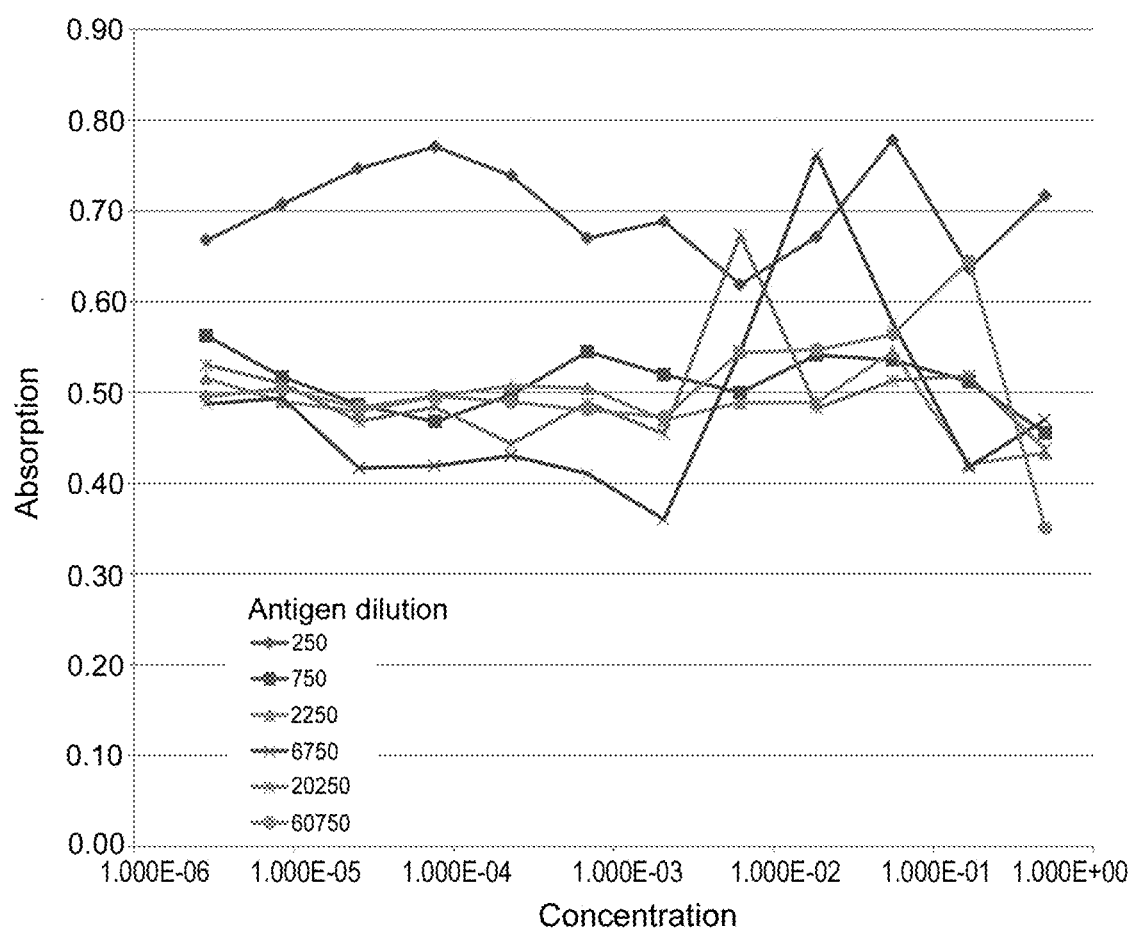
FIG. 13 is an ELISA plot showing primary antibody concentration versus absorbance at varying dilutions of coating antigen for Ovalbumin protein sample in accordance with further aspects of the present technology
Figure 14:
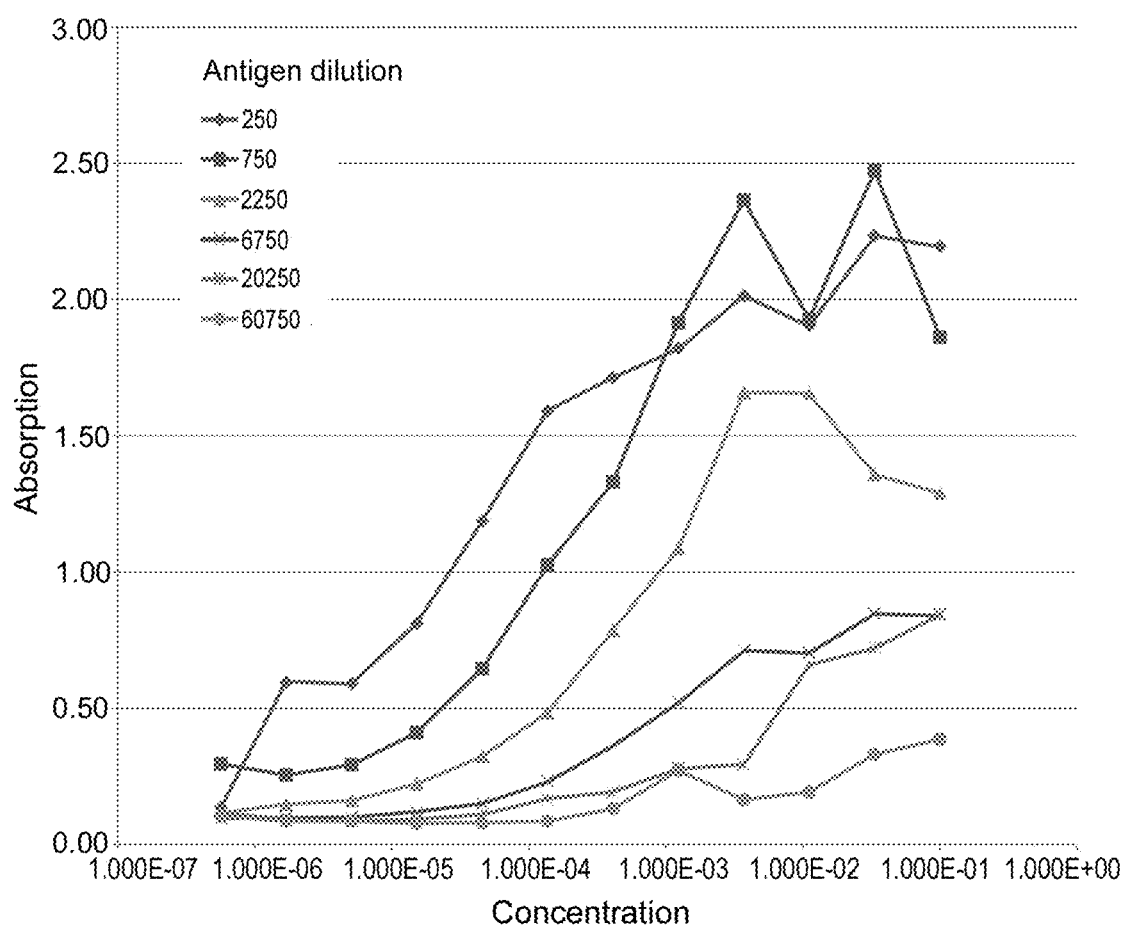
FIG. 14 is an ELISA plot showing primary antibody concentration versus absorbance at varying dilutions of coating antigen for Lysozyme protein standard in accordance with aspects of the present technology.
Figure 15:
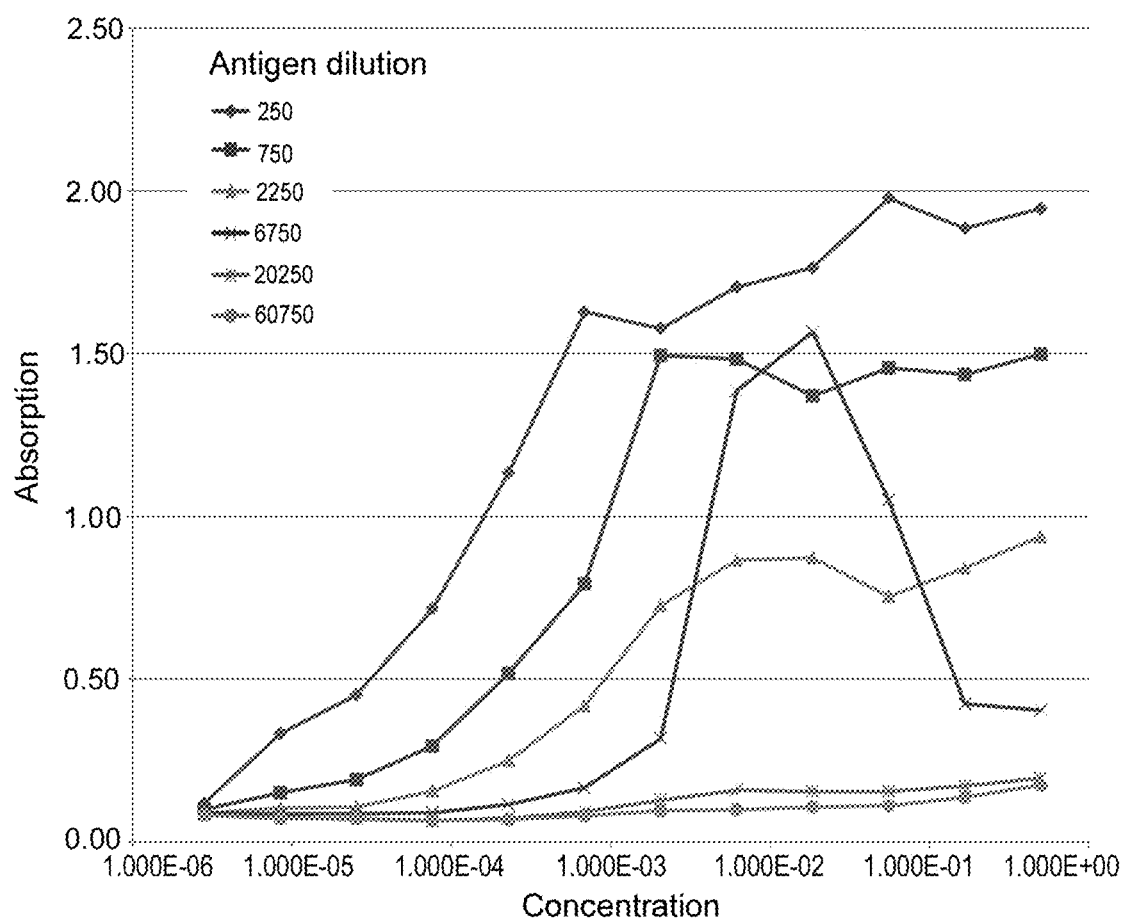
FIG. 15 is an ELISA plot showing primary antibody concentration versus absorbance at varying dilutions of coating antigen for Lysozyme protein sample in accordance with aspects of the present technology.

Dynamic vapor sorption analyses (DVA) were performed to determine the conditions under which egg white protein moisture content increases significantly (potentially decreasing flow and protein stability), and to serve as a baseline for comparison with the egg protein formulations provided herein. Deb El Egg White Powder Lot #PK049/2013 was used and found to have the properties listed in Table 5 below. Further, as shown in FIGS. 1-3, the rate of change in the mass of the sample (rate of moisture uptake) increased significantly at values above 50% relative humidity. As shown in Table 12, at 75% relative humidity, the egg protein formulations provided herein take up less moisture than egg white protein alone.

TABLE 5

Deb El Egg White Powder properties

Moisture Testing

| Dynamic Vapor Sorption | *<10% Change in Mass @ Relative Humidity ≤40% | |
|---|---|---|
| LOD Results for Open Sample at Ambient Conditions for 4 days | Initial LOD 7.04% Final LOD 9.83% | Percent Change in LOD = 39.63% |

Protein Integrity Assay

| Peak # | Retention Time (min) | % Area Under the Curve |
|---|---|---|
| 1 | 28.4 | 8.50 |
| 2 | 29.9 | 9.91 |
| 3 | 31.1 | 10.83 |
| 4 | 33.5 | 66.68 |
| 5 | 41.4 | 4.08 |

Total Protein Assay

| Anhydrous value | 91.9% |
|---|---|
| Use as value | 85.71% |

Example 2: Forced Degradation of Egg White Powder

This example describes tests to determine the stability of egg white protein in the presence of acids, bases, peroxide, light and heat. Acid, base, peroxide and heat were used to stress the egg white protein solutions and the stability was evaluated. Evaluation of the degradation of the samples was based on a chromatographic assay of egg white protein in the stressed samples as compared to unstressed samples.

The acid stressed sample was evaluated as follows: Egg white protein was dissolved in $H_2O$ to form a 1.0 mg/mL solution and exposed to 1.0 N HCl to create an acid stressed sample. The acid stressed sample, an untreated sample containing only 1 mg/ml untreated egg white protein solution, and an acid control containing 1 N HCl were allowed to stand overnight at 4° C. At the end of the time period the test solution was neutralized with 1.0 mL of 0.1 N NaOH and extracted for preparation of chromatography.

The base stressed sample was prepared as follows: Egg white protein was dissolved in $H_2O$ to form a 1.0 mg/mL solution and exposed to 1.0 N NaOH to create a base stressed sample. The base stressed sample, an untreated sample containing only 1 mg/ml untreated egg white protein solution, and a base control containing 1 N NaOH were allowed to stand overnight at 4° C. At the end of the time period the test solution was neutralized with 1.0 mL of 0.1 N HCl and extracted.

The peroxide stressed sample was prepared as follows: Egg white protein was dissolved in $H_2O$ to form a 1.0 mg/mL solution and exposed to 3% hydrogen peroxide to create a peroxide stressed sample. The peroxide stressed sample, an untreated sample containing only 1 mg/ml untreated egg white protein solution, and a peroxide control containing [3% hydrogen peroxide] were allowed to stand overnight at 4° C.

The heat stressed sample was prepared as follows: Egg white protein was dissolved in $H_2O$ to form a 1.0 mg/mL solution and exposed to 70° C. overnight to create a heat stressed sample. An unheated sample containing 1 mg/ml unheated egg white protein solution, and a control were allowed to stand overnight at 4° C.

The light exposed sample was prepared as follows: Egg white protein was dissolved in $H_2O$ to form a 1.0 mg/mL solution and exposed to light overnight to create a light exposed sample. A sample containing 1 mg/ml egg white protein solution stored in the dark, and a control were allowed to stand overnight at 4° C.

The samples from the degradation studies were analyzed using an HPLC System (Size Exclusion Chromatography—SEC) under the following conditions: Column (two in series): Phenomenex Yarra SEC 2000, 3 µm, 300×7.8 mm with the following reagents and conditions: Mobile Phase: 0.05 M Na2HPO4, 0.05 M NaH2PO4, 0.15 M NaCl, pH 6.8; Flow rate: 0.5 mL/min; Injection volume: 20 µL; Run time: approximately 60 minutes; Detector: UV 220 nm; Pump mode: Isocratic; Column temperature: Ambient; and Needle wash: Water.

The results in FIGS. 4-8 showed no interfering peaks in the control preparations. Peaks were evaluated qualitatively, and as shown in FIGS. 4-8, significant degradation occurred with exposure to acid, base, and heat, whereas the egg white protein solutions were demonstrated to be less sensitive to peroxide and light.

Example 3: Identification and Quantification of Egg White Proteins

In this example, several assays were developed in order to facilitate the quantification of the three major egg protein allergens, Ovomucoid, Ovalbumin, and Lysozyme. The assays tested were ELISA assays, size exclusion chromatography methods, and immunoblot techniques.

The ELISA assay was performed as follows: Coating Antigen was incubated overnight at 4° C., then washed 3× with PBS w/0.05% Tween 20. Then the antigen was blocked with 1% BSA in PBS for 1 hour at 40° C. and washed 3× with PBS w/0.05% Tween 20. The primary antibody was added and incubated for 1.5 hours at 40° C. and washed 3× with PBS w/0.05% Tween 20. The Secondary Antibody (1:10000 for Ovomucoid and Ovalbumin, 1:5000 for Lysozyme, no dilution) was added and incubated for 1.5 hours at 40° C. The detection substrate was added and incubated until there was a color change at room temperature, at which point the stop solution was added. Absorbance was read at 450 nm using an automated microtiter plate ELISA reader. An example of a microtiter plate is shown in FIG. 25 as Table 6.

The ELISA assay was performed using various dilutions for each protein (represented by different lines in FIGS. 9-15) at varying primary antibody dilutions and was used to determine the optimal conditions for each reagent, such that the amount of each egg, protein can be determined from the most sensitive (steepest slope) portion of the titration curve. Primary antibody concentration versus absorbance is shown in FIGS. 9-15 for each dilution of each protein. The secondary antibody concentration was 1:5000 for all Lysozyme samples and 1:10000 for all Ovomucoid and Ovalbumin samples, unless otherwise indicated.

Figure 16:
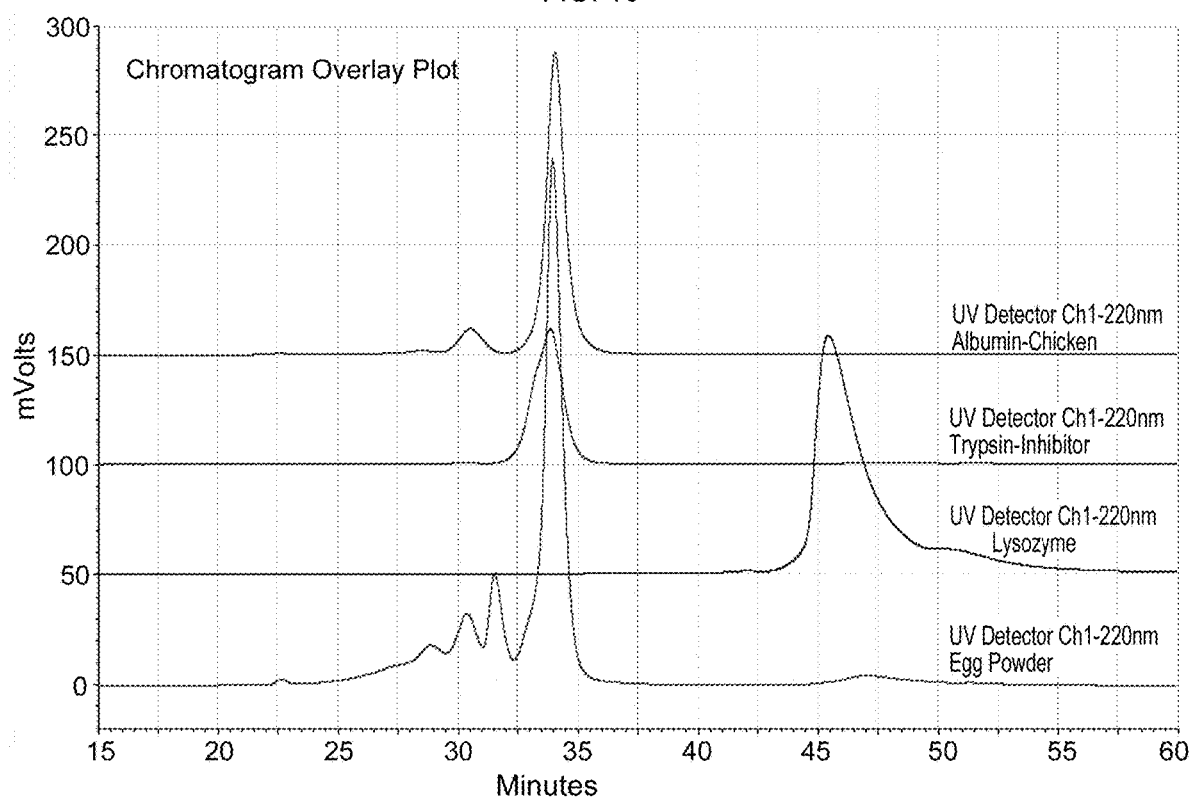
FIG. 16 is a chromatogram overlay of (from top to bottom) Chicken. Egg Albumin (~0.04 mg/mL), Trypsin Inhibitor (~0.04 mg/mL), Lysozyme (~0.04 mg/mL), and Egg White Protein (~0.01 mg/ml) using two Phenomenex Yarra 2000 SEC columns in series and in accordance with aspects of the present technology.
Figure 17:
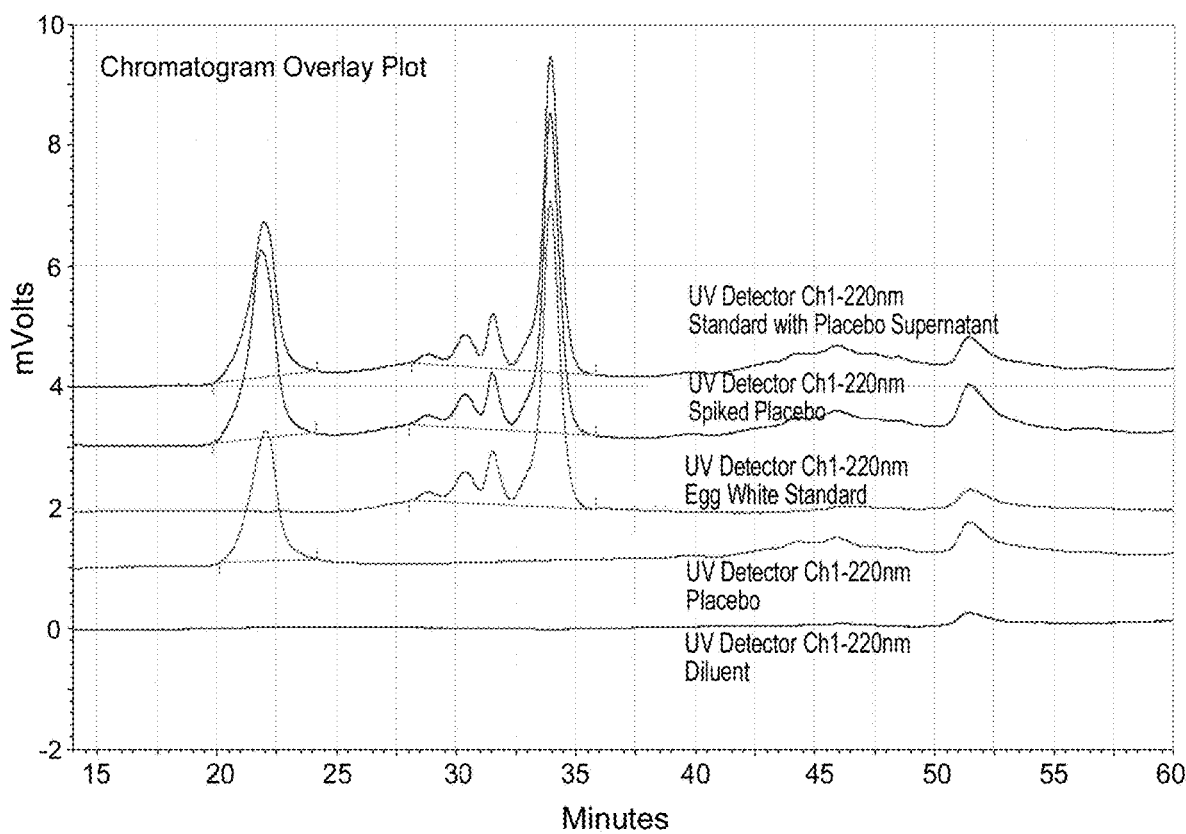
FIG. 17 is a chromatogram overlay of Egg White Protein Placebo (Starch 1500), Egg White Protein Standard (~0.02 mg/mL protein), Placebo spiked with Egg White Protein (~0.02 mg/mL protein) and Egg White Protein Standard prepared with Placebo supernatant and in accordance with aspects of the present technology.

A Size Exclusion Chromatography (SEC) assay using individual egg proteins as well as blended powders was conducted under the SEC conditions used in the forced degradation analysis of Example 2. FIG. 16 shows the chromatogram overlays of Chicken Egg Albumin (~0.4 mg/mL), Trypsin Inhibitor (~0.4 mg/mL), Lysozyme (~0.4 mg/mL) and Egg White Protein (~1.0 mg/mL) using two Phenomenex Yarra 2000 SEC columns in series. FIG. 17 shows the chromatogram overlays of Egg White Protein Placebo (Starch 1500), Egg White Protein Standard (~0.02 mg/mL protein), Placebo spiked with Egg White Protein (~0.02 mg/mL protein) and Egg White Protein Standard prepared with Placebo supernatant.

A Size Exclusion Chromatography (SEC) assay using egg protein in the different solvents shown in Table 7 was conducted under the SEC conditions used in Example 2.

TABLE 7

1 mg/mL Egg Protein Peak Areas using Size Exclusion Chromatography

| Diluent | Unk 01 | Unk 02 | Unk 03 | Total Area |
| --- | --- | --- | --- | --- |
| 50 mM NaPO4 | ND | 16868750 | 40301 | 16909051 |
| 50 mM NaPO4 w/0.1% SDS | ND | 14912834 | 80028 | 14992862 |
| 50 mM KPO4 | ND | 17161823 | 19266 | 17181089 |
| 50 mM KPO4 w/0.1% Tween 20 | ND | 16311466 | 23669 | 16335135 |
| 200 mM NaPO4 | ND | 16873871 | 28161 | 16902032 |
| 200 mM NaPO4 w/0.1% SDS | 43318 | 16537051 | ND | 16580369 |
| 200 mM KPO4 | ND | 17276749 | 206260 | 17483009 |
| 200 mM KPO4 w/0.1% Tween 20 | ND | 17564491 | 144179 | 17708670 |
| PBS | 50121 | 18147730 | 57944 | 18255795 |
| PBS w/0.1% SDS | ND | 12551258 | 129076 | 12680334 |
| PBS w/0.1% Tween 20 | ND | 16270054 | 181413 | 16451467 |

ND = Not Detected

Figure 18:
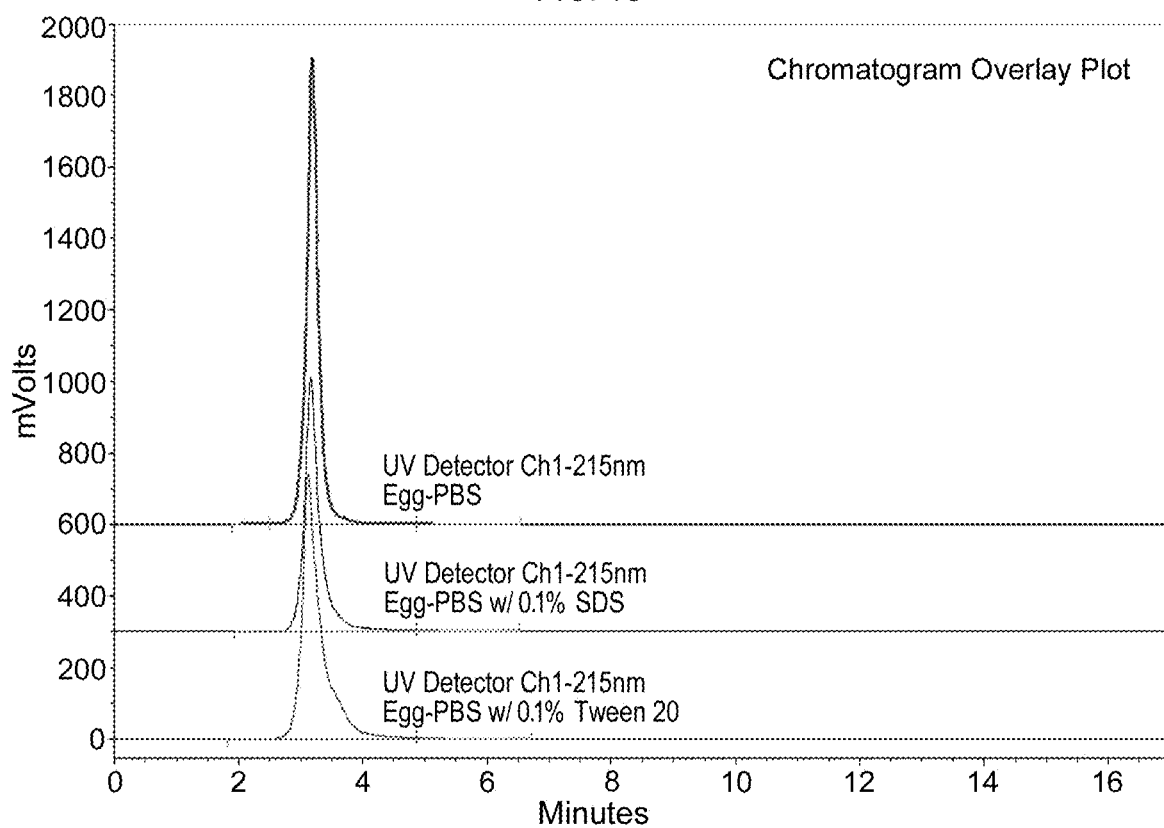
FIG. 18 is a chromatogram overlay of 1 mg/mL Egg White Protein diluted with PBS solutions using size exclusion chromatography in accordance with aspects of the present technology.
Figure 19:
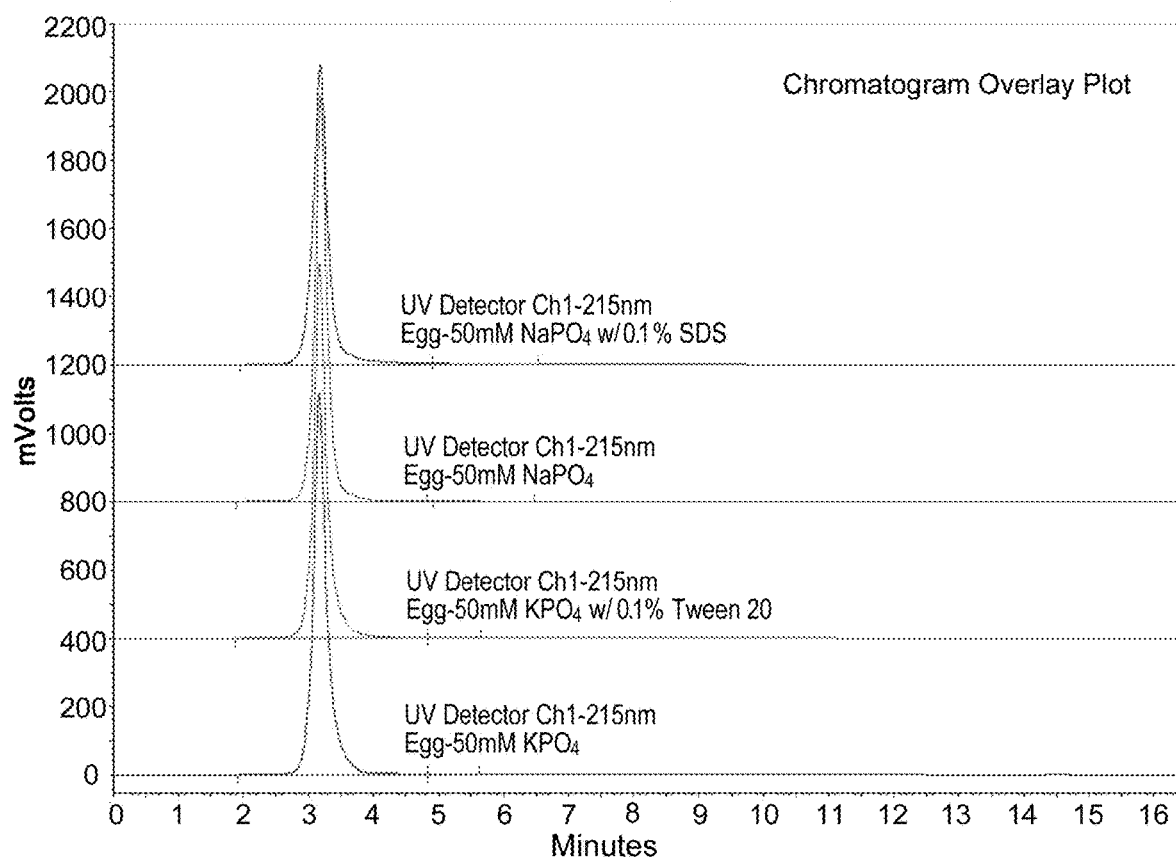
FIG. 19 is a chromatogram overlays of 1 mg/mL Egg White Protein diluted with 50 mM Phosphate Buffer solutions using size exclusion chromatography in accordance with aspects of the present technology.
Figure 20:
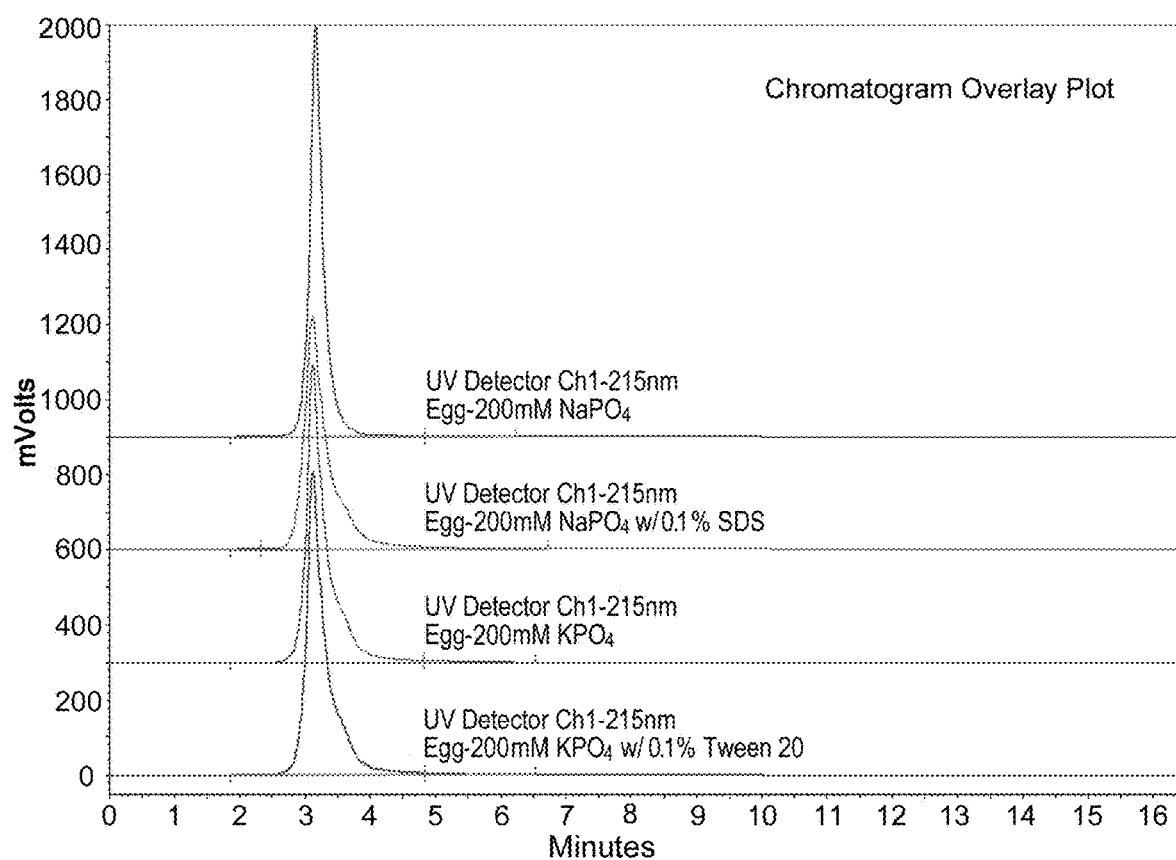
FIG. 20 is a chromatogram overlay of 1 mg/mL Egg White Protein diluted with 200 mM Phosphate Buffer solutions using size exclusion chromatography in accordance with aspects of the present technology.
Figure 21:
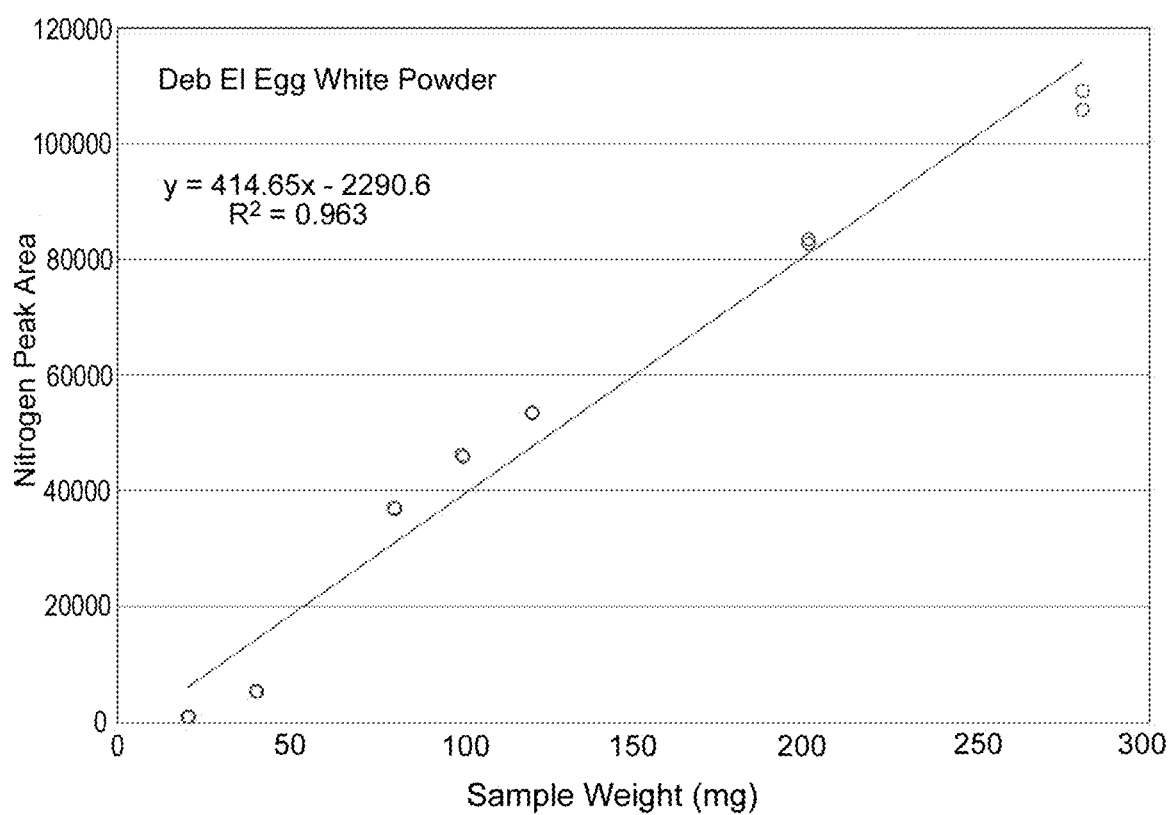
FIG. 21 is a plot showing linearity between the sample weight (x-axis) and nitrogen peak area (y axis) of Egg Protein Blends in accordance with aspects of the present technology.

FIG. 18 shows the chromatogram overlays of 1 mg/mL Egg White Protein diluted with PBS solutions using size exclusion chromatography. FIG. 19 shows the chromatogram overlays of 1 mg/mL Egg White Protein diluted with 50 mM Phosphate Buffer solutions using size exclusion chromatography. FIG. 20 shows the chromatogram overlays of 1 mg/mL Egg White Protein diluted with 200 mM Phosphate Buffer solutions using size exclusion chromatography. Nitrogen Combustion Protein Quantification (Dumas Method Combustion) was performed as follows: Dumatherm® Combustion assays permit quantification of relatively small amounts of protein in a sample. Such an assay was performed in which egg white protein samples were combusted to determine the amount of $N_2$ in a sample. The samples were combusted using an $O_2$ flow rate of 1.4 mL per mg of sample and about 140 mg. EDTA standard amount. The amount of $N_2$ was used to determine the total protein content in the sample (data in Table 8) using the following calculation: Assay (% LC)=(% Nitrogen−CF)×TCFW/LC× 5.46/100×100% Where: % Nitrogen=% Nitrogen obtained in the Sample, CF=Nitrogen content found in the Placebo, TCFW=Target Capsule Fill Weight, LC=Label Claim of the Drug Product, 5.46=Conversion Factor from Nitrogen to Protein Content. Linearity for blended egg protein protein was shown in FIG. 21 between the sample weight (x axis) and nitrogen peak area (y axis) as determined by the Dumatherm method. So as the weight of each peak (protein) increases in molecular weight (later elution time), the total nitrogen % area of each peak as plotted increases in a proportional and linear fashion ($R^2$=0.97). The results show the column method, as confirmed by the Dumatherm method, can be used to both separate egg white proteins and to determine total protein in a sample.

TABLE 8

Amount of N2

| Sample Wt (mg) | $N_2$ Peak area | % Nitrogen | mg N | Corrected Weight | % N2 based on corrected wt. | % Total Protein |
| --- | --- | --- | --- | --- | --- | --- |
| 20.57 | 1034 | 13.13 | 2.70 | 19.13 | 14.12 | 88.25 |
| 20.40 | 1027 | 13.16 | 2.68 | 18.97 | 14.15 | 88.41 |
| 40.48 | 5380 | 13.29 | 5.38 | 37.65 | 14.29 | 89.32 |
| 40.22 | 5336 | 13.27 | 5.34 | 37.40 | 14.27 | 89.17 |
| 80.32 | 37110 | 13.36 | 10.73 | 74.69 | 14.36 | 89.75 |
| 80.54 | 36940 | 13.25 | 10.67 | 74.90 | 14.25 | 89.04 |
| 100.21 | 46250 | 13.79 | 13.82 | 93.19 | 14.83 | 92.67 |
| 100.41 | 45950 | 13.66 | 13.71 | 93.38 | 14.69 | 91.79 |
| 120.47 | 53580 | 13.63 | 16.42 | 112.04 | 14.66 | 91.61 |
| 120.42 | 53410 | 13.59 | 16.36 | 111.99 | 14.61 | 91.30 |
| 200.93 | 83550 | 14.07 | 28.26 | 186.86 | 15.13 | 94.54 |
| 200.74 | 82740 | 13.91 | 27.92 | 186.69 | 14.95 | 93.47 |
| 280.45 | 105900 | 13.67 | 38.33 | 260.81 | 14.70 | 91.85 |
| 280.54 | 109100 | 14.22 | 39.89 | 260.90 | 15.29 | 95.56 |
| | | | | | Avg | 91.19 |
| | | | | | RSD | 2.53 |

The results show that any of the assays could be used to identify and quantify the proteins in egg whites to provide formulations having consistent levels of the egg proteins ovalbumin, ovomucoid and lysozyme.

Example 4: Excipient Compatibility with Egg White Protein

The purpose of this compatibility study was to identify excipients for a dry blend process which facilitate the goals of processability on the encapsulation and sachet or pouch packaging equipment, clean emptying of the contents from the capsule shells or sachet packages, and chemical compatibility with the egg proteins being dosed. As shown in Table 9, the excipients evaluated in this study were grouped by functionality as filling agents, diluents, glidants, colorants, capsule shell components, and lubricants. Diluents and filling agents were evaluated at a ratio of 1:1 versus the egg proteins (which constitute 91% of the egg white protein by weight). Lubricants, glidants, colorants, and capsule shell material were evaluated at a ratio of 10:1 (egg protein versus the excipient or ingredient). Some excipients were found to be incompatible with egg white protein in early formulation development and were excluded. These are normal accepted ranges/ratios based upon the functionality of each of the class of excipients and or material tested.

Twelve excipients were evaluated including one filling agent, three diluents, two glidants/anticaking agents, two lubricants, and capsule shell material in four colors.

TABLE 9

Excipients Employed During Compatibility Study

| Functionality | Excipient | Manufacturer (Trade Name) | Grade | Description |
|---|---|---|---|---|
| Filling Agent | Mannitol | Roquette (Pearlitol 300DC | NF | Simple Organic Diluent |
| Diluent | Partially Pregelatinized Corn Starch | Colorcon (Starch 1500) | USP/NF | Complex Organic Diluent |
| | Silicified Microcrystalline Cellulose | JRS Pharma PROSOLV HD90) | USP | Complex Organic/inorganic Co-processed Diluent |
| | Anhydrous Dicalcium Phosphate | Innophos (A-Tab) | USP | Inorganic diluent |
| Glidant | Colloidal Silicon Dioxide | Cabot (Cab-O-Sil M5P) | USP | Glidant/ Anticaking Agent |
| | Talc | Ultra Chemicals (Ultra Talc 4000) | USP | Glidant/ Anticaking Agent |
| Lubricants | Magnesium Stearate (vegetable source) | Mallinckrodt | USP | Lubricant |
| | Sodium Stearyl Fumarate | JRS Pharma (Pruv) | USP | Lubricant |
| Capsule Shell | Clear Opaque HPMC Capsule Shell | Capsugel (V-Caps) | | Vegetable Source Capsule Shell |
| | White Opaque HPMC Capsule Shell | Capsugel (V-Caps) | | Vegetable Source Capsule Shell |
| | Blue Opaque HPMC Capsule Shell | Capsugel (V-Caps) | | Vegetable Source Capsule Shell |

A. Excipients

1. Filling Agents

Filling Agents were evaluated. Mannitol was evaluated as a simple organic filling agent as it has low hygroscopicity.

2. Diluents

Diluents representing three chemical categories were evaluated: complex organic, inorganic, and combination co-processed complex organic/inorganic (e.g., super-excipient). Microcrystalline cellulose was evaluated as PROSOLV HD90 as the co-processed Prosolv form can impart favorable processability even at low levels in the formulation. Starch 1500 was evaluated as it performs the multiple functions of imparting better flow and lubricity as well as being particularly effective with moisture sensitive actives and low dose geometric blending applications: A-Tab, an anhydrous inorganic excipient, was evaluated for possibly providing protection against moisture sorption.

3. Glidants

Cab-O-Sil (colloidal silicon dioxide) was included in the formulation evaluation as a potential glidant/anticaking agent. Due to its small particle size and large specific surface area, colloidal silicon dioxide is known for flow enhancement capabilities and moisture sequestering ability. Talc (USP) was included in the formulation evaluation as an alternative to Cab-O-Sil due to having similar glidant/anticaking properties to colloidal silicon dioxide.

4. Lubricants

Magnesium stearate and sodium stearyl fumarate (e.g., PRUV) were both evaluated as lubricants in the formulation evaluation. Magnesium stearate is the most commonly used lubricant in the pharmaceutical industry but, in some instances, can be susceptible to non-compatibility with various drug molecules and, in some instances, can be susceptible to "over-blending" which can affect release rate. PRUV was also evaluated in this study. PRUV can circumvent problems such as non-compatibility and over lubrication which can increase the hydrophobicity of the blended material. Thus, the bioavailability of certain actives may be improved by using PRUV as the lubricant.

5. Capsule Shell

Hydroxypropyl Methyl Cellulose (HPMC) capsule shells were selected for evaluation in this formulation study. HPMC capsule shells are known to reduce the risk of protein/protein interactions between gelatin capsule shells and the "active" egg proteins. The compatibility study was performed with ground HPMC colored capsule shells, using the natural, white and blue shells in the final product. Sample matrices were prepared, representing the three capsule shell colors, at a 10:1 (egg white powder: ground capsule shell) ratio.

B. Formulations

Sixteen formulation matrices were evaluated (including a control with egg white protein only) and as shown in Table 10. As content uniformity can be a challenge in formulations that contain extremely low levels of one or more ingredients, a geometric blending technique was used to ensure the low level ingredient was evenly distributed through the blends.

TABLE 10

| Blend Formulations | | | | | | | | | | | | | | |
|---|---|---|---|---|---|---|---|---|---|---|---|---|---|---|
| Excipient Name | 1 | 2 | 3 | 4 | 5 | 6 | 7 | 8 | 9 | 10 | 11 | 12 | 13 | 14 |
| Egg White Powder[1] | 6.0 | 3.0 | 3.0 | 3.0 | 6.0 | 6.0 | 6.0 | 6.0 | 6.0 | 6.0 | 6.0 | 3.0 | 3.0 | 3.0 |
| Pearlitol 300DC | | 3.0 | | | | | | | | | | 3.0 | | |
| PROSOLV HD90 | | | 3.0 | | | | | | | | | | | 3.0 |
| Starch 1500 | | | | 3.0 | | | | | | | | | 3.0 | |
| Cab-O-Sil | | | | | 0.6 | | | | | | | 0.3 | 0.3 | |
| Talc | | | | | | 0.6 | | | | | | | | |
| Magnesium Stearate | | | | | | | 0.6 | | | | | 0.3 | 0.3 | 0.3 |
| Pruv | | | | | | | | 0.6 | | | | | | |
| Natural capsule shells | | | | | | | | | 0.6 | | | 0.3 | | |
| White capsule shells | | | | | | | | | | 0.6 | | | 0.3 | |
| Blue capsule shells | | | | | | | | | | | 0.6 | | | 0.3 |
| Totals | 6.0 | 6.0 | 6.0 | 6.0 | 6.6 | 6.6 | 6.6 | 6.6 | 6.6 | 6.6 | 6.6 | 6.9 | 6.9 | 6.6 |

[1]Formulation 1 contains only egg white protein as the control in this study.
Note:
Formulations 2-8 contain egg white protein at ratios of 1:1 or 10:1 to the excipients.
Formulations 9-11 contain egg white protein at a ratio of 10:1 to the capsule shell material.
Formulations 12-13 contained blends of egg white powder, excipient, Cab-O-Sil, magnesium stearate and capsule shell material at a ratio of 10:10:1:1:1.
Formulation 14 contained a blend of egg white powder, excipient, magnesium stearate and capsule shell material at a ratio of 10:10:1:1.

C. Process/Manufacturing

For each Egg white powder/Excipient ratio evaluated, micro-blends of approximately 6 grams were prepared for evaluation at controlled storage conditions. The sample matrices were used to determine acceptable formulation excipients, which can then be utilized in a common place manufacturing process.

1. Procedure: Sample Preparation and Analysis
  1. Each of the formulation prototypes in Table 10 were blended in a vial or in a mortar and pestle for approximately 10 minutes.
  2. Each of the micro-blends were then placed in clear, borosilicate glass vials with Teflon lined screw-cap for "packaging" the sample preparations.
  3. Samples were stored at 40° C./75% Relative Humidity storage conditions.
  4. Stability samples were tested chemically and for appearance at time-zero, two-weeks, one-month, two-months and three-months. Evaluation of appearance involved the color of the powder, texture and determination of whether the material is cohesive or free flowing.
  5: Biochemical analysis of the stability samples were performed via HPLC analysis. Compatibility of the active material with the individual excipients was established if no significant changes in chromatography were seen between dry egg protein/excipient blends and dry egg protein which was not exposed to excipient. A sample of approximately 1.0 g was used for chemical analysis.
  6. Loss on Drying was evaluated for the initial (T=O) sample and at two months. A sample of approximately 2 g was used for LOD testing. The sample was heated to below its melting point and the moisture content (loss of water) measured.

D. Results Following 3-Month Excipient Compatibility Study

Results of the 3 month excipient compatibility study is presented herein. The study followed the parameters as set out above and formulation samples were stored at 40° C./75% Relative Humidity.

As presented above in Table 10, blend formulations were evaluated over a 3 month time period for a number of stability characteristics. Protein integrity over time, as assessed by size exclusion chromatography, is presented in Table 11 (% Area for each protein peak) at 5 time points.

TABLE 11

Protein Integrity (reported data, excludes placebo peaks)
Assay Results (Reported as percent area by peak)

| Sample # | Time Point | Peak # 1 | Peak # 2 | Peak # 3 | Peak # 4 | Peak # 5 |
|---|---|---|---|---|---|---|
| 1 | T = 0 | 8.50 | 9.91 | 10.83 | 66.68 | 4.08 |
|   | 2 W | 9.99 | 11.07 | 10.56 | 66.89 | 1.49 |
|   | 1 M | 10.30 | 11.14 | 10.17 | 63.71 | 4.67 |
|   | 2 M | 14.85 | 14.20 | 10.44 | 60.51 |  |
|   | 3 M | 15.03 | 13.27 | 9.53 | 62.17 |  |
| 2 | T = 0 | 9.30 | 9.92 | 10.71 | 66.14 | 3.93 |
|   | 2 W | 10.28 | 10.93 | 10.58 | 66.79 | 1.41 |
|   | 1 M | 11.25 | 11.15 | 10.17 | 62.71 | 4.73 |
|   | 2 M | 12.70 | 12.88 | 9.53 | 64.88 |  |
|   | 3 M | 14.74 | 13.16 | 9.33 | 62.77 |  |
| 3 | T = 0 | 8.55 | 9.91 | 10.74 | 66.87 | 3.91 |
|   | 2 W | 10.36 | 11.06 | 10.59 | 66.72 | 1.27 |
|   | 1 M | 11.01 | 11.25 | 10.05 | 63.12 | 4.57 |
|   | 2 M | 13.36 | 12.98 | 9.64 | 64.02 |  |
|   | 3 M | 14.71 | 13.02 | 9.50 | 62.77 |  |
| 4 | T = 0 | 8.58 | 9.89 | 10.70 | 66.89 | 3.95 |
|   | 2 W | 10.30 | 11.15 | 10.53 | 66.87 | 1.14 |
|   | 1 M | 10.06 | 10.98 | 10.00 | 64.22 | 4.75 |
|   | 2 M | 13.31 | 12.91 | 9.70 | 64.09 |  |
|   | 3 M | 13.40 | 12.83 | 9.62 | 64.15 |  |
| 5 | T = 0 | 8.36 | 9.89 | 10.48 | 67.40 | 3.86 |
|   | 2 W | 9.54 | 10.74 | 10.60 | 68.08 | 1.04 |
|   | 1 M | 9.42 | 10.71 | 10.22 | 65.02 | 4.64 |
|   | 2 M | 12.72 | 12.82 | 9.82 | 64.64 |  |
|   | 3 M | 14.04 | 13.09 | 9.66 | 63.21 |  |
| 6 | T = 0 | 8.66 | 9.86 | 10.79 | 66.76 | 3.93 |
|   | 2 W | 9.39 | 10.67 | 10.78 | 68.15 | 1.00 |
|   | 1 M | 9.25 | 10.70 | 10.29 | 65.12 | 4.63 |
|   | 2 M | 13.06 | 12.75 | 9.87 | 64.32 |  |
|   | 3 M | 14.02 | 13.00 | 9.65 | 63.33 |  |

TABLE 11-continued

Protein Integrity (reported data, excludes placebo peaks)
Assay Results (Reported as percent area by peak)

| Sample # | Time Point | Peak # 1 | Peak # 2 | Peak # 3 | Peak # 4 | Peak # 5 |
|---|---|---|---|---|---|---|
| 7 | T = 0 | 8.66 | 9.86 | 10.75 | 66.80 | 3.92 |
|   | 2 W | 9.34 | 10.64 | 10.87 | 68.23 | 0.91 |
|   | 1 M | 8.80 | 10.36 | 10.50 | 65.80 | 4.54 |
|   | 2 M | 11.96 | 12.17 | 10.23 | 65.64 | |
|   | 3 M | 12.35 | 12.70 | 10.00 | 64.94 | |
| 8 | T = 0 | 8.34 | 9.81 | 10.77 | 67.09 | 3.99 |
|   | 2 W | 8.95 | 10.50 | 10.83 | 68.82 | 0.90 |
|   | 1 M | 8.94 | 10.30 | 10.53 | 65.72 | 4.52 |
|   | 2 M | 11.57 | 12.25 | 10.20 | 65.98 | |
|   | 3 M | 12.23 | 12.57 | 9.96 | 65.24 | |
| 9 | T = 0 | 8.74 | 9.80 | 10.93 | 66.47 | 4.06 |
|   | 2 W | 9.60 | 10.68 | 10.89 | 68.04 | 0.79 |
|   | 1 M | 9.88 | 10.58 | 10.49 | 64.51 | 4.54 |
|   | 2 M | 12.59 | 12.55 | 10.02 | 64.84 | |
|   | 3 M | 13.04 | 12.90 | 9.84 | 64.21 | |
| 10 | T = 0 | 8.94 | 9.88 | 10.78 | 66.43 | 3.97 |
|    | 2 W | 9.51 | 10.77 | 10.92 | 68.09 | 0.72 |
|    | 1 M | 8.77 | 10.35 | 10.29 | 65.80 | 4.79 |
|    | 2 M | 12.78 | 12.71 | 10.02 | 64.50 | |
|    | 3 M | 13.56 | 12.89 | 9.84 | 63.70 | |
| 11 | T = 0 | 8.97 | 9.88 | 10.78 | 66.41 | 3.96 |
|    | 2 W | 9.72 | 10.77 | 10.88 | 67.98 | 0.64 |
|    | 1 M | 10.32 | 10.90 | 10.44 | 63.83 | 4.51 |
|    | 2 M | 13.21 | 12.83 | 9.86 | 64.10 | |
|    | 3 M | 13.00 | 12.92 | 9.73 | 64.35 | |
| 12 | T = 0 | 9.32 | 10.02 | 10.41 | 66.41 | 3.84 |
|    | 2 W | 8.34 | 10.80 | 10.33 | 70.05 | 0.47 |
|    | 1 M | 6.71 | 10.34 | 9.74 | 68.35 | 4.87 |
|    | 2 M | 13.61 | 13.03 | 9.32 | 64.04 | |
|    | 3 M | 13.09 | 12.97 | 9.00 | 64.94 | |
| 13 | T = 0 | 8.22 | 9.96 | 10.22 | 67.83 | 3.78 |
|    | 2 W | 9.22 | 11.07 | 10.39 | 68.89 | 0.43 |
|    | 1M | 9.98 | 11.09 | 10.04 | 64.41 | 4.48 |
|    | 2M | 13.49 | 13.00 | 9.45 | 64.06 | |
|    | 3M | 13.51 | 13.37 | 9.75 | 63.36 | |
| 14 | T = 0 | 7.99 | 9.73 | 10.80 | 67.56 | 3.91 |
|    | 2 W | 9.31 | 10.98 | 10.72 | 68.57 | 0.40 |
|    | 1 M | 9.23 | 10.68 | 10.25 | 65.33 | 4.51 |
|    | 2 M | 13.15 | 12.84 | 9.81 | 64.20 | |
|    | 3 M | 14.16 | 13.01 | 9.51 | 63.32 | |

At T=0, Σ4-6=98.07. Range of acceptability is +/−2% of initial, giving range of 96.11-100.03. Σ4-6 for all samples fall within this range.

Appearance observations include color, texture and flowability. Loss on Drying was tested at T=0 and at the 2 month time point. Appearance and Loss on Drying data are presented in Table 12.

TABLE 12

Appearance and Loss on Drying

| Sample # | Time | Color | Texture | Cohesive or Free-flowing | % LOD | Δ LOD |
|---|---|---|---|---|---|---|
| 1 | T = 0 | off white | fine powder | cohesive | 9.9 | |
|   | 1 M | off white | fine powder | cohesive | | |
|   | 2 M | off white | fine powder | cohesive | 11.92 | 2.02 |
|   | 3 M | off white | fine powder | cohesive | | |
| 2 | T = 0 | off white | fine powder | cohesive | 4.3 | |
|   | 1 M | off white | fine powder | cohesive | | |
|   | 2 M | off white | fine powder | cohesive | 6.82 | 2.52 |
|   | 3 M | off white | fine powder | cohesive | | |
| 3 | T = 0 | off white | fine powder | cohesive | 6.2 | |
|   | 1 M | off white | fine powder | cohesive | | |
|   | 2 M | off white | fine powder | cohesive | 9.00 | 2.80 |
|   | 3 M | off white | fine powder | cohesive | | |
| 4 | T = 0 | off white | fine powder | cohesive | 9.3 | |
|   | 1 M | off white | fine powder | cohesive | | |
|   | 2 M | off white | fine powder | cohesive | 11.47 | 2.17 |
|   | 3 M | off white | fine powder | cohesive | | |
| 5 | T = 0 | off white | fine powder | cohesive | 7.5 | |
|   | 1 M | off white | fine powder | cohesive | | |
|   | 2 M | off white | fine powder | cohesive | 10.95 | 3.45 |
|   | 3 M | off white powder largewhiteclump | fine powder with large white clumps | cohesive | | |
| 6 | T = 0 | off white | fine powder | free flowing | 7.2 | |
|   | 1 M | off white | fine powder | free flowing | | |
|   | 2 M | off white | fine powder | free flowing | 11.00 | 3.80 |
|   | 3 M | off white | fine powder | cohesive | | |
| 7 | T = 0 | off white | fine powder | cohesive | 7.6 | |
|   | 1 M | off white | fine powder | cohesive | | |
|   | 2 M | off white | fine powder | cohesive | 9.56 | 1.96 |
|   | 3 M | off white | fine powder | cohesive | | |
| 8 | T = 0 | off white | fine powder | cohesive | 7.4 | |
|   | 1 M | off white | fine powder | cohesive | | |
|   | 2 M | off white | fine powder | cohesive | 8.98 | 1.58 |
|   | 3 M | off white | fine powder | cohesive | | |
| 9 | T = 0 | off white | fine powder w/visible flecks | cohesive | 8.1 | |
|   | 1 M | off white | fine powder w/visible flecks | cohesive | | |

TABLE 12-continued

Appearance and Loss on Drying

| Sample # | Time | Color | Texture | Cohesive or Free-flowing | % LOD | Δ LOD |
|---|---|---|---|---|---|---|
| | 2 M | off white | fine powder w/visible flecks | cohesive | 10.20 | 2.10 |
| | 3 M | off white | fine powder w/visible flecks | cohesive | | |
| 10 | T = 0 | off white | fine powder w/visible flecks | cohesive | 8.4 | |
| | 1 M | off white | fine powder w/visible flecks | cohesive | | |
| | 2 M | off white | fine powder w/visible flecks | cohesive | 10.85 | 2.45 |
| | 3 M | off white | fine powder w/visible flecks | cohesive | | |
| 11 | T = 0 | off white w/blue specks | fine powder w/visible flecks | cohesive | 9.0 | |
| | 1 M | off white w/blue specks | fine powder w/visible flecks | cohesive | | |
| | 2 M | off white w/blue specks | fine powder w/visible flecks | cohesive | 11.16 | 2.16 |
| | 3 M | off white w/ blue specks | fine powder w/visible flecks | cohesive | | |
| 12 | T = 0 | off white | fine powder | free flowing | 5.8 | |
| | 1 M | off white | fine powder | free flowing | | |
| | 2 M | off white | fine powder | free flowing | 5.92 | 0.12 |
| | 3 M | off white | fine powder w/visible flecks | free flowing | | |
| 13 | T = 0 | off white | fine powder | free flowing | 8.6 | |
| | 1 M | off white | fine powder | free flowing | | |
| | 2 M | off white | fine powder | free flowing | 10.48 | 1.88 |
| | 3 M | off white with smallwhiteclump | fine powder small white clumps | free flowing | | |
| 14 | T = 0 | off white w/ blue specks | fine powder w/visible flecks | free flowing | 6.8 | |
| | 1 M | off white w/blue specks | fine powder w/visible flecks | free flowing | | |
| | 2 M | off white w/ blue specks | fine powder w/visible flecks | free flowing | 8.15 | 1.35 |
| | 3 M | off white w/blue specks | fine powder w/visible flecks | free flowing | | |

As shown in Table 12, three blends (12-14) were free-flowing after 3 months. The results show that at 75% relative humidity, the egg protein formulations (blends 12-14) take up less moisture than egg white protein alone Example 5: Egg Protein Formulations Based on the compatibility study results in Example 4, the formulations shown in Tables 13-16 were made and tested as exemplary formulations. ProSolv SMCC 50 and ProSolv HD90 were included as diluents, Mannitol was included as a filling agent, Magnesium Stearate was included as a lubricant. However, other diluents, filling agents and lubricants can be used with comparable results. Example 6 provides the results of fill and recovery testing for the exemplary formulations.

TABLE 13

Formulation for 0.2 mg capsules

| Item # | Ingredient | % w/w | mg/ dose |
|---|---|---|---|
| 1 | EWP Pre-blend Lot 14004 (1.78% protein) | 7.15 | 11.3 |
| 2 | ProSolv SMCC 50 | 36.58 | 57.8 |
| 3 | ProSolv HD90 | 45.76 | 72.3 |

TABLE 13-continued

Formulation for 0.2 mg capsules

| Item # | Ingredient | % w/w | mg/ dose |
|---|---|---|---|
| 4 | Mannitol 200SD | 10.00 | 15.8 |
| 5 | Magnesium Stearate | 0.50 | 0.79 |
| | total | 100 | 158 |

TABLE 14

Formulation for 1.0 mg capsules

| Item # | Ingredient | % w/w | mg/dose |
|---|---|---|---|
| 1 | EWP Preblend Lot 14008 (1.86% Protein) | 35.85 | 53.77 |
| 2 | Prosolv SMCC 50 | 26.15 | 39.23 |
| 3 | Prosolv HD90 | 27.51 | 41.26 |
| 4 | Mannitol 200 SD | 10.0 | 15.0 |
| 5 | Magnesium Stearate | 0.5 | 0.75 |
| | Total | 100 | 150 |

TABLE 15

Formulation for 10.0 mg capsules

| Item | Ingredient | % w/w | mg/dose |
|---|---|---|---|
| 1 | Egg White Powder (81.85% protein) | 2.57 | 12.2(10.0) |
| 2 | ProSolv SMCC 50 | 38.46 | 182.7 |
| 3 | ProSolv HD90 | 48.47 | 230.2 |
| 4 | Mannitol 200SD | 10.00 | 47.5 |
| 5 | Magnesium Stearate | 0.50 | 2.4 |
| | Total | 100 | 475 |

TABLE 16

Formulation for 100.0 mg capsules

| Item # | Ingredient | % w/w | mg/dose |
|---|---|---|---|
| 1 | Egg White Powder (81.85% protein) | 25.73 | 122.2(100.0) |
| 2 | ProSolv SMCC 50 | 28.21 | 134.0 |
| 3 | ProSolv HD90 | 35.56 | 168.9 |
| 4 | Mannitol 200SD | 10.00 | 47.5 |
| 5 | Magnesium Stearate | 0.50 | 2.4 |
| | Total | 100 | 475 |

Example 6: Fill and Recovery Analyses

The formulations in Tables 13-16 were tested for fill and recovery when formulated in a capsule. The capsule fill and recovery was evaluated for 4 dosage strengths of egg white protein: 0.2 mg, 1.0 mg, 10.0 mg and 100.0 mg. For each dosage strength, 100 capsules were made using the Pro-Fill® hand encapsulation unit. The acceptance range for each set of capsules was ±3% of the target fill weight from the formulation. All capsules used were weight-checked to ensure they were within the acceptance range. Recovery data is presented in Tables 17-20 for 0.2, 1.0, 10.0 and 100.0 mg capsules, respectively.

TABLE 17

Fill Recovery 0.2 mg Capsules

| Capsule # | Total Weight of Capsule (mg) | Fill Mass Recovered per capsule (mg) | Weight of Empty Shell (mg) | % Recovery per capsule |
|---|---|---|---|---|
| 1 | 209 | 157 | 49 | 98.1 |
| 2 | 203 | 151 | 50 | 98.7 |
| 3 | 204 | 155 | 48 | 99.4 |
| 4 | 202 | 151 | 48 | 98.1 |
| 5 | 204 | 152 | 51 | 99.3 |
| 6 | 204 | 152 | 51 | 99.3 |
| 7 | 207 | 154 | 50 | 98.1 |
| 8 | 201 | 153 | 48 | 100.0 |
| 9 | 201 | 150 | 50 | 99.3 |
| 10 | 203 | 154 | 47 | 98.7 |
| Avg | 203.8 | 152.9 | 49.2 | 98.9 |
| SD | 2.5 | 2.1 | 1.4 | 0.7 |
| RSD | 1.2 | 1.4 | 2.8 | 0.7 |
| Target (mg): | | 158 | | |
| Average Fill Mass Recovered as % of Target | | 96.8 | | |

TABLE 18

Fill Recovery 1.0 mg Capsules

| Capsule # | Total Weight of Capsule (mg) | Fill Mass Recovered per capsule (mg) | Weight of Empty Shell (mg) | % Recovery per capsule |
|---|---|---|---|---|
| 1 | 191 | 146 | 44 | 99.3 |
| 2 | 191 | 143 | 47 | 99.3 |
| 3 | 192 | 145 | 45 | 98.6 |
| 4 | 192 | 146 | 44 | 98.6 |
| 5 | 193 | 146 | 45 | 98.6 |
| 6 | 191 | 144 | 44 | 98.0 |
| 7 | 191 | 146 | 44 | 99.3 |
| 8 | 191 | 143 | 46 | 98.6 |
| 9 | 191 | 143 | 45 | 97.9 |
| 10 | 191 | 145 | 45 | 99.3 |
| Avg | 191.4 | 144.7 | 44.9 | 98.8 |
| SD | 0.7 | 1.3 | 1.0 | 0.5 |
| RSD | 0.4 | 0.9 | 2.2 | 0.5 |
| Target (mg): | | 150 | | |
| Average Fill Mass Recovered as % of Target | | 96.5 | | |

TABLE 19

Fill Recovery 10.0 mg Capsules

| Capsule # | Total Weight of Capsule (mg) | Fill Mass Recovered per capsule (mg) | Weight of Empty Shell (mg) | % Recovery per capsule |
|---|---|---|---|---|
| 1 | 598 | 470 | 126 | 99.6 |
| 2 | 589 | 463 | 124 | 99.6 |
| 3 | 587 | 459 | 126 | 99.6 |
| 4 | 594 | 465 | 128 | 99.8 |
| 5 | 599 | 472 | 125 | 99.6 |
| 6 | 599 | 469 | 128 | 99.6 |
| 7 | 589 | 463 | 126 | 100.0 |
| 8 | 588 | 459 | 128 | 99.8 |
| 9 | 592 | 463 | 128 | 99.8 |
| 10 | 596 | 470 | 125 | 99.8 |
| Avg | 593.1 | 465.3 | 126.4 | 99.7 |
| SD | 4.7 | 4.7 | 1.5 | 0.1 |
| RSD | 0.8 | 1.0 | 1.2 | 0.1 |
| Target (mg): | | 475 | | |
| Average Fill Mass Recovered as % of Target | | 98.0 | | |

TABLE 20

Fill Recovery 100.0 mg Capsules

| Capsule # | Total Weight of Capsule (mg) | Fill Mass Recovered per capsule (mg) | Weight of Empty Shell (mg) | % Recovery per capsule |
|---|---|---|---|---|
| 1 | 592 | 463 | 123 | 98.7 |
| 2 | 599 | 469 | 128 | 99.6 |
| 3 | 591 | 465 | 122 | 99.1 |
| 4 | 588 | 463 | 123 | 99.6 |
| 5 | 601 | 474 | 123 | 99.2 |
| 6 | 597 | 472 | 121 | 99.2 |
| 7 | 586 | 462 | 121 | 99.4 |
| 8 | 598 | 474 | 122 | 99.6 |
| 9 | 587 | 453 | 132 | 99.6 |
| 10 | 584 | 460 | 121 | 99.4 |
| Avg | 592.3 | 465.5 | 123.6 | 99.3 |
| SD | 6.1 | 6.8 | 3.6 | 0.3 |
| RSD | 1.0 | 1.5 | 2.9 | 0.3 |
| Target (mg): | | 475 | | |
| Average Fill Mass Recovered as % of Target | | 98 | | |

The recovery of the material from the capsules for the formulations for the 0.2 mg, 1.0 mg, 10.0 mg, and 100.0 mg capsules was between 98 and 100% for all capsules tested. This shows that the formulations provided in Tables 13-16 can be used effectively for the production of capsulized pharmaceuticals containing egg white proteins.

Example 7: Blend and Content Uniformity Analyses

Blend and content uniformity analyses were conducted on formulations based on those in Tables 13-16 as follows: The common egg white protein powder (EWP) pre-blend shown in Table 21 was created using Michael Foods EWP, lot 1248944. The common blend was then diluted to give three dosage strengths (0.2 mg, 1.0 mg, and 10.0 mg). Geometric dilutions were used in the common blend as well as the dilutions for the 0.2 mg and 1.0 mg dosage strengths. Geometric dilution or geometric blending is a technique used in mixing two ingredients of unequal quantities; one begins with the smallest quantity and adds an equal quantity of the ingredient having the larger amount. The process then continues until all of the ingredients are used.

TABLE 21

Common Pre-blend Formulation
Formulation for Batch 054-MFG-14008 (Common Pre-blend)

| Item No. | Ingredient | Concentration (% w/w) | Amount/Batch (g) |
|---|---|---|---|
| 1 | Egg White Protein (Powder) | *1.78(2.18) | 32.12(39.24) |
| 2 | Prosolv SMCC 50 | 43.04 | 774.76 |
| 3 | Prosolv HD90 | 54.78 | 986.00 |
| | Total | 100 | 1800 |

*Based on egg white protein powder containing 81.85% protein. (Blend was originally formulated based on EWP containing 85.71% protein, which would have given the pre-blend a protein concentration of 1.86%. The tables have been adjusted to reflect the actual protein content.)

The "use as" protein content of Michael Foods EWP was found, to be 81.85%. Because this information was not available at the time of blending, the original formulations were based on the slightly higher protein content of the Deb El material, 85.71%. All formulations were adjusted to reflect the Michael Food values. The adjusted formulations for all batches are shown in Tables 22-24.

TABLE 22

Formulation for Batch 054-MFG-14009A (0.2*/0.19 mg** Protein)

| Item No. | Ingredient | Concentration (% w/w) | mg/Dose | Adjusted mg/Dose) | Amount/Batch (g) |
|---|---|---|---|---|---|
| 1 | EWP Pre-blend Lot 14008(*1.86% protein/**1.78% protein) | 7.17 | *10.75 (0.2 mg) | **10.75 (0.19 mg) | 107.55 |
| 2 | ProSolv SMCC 50 | 36.60 | 54.90 | 54.90 | 549.00 |
| 3 | ProSolv HD90 | 45.73 | 68.60 | 68.60 | 685.95 |
| 4 | Mannitol 200SD | 10.00 | 15.00 | 15.00 | 150.00 |
| 5 | Magnesium Stearate | 0.50 | 0.75 | 0.75 | 7.50 |
| | Total | 100 | 150 | 150 | 1500 |

*Based on egg white powder containing 85.71% protein.
**Based on egg white powder containing 81.85% protein.
(Blend was originally formulated based on EWP containing 85.71% protein and pre-blend concentration of 1.86% to give 0.2 mg protein per dose. The adjusted column in the tables reflects the actual protein content.)

TABLE 23

Formulation for Batch 054-MFG-14010B (1.0*/0.96 mg** Protein)

| Item No. | Ingredient | Concentration | mg/Dose | Adjusted | Amount/ |
|---|---|---|---|---|---|
| 1 | EWP Pre-blend Lot 14008(*1.86% protein/**1.78% protein) | 35.85 | *53.77 (1.0 mg) | **53.77 (0.96 mg) | 537.7 |
| 2 | ProSolv SMCC 50 | 26.15 | 39.23 | 39.23 | 392.2 |
| 3 | ProSolv HD90 | 27.51 | 41.26 | 41.26 | 412.6 |
| 4 | Mannitol 200SD | 10.0 | 15.0 | 15.0 | 150.0 |
| 5 | Magnesium Stearate | 0.5 | 0.75 | 0.75 | 7.5 |
| | Total | 100 | 150 | 150 | 1500 |

*Based on egg white powder containing 85.71% protein.
**Based on egg white powder containing 81.85% protein.
(Blend was originally formulated based on EWP containing 85.71% protein and pre-blend concentration of 1.86% to give 1.0 mg protein per dose. The adjusted column in the tables reflects the actual protein content.)

TABLE 24

Formulation for Batch 054-MFG-14011C (10.0*/9.55 mg** Protein)

| Item | Ingredient | Concentration | mg/Dose | Adjusted | Amount/ |
|---|---|---|---|---|---|
| 1 | EWP Pre-blend Lot 14008(*1.86% protein/**1.78% protein) | 89.6 | *537.7 (10.0 mg) | **537.7 (9.55 mg) | 474.9 |

TABLE 24-continued

Formulation for Batch 054-MFG-14011C (10.0*/9.55 mg** Protein)

| Item | Ingredient | Concentration | mg/Dose | Adjusted | Amount/ |
|---|---|---|---|---|---|
| 2 | Mannitol 200SD | 10.0 | 60.0 | 60.0 | 53.0 |
| 3 | Magnesium Stearate | 0.4 | 2.3 | 2.3 | 2.1 |
|  | Total | 100 | 600 | 600 | 530 |

*Based on egg white powder containing 85.71% protein.
**Based on egg white powder containing 81.85% protein.
(Blend was originally formulated based on EWP containing 85.71% protein and pre-blend concentration of 1.86% to give 10.0 mg protein per dose. The adjusted column in the tables reflects the actual protein content.) Blend was less dense than anticipated and did not till at target weight. Label claim was adjusted for this batch. (Target fill weight was 600 mg. Actual fill weight was 478 mg. Adjusted label claim was 8 mg.)

All blends were thieved for blend uniformity testing. Blend uniformity measures the uniformity of the blending method. It is important that the active ingredient(s) are uniformly blended in the formulation, A 1.0 cc sample thief was used to pull samples from 10 unique regions of the blender. The thieved samples were delivered directly into tared, labeled specimen cups. The weight of the sample was determined as the difference between the empty and filled cups. Analytical testing utilized the entire sample rather than a portion of the thieved material. Capsule shells were hand-filled using appropriately sized ProFill systems.

An analysis of egg protein content and blend uniformity was conducted using size exclusion chromatography as provided in Example 2. The calculations used to quantify the content uniformity, the blend uniformity, and the total protein (assay for egg white protein) from the chromatogram overlays are as follows:

Content Uniformity (% Label Claim)

$$\% \text{ Label Claim } (\% LC) = (R_U/R_S) \times C_{STD} \times (V_{SPL}/LC) \times 100, \text{ where:}$$

Ru=Area of Egg White Protein in the Sample
Rs=Average Egg White Protein Peak Area in all Standards
Cstd=Working Standard Concentration (mg/mL)
Vspl=Volume of Working Sample
LC=Label claim
100=Conversion factor to percentage Blend Uniformity (% Label Claim)

$$\% \text{ Label Claim } (\% LC) = (R_U/R_S) \times C_{STD} \times (V_{SPL}/Wt_{SPL}) \times (TCFW/LC) \times 100, \text{ where:}$$

$R_u$=Area of Egg White Protein in the Sample
$R_s$=Average Egg White Protein Peak Area in all Standards
$C_{std}$=Working Standard Concentration (mg/mL)
$V_{spl}$=Volume of Working Sample
$Wt_{spl}$=Weight of Working Sample
TCFW=Target Capsule Fill Weight
LC=Label claim
100=Conversion factor to percentage Assay for Egg White Protein $$\text{Assay} = (R_U/R_S) \times C_{STD} \times (V_{Sample}/Wt_{Sample}) \times (ACFW/LC) \times 100, \text{ where:}$$

Figure 22:
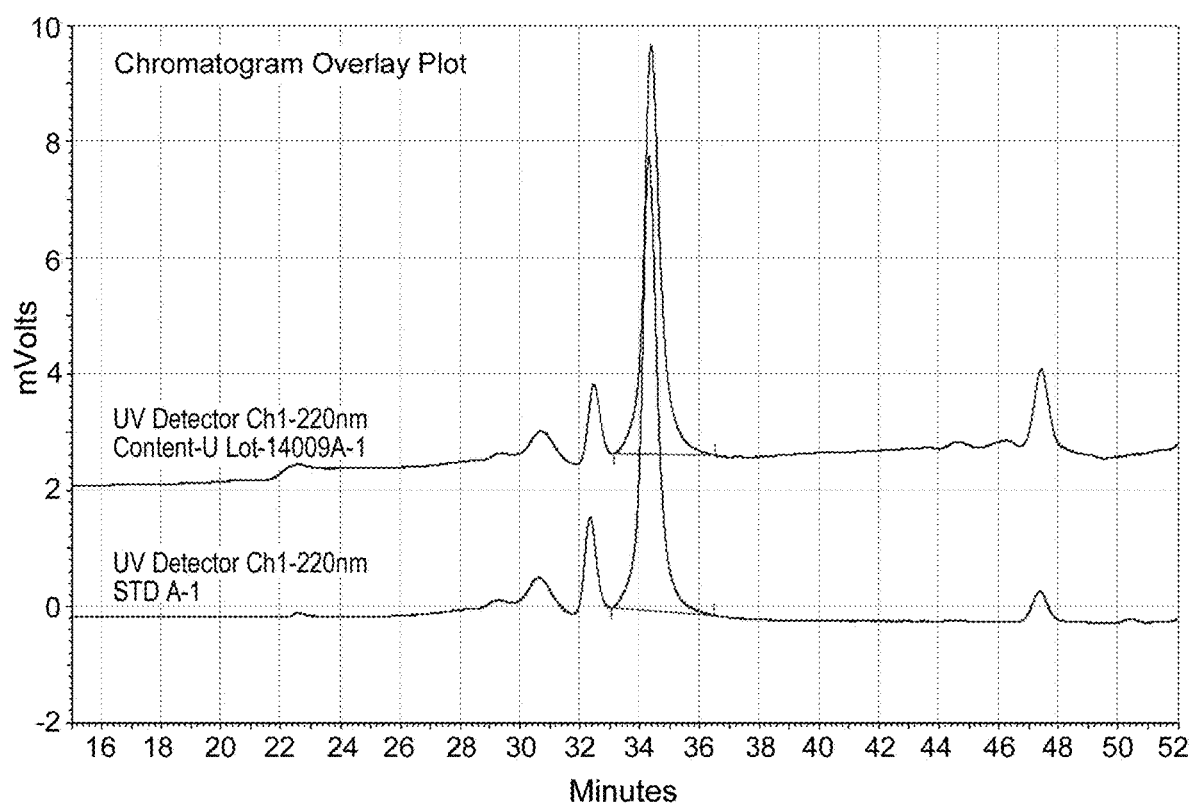
FIG. 22 is a chromatogram overlay of Egg White Protein Standard (bottom) and 0.2 mg Capsule Content Uniformity Sample, Lot #: 14009A-1 (top).
Figure 23:
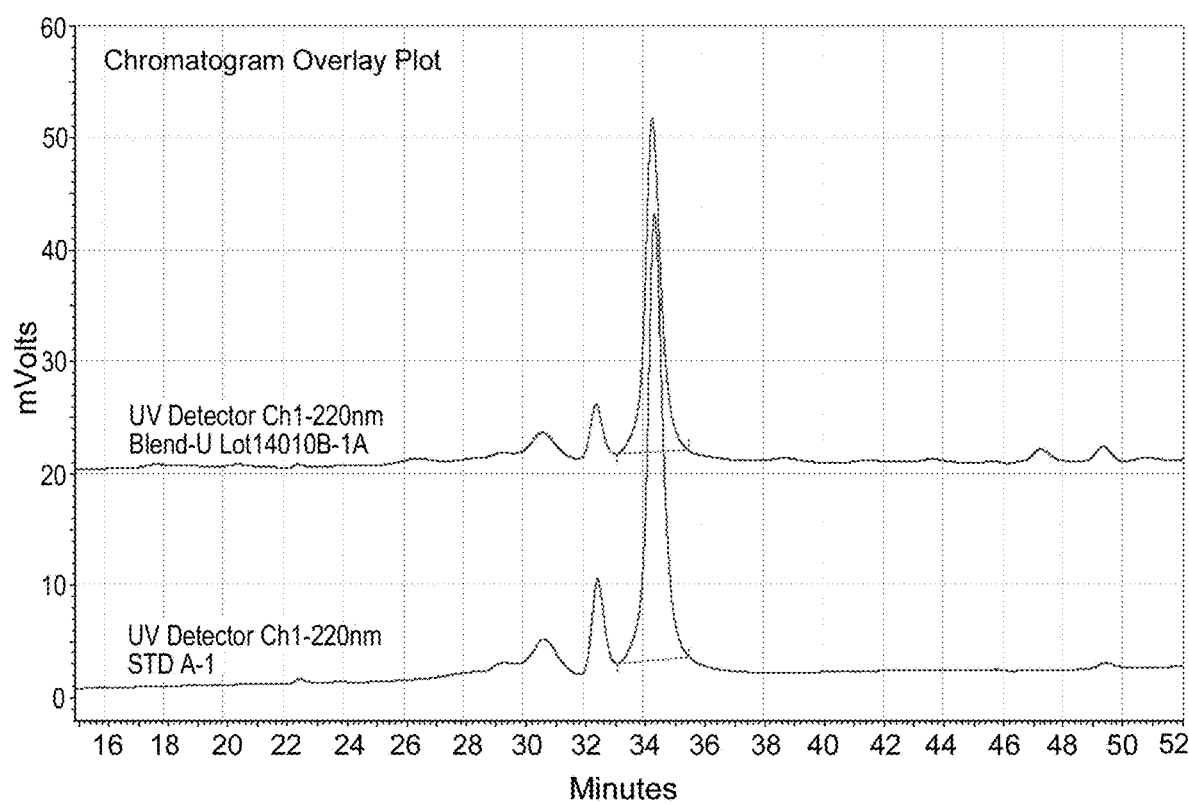
FIG. 23 is a chromatogram overlay of Egg White Protein Standard (bottom) and 1.0 mg Blend Uniformity Sample, Lot #: 14010B-1 (top) in accordance with aspects of the present technology.
Figure 24:
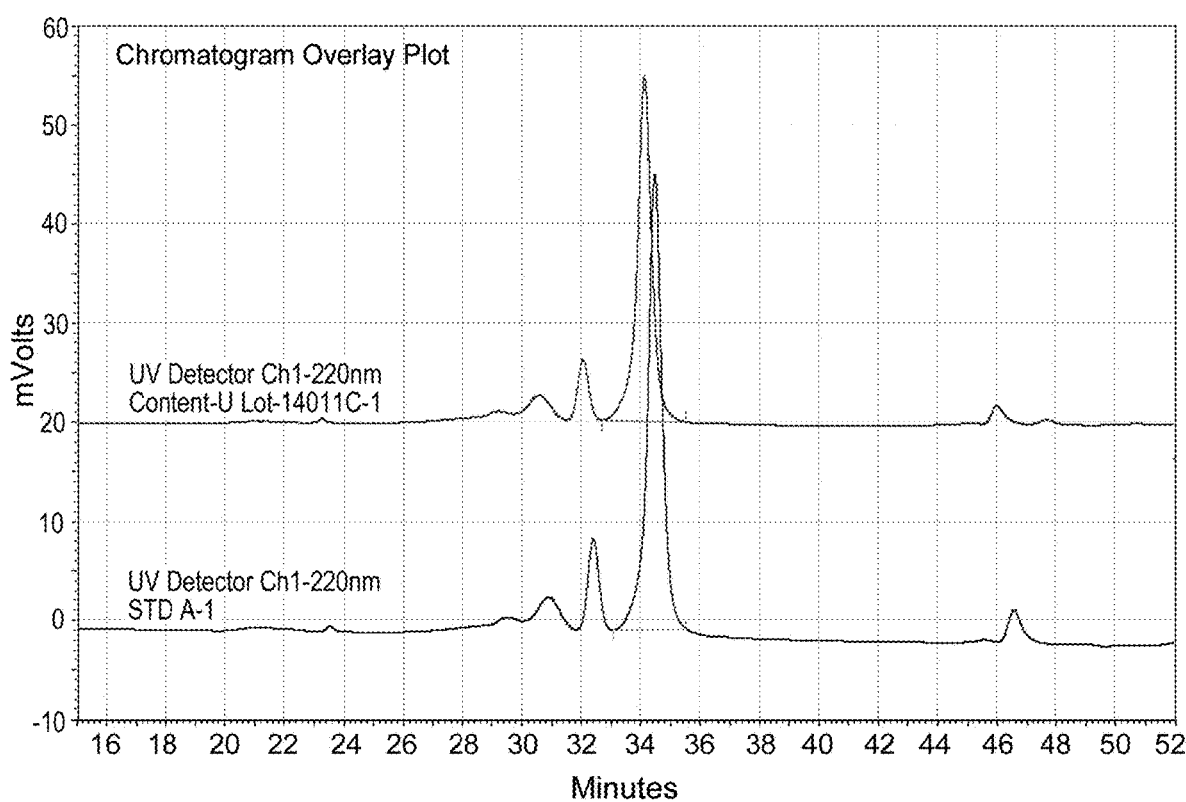
FIG. 24 is a chromatogram overlay of Egg White Protein Standard (bottom) and 10 mg Capsule Content Uniformity Sample, Lot #: 14011C-1 (top) in accordance with aspects of the present technology.

$R_u$=Area of Egg White Protein in the Sample
$R_s$=Average Egg White Protein Peak Area in all Standards
$C_{STD}$=Working Standard Concentration (mg/mL)
$V_{Sample}$=Volume of the Working Sample (mL)
$Wt_{Sample}$=Weight of Egg White Protein in the Sample (mg)
ACFW=Average Capsule Fill Weight
LC=Label claim
100=Conversion factor to percentage FIG. 22 shows the chromatogram overlay of egg white protein standard (bottom) and 0.2 mg capsule Content. Uniformity sample (top). FIG. 23 shows the chromatogram overlay of egg white protein standard (bottom) and 1.0 mg capsule Content Uniformity sample (top). FIG. 24 shows the chromatogram overlay of egg white protein standard (bottom) and 10.0 mg capsule content uniformity sample (top). Blend analysis data for all batches is presented in Tables 25-28. Uniformity of content is a pharmaceutical analysis technique for the quality control of capsules or tablets. Multiple capsules or tablets are selected at random and a suitable analytical method is applied to assay the individual content of the active ingredient in each capsule or tablet. The preparation complies if not more than one (all within limits) individual content is outside the limits of 85 to 115% of the average content and none is outside the limits of 75 to 125% of the average content. The results show that from a uniformity perspective, all of the Blends were acceptable with <~5% RSD.

Content uniformity and assay results for the filled capsules are presented in Tables 29-31. Content Uniformity was acceptable for the 0.2 mg and 1.0 mg capsules with RSD<~4%. However, content uniformity for the 10.0 mg capsules had an RSD of 8%. This is significantly more variability than the blend alone.

TABLE 25

Blend Analysis, Batch 054-MFG-14008 (Common Pre-blend)

| Sample | % Recovery | | |
|---|---|---|---|
| 1 | 94.84 | Mean | 96.37 |
| 2 | 103.72 | Std Dev | 3.15 |
| 3 | 96.56 | % RSD | 3.26 |
| 4 | 97.58 | | |
| 5 | 92.15 | | |
| 6 | 97.71 | | |
| 7 | 96.07 | | |
| 8 | 96.29 | | |
| 9 | 95.70 | | |
| 10 | 93.05 | | |

TABLE 26

Blend Analysis, Batch 054-MFG-14009A (0.2 mg)

| Sample | % Recovery | | |
|---|---|---|---|
| 1 | 81.91 | Mean | 80.91 |
| 2 | 80.59 | Std Dev | 1.69 |
| 3 | 82.08 | % RSD | 2.08 |
| 4 | 77.81 | | |
| 5 | 80.01 | | |
| 6 | 80.53 | | |

TABLE 26-continued

Blend Analysis, Batch 054-MFG-14009A (0.2 mg)

| Sample | % Recovery |
|---|---|
| 7 | 82.65 |
| 8 | 78.80 |
| 9 | 81.76 |
| 10 | 83.00 |

TABLE 27

Blend Analysis, Batch 054-MFG-14010B (1.0 mg)

| Sample | % Recovery | | |
|---|---|---|---|
| 1 | 95.07 | Mean | 89.65 |
| 2 | 93.32 | Std Dev | 3.68 |
| 3 | 88.75 | % RSD | 4.10 |
| 4 | 93.04 | | |
| 5 | 89.65 | | |
| 6 | 86.48 | | |
| 7 | 89.49 | | |
| 8 | 91.61 | | |
| 9 | 84.07 | | |
| 10 | 84.98 | | |

TABLE 28

Blend Analysis, Batch 054-MFG-14011C (10.0 mg)

| Sample | % Recovery | | |
|---|---|---|---|
| 1 | 90.11 | Mean | 88.63 |
| 2 | 89.83 | Std Dev | 4.58 |
| 3 | 88.62 | % RSD | 5.17 |
| 4 | 91.09 | | |
| 5 | 77.80 | | |
| 6 | 83.94 | | |
| 7 | 89.03 | | |
| 8 | 94.03 | | |
| 9 | 90.62 | | |
| 10 | 91.24 | | |

TABLE 29

Content Uniformity, Batch 054-MFG-14009A (0.2 mg)

| Sample | % Recovery | | |
|---|---|---|---|
| 1 | 99.53 | Mean | 93.80 |
| 2 | 90.28 | Std Dev | 3.99 |
| 3 | 92.84 | % RSD | 4.25 |
| 4 | 93.34 | | |
| 5 | 99.82 | | |
| 6 | 90.78 | | |
| 7 | 91.55 | | |
| 8 | 88.07 | | |
| 9 | 94.39 | | |
| 10 | 97.43 | | |
| Assay: 80.11% | | | |

TABLE 30

Content Uniformity, Batch 054-MFG-14010B (1.0 mg)

| Sample | % Recovery | | |
|---|---|---|---|
| 1 | 92.72 | Mean | 92.81 |
| 2 | 90.80 | Std Dev | 3.04 |
| 3 | 88.37 | % RSD | 3.28 |
| 4 | 96.02 | | |

TABLE 30-continued

Content Uniformity, Batch 054-MFG-14010B (1.0 mg)

| Sample | % Recovery |
|---|---|
| 5 | 97.55 |
| 6 | 91.98 |
| 7 | 95.52 |
| 8 | 90.50 |
| 9 | 89.78 |
| 10 | 94.89 |
| Assay: 99.69% | |

TABLE 31

Content Uniformity, Batch 054-MFG-14011C (10.0 mg)

| Sample | % Recovery | | |
|---|---|---|---|
| 1 | 99.40 | Mean | 98.66 |
| 2 | 105.59 | Std Dev | 7.83 |
| 3 | 102.57 | % RSD | 7.93 |
| 4 | 103.37 | | |
| 5 | 94.37 | | |
| 6 | 78.63 | | |
| 7 | 103.35 | | |
| 8 | 96.45 | | |
| 9 | 100.09 | | |
| 10 | 102.81 | | |
| Assay: 103.46% | | | |

Content uniformity testing was conducted on newly filled capsules of the blend made in Batch 054-002-14009A. The new capsules are identified as Batch L0136-42.

The original blend in Batch 054-002-14009A was formulated based on the protein content in Deb El Egg White Powder. The results of the protein content of Michael Foods Egg White Protein required the label claim to be adjusted down to 0.19 mg for this batch. The formulation for the original Batch 054-002-14009 A is shown in Table 32.

TABLE 32

Formulation for Batch 054-002-14009A (0.2*/019 mg** Protein)

| Item No. | Ingredient | Concentration | mg/Dose | Adjusted | Amount/ |
|---|---|---|---|---|---|
| 1 | EWP Pre-blend Lot 14008(*1.86% protein/**1.78% protein) | 7.17 | *10.75 (0.2 mg) | **10.75 (0.19 mg) | 107.55 |
| 2 | ProSolv SMCC 50 | 36.60 | 54.90 | 54.90 | 549.00 |
| 3 | ProSolv HD90 | 45.73 | 68.60 | 68.60 | 685.95 |
| 4 | Mannitol 200SD | 10.00 | 15.00 | 15.00 | 150.00 |
| 5 | Magnesium Stearate | 0.50 | 0.75 | 0.75 | 7.50 |
| | Total | 100 | 150 | 150 | 1500 |

*Based on egg white powder containing 85.71% protein.
**Based on egg white powder containing 81.85% protein.
(Blend was originally formulated based on EWP containing 85.71% protein and pre-blend concentration of 1.86% to give 0.2 mg protein per dose. The adjusted column in the tables reflects the actual protein content.)

The blend from the original batch was encapsulated at a higher fill weight to give a true 0.2 mg dosage form. These capsules are identified as Batch L0136-42. The adjusted formulation is shown in Table 33. The content uniformity results are shown in Tables 34-37.

TABLE 33

Formulation for Batch L0136-42 (0.2 mg Protein)

| | Ingredient | Concentration | mg/Dose | Adjusted |
|---|---|---|---|---|
| 1 | EWP Pre-blend Lot 14008(*1.86% protein/**1.78% protein) | 7.17 | *10.75 (0.19 mg) | 11.32 (0.2 mg) |
| 2 | ProSolv SMCC 50 | 36.60 | 54.90 | 57.81 |
| 3 | ProSolv HD90 | 45.73 | 68.60 | 72.24 |
| 4 | Mannitol 200SD | 10.00 | 15.00 | 15.80 |
| 5 | Magnesium Stearate | 0.50 | 0.75 | 0.79 |
| | Total | 100 | 150 | 158 |

*Based on egg white powder containing 85.71% protein.
**Based on egg white powder containing 81.85% protein.

TABLE 34

Content Uniformity, Batch 054-MFG-14009A (0.19 mg)

| Sample | % Recovery | | |
|---|---|---|---|
| 1 | 99.53 | Mean | 93.80 |
| 2 | 90.28 | Std Dev | 3.99 |
| 3 | 92.84 | % RSD | 4.25 |
| 4 | 93.34 | | |
| 5 | 99.82 | | |
| 6 | 90.78 | | |
| 7 | 91.55 | | |
| 8 | 88.07 | | |
| 9 | 94.39 | | |
| 10 | 97.43 | | |

Assay: 80.11%

TABLE 35

Content Uniformity, Batch L0136-42 (0.2 mg) (n = 10)

| Sample | % Recovery | | |
|---|---|---|---|
| 1 | 91.07 | Mean | 94.91 |
| 2 | 109.14 | Std Dev | 6.72 |
| 3 | 94.28 | % RSD | 7.08 |
| 4 | 98.05 | | |
| 5 | 98.09 | | |
| 6 | 89.79 | | |
| 7 | 96.82 | | |
| 8 | 83.84 | | |
| 9 | 91.35 | | |
| 10 | 96.71 | | |

Assay: 87.1%

TABLE 36

Content Uniformity, Batch L0136-42 (0.2 mg), (Repeated @ n = 20)

| Sample | % Recovery | | |
|---|---|---|---|
| 1 | 90.26 | Mean | 92.92 |
| 2 | 88.41 | Std Dev | 4.29 |
| 3 | 99.15 | % RSD | 4.62 |
| 4 | 99.31 | | |
| 5 | 89.05 | | |
| 6 | 88.40 | | |
| 7 | 103.92 | | |
| 8 | 92.65 | | |
| 9 | 89.86 | | |
| 10 | 94.57 | | |
| 11 | 91.55 | | |
| 12 | 94.01 | | |
| 13 | 88.03 | | |
| 14 | 93.01 | | |
| 15 | 93.47 | | |

TABLE 36-continued

Content Uniformity, Batch L0136-42 (0.2 mg), (Repeated @ n = 20)

| Sample | % Recovery |
|---|---|
| 16 | 94.26 |
| 17 | 91.22 |
| 18 | 95.06 |
| 19 | 95.06 |
| 20 | 87.12 |

Assay: 79.8%

TABLE 37

Content Uniformity, Batch L0136-42 (n = 30)

| Mean | 93.58 |
|---|---|
| Std Dev | 5.20 |
| % RSD | 5.55 |

Blend and content uniformity testing were conducted on Batches 054-002-14012C and 054-002-14013D by blending the formulations for 10-30 minutes in a blender and thieving a sample at each time points. The tests were conducted on batches having 10 mg and 100 mg dosage strengths, respectively. Both batches contained Michael Foods egg white protein powder from lot 4043W-3. The 10 mg batch was processed as a geometric dilution while the 100 mg batch was processed as a direct blend. Formulations for the batches are given in Tables 38 and 39. Blend and content uniformity data for the 100 mg batch are presented in Tables 40 and 41. Blend and content uniformity data for the 100 mg batch are presented in Tables 42 and 43.

TABLE 38

Formulation for Batch 054-MFG-14012C

| Item # | Ingredient | % w/w | mg/dose | g/batch |
|---|---|---|---|---|
| 1 | Egg White Powder (81.85% protein) | 2.57 | 12.2(10.0) | 38.55 |
| 2 | ProSolv SMCC 50 | 38.46 | 182.7 | 576.90 |
| 3 | ProSolv HD90 | 48.47 | 230.2 | 727.05 |
| 4 | Mannitol 200SD | 10.00 | 47.5 | 150.00 |
| 5 | Magnesium Stearate | 0.50 | 2.4 | 7.50 |
| | Total | 100 | 475 | 1500 |

*Based on egg white powder containing 81.85% protein.

TABLE 39

Formulation for Batch 054-MFG-14013D

| Item # | Ingredient | % w/w | mg/dose | g/batch |
|---|---|---|---|---|
| 1 | Egg White Powder (81.85% protein) | 25.73 | 122.2(100.0) | 385.95 |
| 2 | ProSolv SMCC 50 | 28.21 | 134.0 | 423.15 |
| 3 | ProSolv HD90 | 35.56 | 168.9 | 533.40 |
| 4 | Mannitol 200SD | 10.00 | 47.5 | 150.00 |
| 5 | Magnesium Stearate | 0.50 | 2.4 | 7.50 |
| | Total | 100 | 475 | 1500 |

*Based on egg white powder containing 81.85% protein.

TABLE 40

Blend Analysis, Batch 054-MFG-14012C (10.0 mg)

| Sample | % Recovery | | |
|---|---|---|---|
| 1 | 89.87 | Mean | 97.58 |
| 2 | 86.97 | Std Dev | 7.38 |
| 3 | 94.33 | % RSD | 7.56 |
| 4 | 97.77 | | |
| 5 | 112.61 | | |
| 6 | 98.96 | | |
| 7 | 94.69 | | |
| 8 | 94.76 | | |
| 9 | 101.17 | | |
| 10 | 104.68 | | |

Content Uniformity, Batch 054-MFG-14012C (10.0 mg)

TABLE 41

| Sample | % Recovery | | |
|---|---|---|---|
| 1 | 96.66 | Mean | 103.06 |
| 2 | 101.41 | Std Dev | 4.13 |
| 3 | 107.36 | % RSD | 4.01 |
| 4 | 108.23 | | |
| 5 | 104.89 | | |
| 6 | 103.00 | | |
| 7 | 108.40 | | |
| 8 | 100.01 | | |
| 9 | 98.24 | | |
| 10 | 102.43 | | |

Assay: 107.8%

TABLE 42

Blend Analysis, Batch 054-MFG-14013D (100.0 mg)

| Sample | % Recovery | | |
|---|---|---|---|
| 1 | 108.25 | Mean | 103.26 |
| 2 | 98.08 | Std Dev | 6.06 |
| 3 | 118.44 | % RSD | 5.87 |
| 4 | 100.06 | | |
| 5 | 100.86 | | |
| 6 | 98.62 | | |
| 7 | 100.79 | | |
| 8 | 103.84 | | |
| 9 | 102.38 | | |
| 10 | 101.27 | | |

TABLE 43

Content Uniformity, Batch 054-MFG-14013D

| Sample | % Recovery | | |
|---|---|---|---|
| 1 | 100.22 | Mean | 101.21 |
| 2 | 102.87 | Std Dev | 1.51 |
| 3 | 100.43 | % RSD | 1.50 |
| 4 | 103.37 | | |
| 5 | 99.98 | | |
| 6 | 101.47 | | |
| 7 | 98.33 | | |
| 8 | 101.69 | | |
| 9 | 101.24 | | |
| 10 | 102.45 | | |

Assay: 101.6

The process study was conducted to identify how blended the formulation was at different times of blending. The study used a 1.0 mg dosage strength as follows: Five sets of blend samples were thieved: 1. Following geometric dilution of egg white powder with SMCC50; 2. At 10 minutes of mix time with all diluents; 3. At 20 minutes of mix time with all diluents; 4. At 30 minutes of mix time with all diluents and lubricant, with thieved sample size of 1-3× unit dose; 5. At 30 minutes of mix time with all diluents and lubricant, with thieved sample size of 5-10× unit dose. The results of the study showed that the formulations were blended by 10 minutes time.

A swab recovery study was also conducted to look at efficiency of removal from the blender. Two samples were collected, one from each leg of the v-shell blender. The formulation of Batch 054-d02 14014B is shown in Table 44. Blend sampling recovery results are presented in Tables 45-49. The swab recovery results are presented in Table 50 and show that the recovery for this formulation was excellent. The measurement of protein recovered was a measurement of the total egg white protein. The results show that the blended formulation was recovered very efficiently from the blender.

TABLE 44

Formulation for 1 mg dose

| Item No. | Ingredient | Con-centration | mg/Dose | Amount/Batch |
|---|---|---|---|---|
| 1 | Egg White Protein (EWP) | 0.80 | 1.20(1.0) | 12.0 |
| 2 | Prosolv SMCC 50 | 41.60 | 62.4 | 624.0 |
| 3 | Prosolv HD90 | 47.10 | 70.65 | 706.5 |
| 4 | Mannitol 200 SD | 10.0 | 15.0 | 150.0 |
| 5 | Magnesium Stearate | 0.5 | 0.75 | 7.5 |
| | Total | 100 | 150 | 1500 |

*Formula based on egg white powder containing 83.3% protein.

TABLE 45

Blend Sampling, Step 8: Dilution with SMCC50

| Sample | % Recovery |
|---|---|
| 1 | 96.89 |
| 2 | 90.46 |
| 3 | 66.70 |
| 4 | 91.77 |
| 5 | 140.54 |
| 6 | 92.43 |
| Mean | 96.47 |
| Std Dev | 24.10 |
| % RSD | .24.98 |

TABLE 46

Blend Sampling, Step 10: At 10 Minutes Mix Time

| Sample | % Recovery |
|---|---|
| 1 | 91.76 |
| 2 | 92.09 |
| 3 | 92.86 |
| 4 | 90.52 |
| 5 | 90.28 |
| 6 | 89.20 |
| 7 | 90.88 |
| 8 | 93.65 |
| 9 | 91.73 |
| 10 | 91.40 |
| Mean | 91.44 |
| Std Dev. | 1.29 |
| % RSD | 1.41 |

TABLE 47

Blend Sampling, Step 12: At 20 Minutes Mix Time

| Sample | % Recovery |
|---|---|
| 1 | 93.17 |
| 2 | 87.15 |
| 3 | 91.38 |
| 4 | 88.17 |
| 5 | 95.89 |
| 6 | 90.92 |
| 7 | 93.78 |
| 8 | 89.33 |
| 9 | 87.61 |
| 10 | 88.41 |
| Mean | 90.58 |
| Std Dev | 2.95 |
| % RSD | 3.26 |

TABLE 48

Blend Sampling, Step 15: At 30 Minutes Mix Time, with Sample Size of 1-3X Unit Dose

| Sample | % Recovery |
|---|---|
| 1 | 84.35 |
| 2 | 83.56 |
| 3 | 83.40 |
| 4 | 82.93 |
| 5 | 83.31 |
| 6 | 87.34 |
| 7 | 103.47 |
| 8 | 82.34 |
| 9 | 84.87 |
| 10 | 81.90 |
| Ave | 85.75 |
| Std Dev. | 6.41 |
| % RSD | 7.48 |

TABLE 49

Blend Sampling, Step 15: At 30 Minutes Mix Time, with Sample Size of 5-10X Unit Dose

| Sample | % Recovery |
|---|---|
| 1 | 87.17 |
| 2 | 87.22 |
| 3 | 87.57 |
| 4 | 87.74 |
| 5 | 87.84 |
| 6 | 87.89 |
| 7 | 87.93 |
| 8 | 88.56 |
| 9 | 88.09 |
| 10 | 86.53 |
| Ave | 87.65 |
| Std Dev. | 0.56 |
| % RSD | 0.64 |

TABLE 50

Swab Recovery

Swab #1: Left Front  
0.069 mg protein recovered  
Swab #1: Right Back  
0.084 mg protein recovered  
Average protein recovered = 0.0765 mg  
Protein contained in blend = 9,996 mg  
Protein "lost" in blend process = 0.000765%

Example 8: High Dose Flow Recovery Analyses

High dose pouch (sachet) blends are typically used for doses of more than 100 mg because they no longer fit within a capsule (e.g., 100 mg, 200 mg, 300 mg, 400 mg, 500 mg, 600 mg, 700 mg, 800 mg, 900 mg and 1000 mg). High does pouch blends are often put in a pouch or sugar packet. The high dose pouch blends were analyzed for flowability and fill recovery. The flowability and recovery are studies to make sure that the capsule can be reproducibly filled by automated encapsulation machines, and to optimize the efficiency by which the capsule is easily emptied of powder by the subject. Initial formulations contained only egg white powder and talc. The flowability of these blends was very poor. The next set of prototypes contained egg white powder, PROSOLV® HD90, mannitol and magnesium stearate. The flowability of these blends was also very poor. Mannitol was removed from the formulation for the third set of prototypes. In the third set, two concentrations of talc were investigated to determine if improved flow could be obtained at levels low enough to avoid a negative impact on mouth feel. The flowability of these blends was markedly better than the earlier prototypes with a flow character of "passable".

The formulations for all prototypes are presented in Tables 51-53. Flow data for the prototypes are presented in Table 54. For comparison, Table 55 shows the Scale of Flowability. Recovery data are presented in Table 56.

TABLE 51

Formulations for Prototypes, Set A

| # | Ingredients | % w/w | g/batch |
|---|---|---|---|
| 1 | Egg powder | 97.5 | 34.12 |
|   | Talc | 2.5 | 0.88 |
|   | Total | 100 | 35 |
| 2 | Egg powder | 95.0 | 33.25 |
|   | Talc | 5.0 | 1.75 |
|   | Total | 100 | 35 |
| 3 | Egg powder | 92.5 | 32.37 |
|   | Talc | 7.5 | 2.63 |
|   | Total | 100 | 35 |
| 4 | Egg powder | 90.0 | 31.5 |
|   | Talc | 10.0 | 3.5 |
|   | Total | 100 | 35 |

TABLE 52

Formulations for Prototypes, Set B

| # | Ingredients | % w/w | g/batch |
|---|---|---|---|
| 5 | Egg powder | 58.34 | 87.51 |
|   | PROSOLV® | 36.16 | 54.24 |
|   | Mannitol | 5.0 | 7.5 |
|   | Magnesium Stearate | 0.5 | 0.75 |
|   | Total | 100 | 150 |
| 6 | Egg powder | 58.34 | 87.51 |
|   | PROSOLV® | 31.16 | 46.74 |
|   | Mannitol | 10.0 | 15.0 |
|   | Magnesium Stearate | 0.5 | 0.75 |
|   | Total | 100 | 150 |
| 7 | Egg powder | 58.34 | 87.51 |
|   | PROSOLV® | 26.16 | 39.24 |

TABLE 52-continued

Formulations for Prototypes, Set B

| # | Ingredients | % w/w | g/batch |
|---|---|---|---|
|  | Mannitol | 15.0 | 22.5 |
|  | Magnesium Stearate | 0.5 | 0.75 |
|  | Total | 100 | 150 |
| 8 | Egg powder | 58.34 | 87.51 |
|  | PROSOLV ® | 21.16 | 31.74 |
|  | Mannitol | 20.0 | 30.0 |
|  | Magnesium Stearate | 0.5 | 0.75 |
|  | Total | 100 | 150 |

TABLE 53

Formulations for Prototypes, Set C

| # | Ingredients | % w/w | g/batch |
|---|---|---|---|
| 9 | Egg powder | 50.0 | 75.0 |
|  | PROSOLV ® | 48.5 | 72.75 |
|  | Talc | 1.0 | 1.5 |
|  | Magnesium Stearate | 0.5 | 0.75 |
|  | Total | 100 | 150 |
| 10 | Egg powder | 50.0 | 75.0 |
|  | PROSOLV ® | 47.0 | 70.5 |
|  | Talc | 2.5 | 3.75 |
|  | Magnesium Stearate | 0.5 | 0.75 |
|  | Total | 100 | 150 |

TABLE 54

Flowability, Recovery & Observations

| Prototype Set | Sample Number | Carr's Index | Hausner Ratio |
|---|---|---|---|
| A | 1 | 40.3 | 1.67 |
|  | 2 | 36.7 | 1.58 |
|  | 3 | 35.4 | 1.55 |
|  | 4 | 35.7 | 1.56 |
| B | 5 | 38.0 | 1.61 |
|  | 6 | 38.9 | 1.64 |
|  | 7 | 41.0 | 1.70 |
|  | 8 | 39.0 | 1.64 |
| C | 9 | 21.0 | 1.27 |
|  | 10 | 22.1 | 1.28 |

TABLE 55

Scale of Flowability

| Carr's Index (%) | Flow Character | Hausner Ratio |
|---|---|---|
| ≤10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very, very poor | >1.60 |

TABLE 56

| Pouch Recovery | | | | | |
|---|---|---|---|---|---|
| Set A | | Set B | | Set C | |
| Prototype | Recovery | Prototype | Recovery | Prototype | Recovery |
| 1 | 94.8% | 5 | 98.3% | 9 | 97.5% |
| 2 | 87.9% | 6 | 97.9% | 10 | 97.8% |
| 3 | 93.7% | 7 | 97.8% |  |  |
| 4 | 95.4% | 8 | 98.1% |  |  |

As a result of the studies, a talc formulation was determined to be more useful for flowability for high dose blends. In one embodiment, a 1% talc formulation is used in the high dose pouches. Approximately 1.2 g fill weight is used for the 500 mg dosage strength and 2.4 g for the 1000 mg. The exact weights are determined based on the protein content of the egg white powder used in each batch.

Example 9: Six Month Stability Study

The stability of egg white protein capsules was analyzed for 6 months for 0.2 mg, 1.0 mg, 10 mg, and 100 mg capsules. The exemplary formulations in Tables 57-60 were used to identify general stability of the egg white protein formulations described herein. All blends for this study were processed as GMP demonstration batches using Michael Foods egg white powder (lot 4043W-3). The capsules used for this study were produced in the following batches: D14089, 0.2 mg egg white protein capsules; D14084, 1.0 mg egg white protein capsules; D14072, 10.0 mg egg white protein capsules; and D14070, 100.0 mg egg white protein capsules.

The stability protocol was as follows: Samples were stored at 25° C./60% RH and 30° C./65% RH. The capsules were packaged and stored in HDPE bottles with desiccant and CRC heat sealed closures. The count per bottle was 10 for 0.2 mg in a 30 cc bottle, 200 for 1.0 mg in a 150 cc bottle, 200 for 10.0 mg in a 500 cc bottle, and 200 for 10 mg in a 500 cc bottle. The number of capsules tested for each test was as follows: Appearance and Olfactory: n=10, LOD: 2 g (14 capsules for 0.2, 1.0 mg/5 capsules for 10, 100 mg); Potency of Ovomucoid (ELISA): n=10; Assay (protein content by HPLC): n=10, Deliverable Mass: n=10, Content Uniformity: n=20 (performed only at T=0), and Micro: 15 g (100 of 0.2 and 1.0/32 of 10.0 and 100.0). The samples were tested for T=0 data when the batches were produced. The samples were pulled from chambers at 1M, 2M, 3M, and 6M (and 11M for Example 10). Each sample was tested for appearance (shell and contents), Olfactory, LOD, potency of ovomucoid, assay and deliverable mass. Content uniformity testing was performed at T=0 and microbial limits testing was performed at and T=12M (see examples 1-8 for each test).

Formulations for the batches are given in Tables 57 through 60. Appearance and Odor are summarized in Tables 61 through 64. Loss on Drying results are presented in Table 65. Potency of Ovomucoid (ELISA) is presented in Table 66. Assay results are presented in Table 67. Content Uniformity results are presented in Table 68. Blend Uniformity results are presented in Table 69. Deliverable Mass data are presented in Table 70.

TABLE 57

Formulation for EOIT; Batch D14089 (0.2 mg)

| Item # | Ingredient | % w/w | mg/dose | g/batch |
|---|---|---|---|---|
| 1 | Egg White Powder | 0.173(0.160) | 0.26(0.24) | 8.70 |
| 2 | ProSolv SMCC 50 | 42.13 | 63.2 | 2106.5 |
| 3 | ProSolv HD90 | 47.20 | 70.8 | 2360.0 |
| 4 | Mannitol 200SD | 10.00 | 15.0 | 500.00 |
| 5 | Magnesium Stearate | 0.50 | 0.75 | 25.0 |
|   | Subtotal | 100 | 150 | 5000 |
|   | White Opaque VCaps Plus, 3 |  | 47 |  |
|   | Total |  | 197 |  |

*Based on egg white powder containing 81.85% protein. Includes a 5% overage of egg white protein.

TABLE 58

Formulation for EOIT; Batch D14084 (1.0 mg)

| Item# | Ingredient | % w/w | mg/dose | g/batch |
|---|---|---|---|---|
| 1 | Egg White Powder | 0.84(0.69) | 1.26(1.03) | 42.0 |
| 2 | ProSolv SMCC 50 | 41.56 | 62.34 | 2078.0 |
| 3 | ProSolv HD90 | 47.10 | 70.65 | 2355.0 |
| 4 | Mannitol 200SD | 10.00 | 15.0 | 500.0 |
| 5 | Magnesium Stearate | 0.50 | 0.75 | 25.0 |
|   | Subtotal | 100 | 150 | 5000 |
|   | Natural Transparent VCaps Plus, 3 |  | 47 |  |
|   | Total |  | 197 |  |

*Based on egg white powder containing 81.85% protein. Includes a 3% overage of egg white protein.

TABLE 59

Formulation for EOIT; Batch D14072 (10.0 mg)

| Item # | Ingredient | % w/w | mg/dose | g/batch |
|---|---|---|---|---|
| 1 | Egg White Powder | 2.57 | 12.2(10.0) | 128.5(105.2) |
| 2 | ProSolv SMCC 50 | 38.46 | 182.7 | 1923 |
| 3 | ProSolv HD90 | 48.47 | 230.2 | 2423.5 |
| 4 | Mannitol 200SD | 10.00 | 47.5 | 500.00 |
| 5 | Magnesium Stearate | 0.50 | 2.4 | 25.0 |
|   | Subtotal | 100 | 475 | 5000 |
|   | Blue Opaque VCaps Plus, 00 |  | 120 |  |
|   | Total |  | 595 |  |

*Based on egg white powder containing 81.85% protein.

TABLE 60

Formulation for EOIT; Batch D14070 (100.0)

| Item # | Ingredient | % w/w | mg/dose | g/batch |
|---|---|---|---|---|
| 1 | Egg White Powder | 25.73 | 122.2(100.0) | 1286.5(1000.0) |
| 2 | ProSolv SMCC 50 | 28.21 | 134.0 | 1410.5 |
| 3 | ProSolv HD90 | 35.56 | 168.9 | 1778.0 |
| 4 | Mannitol 200SD | 10.00 | 47.5 | 500.0 |
| 5 | Magnesium Stearate | 0.50 | 2.4 | 25.0 |
|   | Subtotal | 100 | 475 | 5000 |
|   | Sw OrangeVCaps Plus Shell, 00 |  | 120 |  |
|   | Total |  | 595 |  |

*Based on egg white powder containing 81.85% protein.

TABLE 61

Physical Characteristics of Batch 14089 (0.2 mg)

| Time point | Appearance | Odor |
|---|---|---|
| T = 0 | white capsule containing white, free-flowing fine powder with few clumps | no distinct odor |
| T = 1 M | white capsule containing white, free-flowing fine powder with few clumps | no distinct odor |
| T = 2 M | white capsule containing white, free-flowing fine powder with few clumps | no distinct odor |
| T = 3 M | white capsule containing white, five-flowing fine powder with few clumps | no distinct odor |
| T = 4.5 M | white capsule containing white, free-flowing fine powder with few clumps | no distinct odor |
| T = 6 M | white capsule containing white, free-flowing fine powder with few clumps | no distinct odor |

TABLE 62

Physical Characteristics of Batch 14084 (1.0 mg)

| Time point | Appearance | Odor |
|---|---|---|
| T = 0 | clear capsule containing white, free-flowing fine powder with few clumps | no distinct odor |
| T = 1 M | clear capsule containing white, free-flowing fine powder with few clumps | no distinct odor |
| T = 2 M | clear capsule containing white, free-flowing fine powder with few clumps | no distinct odor |
| T = 3 M | clear capsule containing white, free-flowing fine powder with few clumps | no distinct odor |
| T = 4.5 M | clear capsule containing white, free-flowing fine powder with few clumps | no distinct odor |
| T = 6 M | clear capsule containing white, free-flowing fine powder with few clumps | no distinct odor |

TABLE 63

Physical Characteristics of Batch 14072 (10.0 mg)

| Time point | Appearance | Odor |
|---|---|---|
| T = 0 | dark blue capsule; white free-flowing fine powder with few clumps | faint acetic acid odor |
| T = 1 M | dark blue capsule; white free-flowing fine powder with few clumps | faint acetic acid odor |
| T = 2 M | dark blue capsule; white free-flowing fine powder with few clumps | faint acetic acid odor |
| T = 3 M | dark blue capsule; white free-flowing fine powder with few clumps | faint acetic acid odor |
| T = 4.5 M | dark blue capsule; white free-flowing fine powder with few clumps | faint acetic acid odor |
| T = 6 M | dark blue capsule; white free-flowing fine powder with few clumps | faint acetic acid odor |

TABLE 64

Physical Characteristics of Batch 14070 (100.0 mg)

| Time point | Appearance | Odor |
|---|---|---|
| T = 0 | Burnt orange capsule with gray bar on cap, black bar on body; off-white, free-flowing fine powder with few clumps | faint acetic acid odor |
| T = 1 M | Burnt orange capsule with gray bar on cap, black bar on body; off-white, free-flowing fine powder with few clumps | faint acetic acid odor |
| T = 2 M | Burnt orange capsule with gray bar on cap, black bar on body; off-white, free-flowing fine powder with few clumps | faint acetic acid odor |

TABLE 64-continued

Physical Characteristics of Batch 14070 (100.0 mg)

| Time point | Appearance | Odor |
|---|---|---|
| T = 3 M | Burnt orange capsule with gray bar on cap, black bar on body; off-white, free-flowing fine powder with few clumps | faint acetic acid odor |
| T = 4.5 M | Burnt orange capsule with gray bar on cap, black bar on body; off-white, free-flowing fine powder with few clumps | faint acetic acid odor |
| T = 6 M | Burnt orange capsule with gray bar on cap, black bar on body; off-white, free-flowing fine powder with few clumps | faint acetic acid odor |

TABLE 65

Loss on Drying

| Time | Batch D14089 (0.2 mg) T = 0, 2.7% | | Batch D14084 (1 mg) T = 0, 3.9% | | Batch D14072 (10 mg) T = 0, 4.4% | | Batch D14070 (100 mg) T = 0, 5.2% | |
|---|---|---|---|---|---|---|---|---|
| Condition | 25/60 | 30/65 | 25/60 | 30/65 | 25/60 | 30/65 | 25/60 | 30/65 |
| T = 1 M | 3.7% | 3.5% | 5.1% | 4.2% | 5.3% | 4.7% | 5.8% | 5.4% |
| T = 2 M | 3.5% | 3.1% | 4.2% | 4.3% | 4.6% | 4.5% | 5.5% | 5.1% |
| T = 3 M | 3.1% | 3.3% | 4.3% | 4.3% | 4.5% | 4.5% | 5.5% | 5.2% |
| T = 4.5 M | 3.1% | 3.5% | 4.2% | 4.4% | 4.5% | 4.5% | 5.3% | 5.3% |
| T = 6 M | 4.7% | 4.1% | 5.1% | 4.9% | 5.0% | 4.7% | 5.8% | 5.6% |

TABLE 66

Potency of Ovomucoid (ELISA)

| Time | Batch D14089 (0.2 mg) | | Batch D14084 (1 mg) | | Batch D14072 (10 mg) | | Batch D14070 (100 mg) | |
|---|---|---|---|---|---|---|---|---|
| Condition | 25/60 | 30/65 | 25/60 | 30/65 | 25/60 | 30/65 | 25/60 | 30/65 |
| T = 0 | Data not available at T = 0; Method Development was still in progress. | | | | | | | |
| T = 1 M | 91.1 | 85.4 | 89.3 | 73.8 | 96.2 | 107.2 | 89.9 | 115.2 |
| T = 2 M | 41.3 | 42.2 | 49.9 | 51.5 | 81.8 | 96.3 | 100.1 | 106.1 |
| T = 3 M | 65.0 | 69.2 | 67.3 | 93.9 | 71.8 | 91.2 | 94.5 | 85.4 |
| T = 4.5 M | 69.3 | 76.6 | 88.9 | 81.3 | 90.2 | 94.8 | 90.3 | 96.8 |
| T = 6 M | 99* | 83* | 90** | 93** | 86** | 84** | 91** | 73** |
|  | 75** | 63** |  |  |  |  |  |  |

*With place spiked standard
**With regular standard

TABLE 68

Content Uniformity (Run only at T = 0)

| | Batch D14089 (0.2 mg) | Batch D14084 (1 mg) | Batch D14072 (10 mg) | Batch D14070 (100 mg) |
|---|---|---|---|---|
| Range | 88-102 | 86-112 | 99-106 | 104-118 |
| Ave | 93.39 | 101.74 | 102.25 | 110.01 |
| % RSD | 5.07 | 6.73 | 1.91 | 3.70 |

TABLE 69

Physical Characteristics of Batch 14089 (0.2 mg)

| | Batch D14089 (0.2 mg) | Batch D14084 (1 mg) | Batch D14072 (10 mg) | Batch D14070 (100 mg) |
|---|---|---|---|---|
| Range | 76-84 | 94-100 | 98-105 | 105-117 |
| Ave | 79.21 | 94.64 | 101.39 | 108.55 |
| % RSD | 3.68 | 2.29 | 2.17 | 3.31 |

TABLE 70

Physical Characteristics of Batch 14089 (0.2 mg)

| Time | Batch D14089 (0.2 mg) | | Batch D14084 (1 mg) | | Batch D14072 (10 mg) | | Batch D14070 (100 mg) | |
|---|---|---|---|---|---|---|---|---|
| Condition | 25/60 | 30/65 | 25/60 | 30/65 | 25/60 | 30/65 | 25/60 | 30/65 |
| T = 0 Ave | 100.5 | | 100.2 | | 100.1 | | 100.1 | |
| T = 0% RSD | 0.4 | | 0.3 | | 0.2 | | 0.1 | |
| T = 1 M Ave | 100 | 100.2 | 99.8 | 99.9 | 100.1 | 99.9 | 100.0 | 99.9 |
| T = 1 M % RSD | 0.6 | 0.3 | 0.4 | 0.3 | 0.1 | 0.1 | 0.1 | 0.1 |
| T = 2 M Ave | 100.2 | 100.5 | 100.1 | 99.1 | 100.1 | 100.0 | 100.0 | 100.0 |
| T = 2 M % RSD | 0.2 | 0.2 | 0.3 | 2.4 | 0.1 | 0.1 | 0.1 | 0.1 |
| T = 3 M Ave | 100.0 | 100.0 | 99.9 | 99.5 | 100.1 | 100.1 | 100.1 | 100.0 |

TABLE 70-continued

Physical Characteristics of Batch 14089 (0.2 mg)

| Time | Batch D14089 (0.2 mg) | | Batch D14084 (1 mg) | | Batch D14072 (10 mg) | | Batch D14070 (100 mg) | |
|---|---|---|---|---|---|---|---|---|
| Condition | 25/60 | 30/65 | 25/60 | 30/65 | 25/60 | 30/65 | 25/60 | 30/65 |
| T = 3 M % RSD | 3.4 | 0.4 | 0.5 | 0.5 | 0.2 | 0.1 | 0.1 | 0.0 |
| T = 4.5 M Ave | 100.0 | 100.1 | 99.9 | 100.0 | 100.0 | 100.0 | 100.0 | 99.9 |
| T = 4.5 M | 0.4 | 0.3 | 0.3 | 0.4 | 0.1 | 0.1 | 0.1 | 0.1 |
| T = 6 M Ave | 98.7 | 99.1 | 99.2 | 99.2 | 99.6 | 99.8 | 99.5 | 99.6 |
| T = 6 M % RSD | 0.8 | 0.6 | 0.6 | 0.4 | 0.3 | 0.1 | 0.1 | 0.3 |

The tests above were used to establish the stability of egg white powder capsules for the exemplary formulations. The loss on Drying results in Table 65, for 0.2, 1, 10, and 100 mg, show that the loss on drying for the formulations varied a small amount, but there was no significant difference between 1 month, 2 months, 3 months, 4.5 months and 6 months.

Ovomucoid was used as an exemplary egg protein to test the specific potency of the protein over time. The potency of Ovomucoid (ELISA) presented in Table 66 again showed some variation, but no consistent loss with time up to 6 months. The HPLC assay results presented in Table 67 show no significant loss in egg proteins over the 6 months. Content Uniformity (Table 68), blend Uniformity (Table 69), and deliverable Mass data (Table 70) confirmed these results.

The results at 6 months show that at both temperatures in this formulation the protein moisture content and physical characteristics are unchanged. Thus, the tested blends were stable for 6 months and, therefore, pharmaceutical preparations of the formulations can be used reliably for at least 6 months.

Example 10: Eleven Month Stability Study

The stability of egg white protein capsules was analyzed for 11 months for 0.2 mg, 1.0 mg, 10 mg, and 100 mg capsules. The stability protocol in Example 9 was used. All blends for this study were processed as GMP demonstration batches using Michael Foods egg white protein powder (lot 4043W-3). The capsules used for this study were produced in the following batches: D14089, 0.2 mg egg white protein capsules; D14084, 1.0 mg egg white protein capsules; D14072, 10.0 mg egg white protein capsules; and D14070, 100.0 mg egg white protein capsules.

TABLE 71

Physical Characteristics of Batch 14089 (0.2 mg)

| Time point | Appearance | Odor |
|---|---|---|
| T = 0 | white capsule containing white, free- flowing fine powder with few clumps | no distinct odor |
| T = 1 M | white capsule containing white, free- flowing fine powder with few clumps | no distinct odor |
| T = 2 M | white capsule containing white, free- flowing fine powder with few clumps | no distinct odor |
| T = 3 M | white capsule containing white, free- flowing fine powder with few clumps | no distinct odor |
| T = 4.5 M | white capsule containing white, free- flowing fine powder with few clumps | no distinct odor |
| T = 6 M | white capsule containing white, free- flowing fine powder with few clumps | no distinct odor |
| T = 11 M | white capsule containing white, free- flowing fine powder with few clumps | no distinct odor |

TABLE 72

Physical Characteristics of Batch 14084 (1.0 mg)

| Time point | Appearance | Odor |
|---|---|---|
| T = 0 | clear capsule containing white, free- flowing fine powder with few clumps | no distinct odor |
| T = 1 M | clear capsule containing white, free- flowing fine powder with few clumps | no distinct odor |
| T = 2 M | clear capsule containing white, free- flowing fine powder with few clumps | no distinct odor |
| T = 3 M | clear capsule containing white, free- flowing fine powder with few clumps | no distinct odor |
| T = 4.5 M | clear capsule containing white, free- flowing fine powder with few clumps | no distinct odor |
| T = 6 M | clear capsule containing white, free- flowing fine powder with few clumps | no distinct odor |
| T = 11 M | clear capsule containing white, free- flowing fine powder with few clumps | no distinct odor |

TABLE 73

Physical Characteristics of Batch 14072 (10.0 mg)

| Time point | Appearance | Odor |
|---|---|---|
| T = 0 | dark blue capsule; white free-flowing fine powder with few clumps | faint acetic acid odor |
| T = 1 M | dark blue capsule; white free-flowing fine powder with few clumps | faint acetic acid odor |
| T = 2 M | dark blue capsule; white free-flowing fine powder with few clumps | faint acetic acid odor |
| T = 3 M | dark blue capsule; white free-flowing fine powder with few clumps | faint acetic acid odor |
| T = 4.5 M | dark blue capsule; white free-flowing fine powder with few clumps | faint acetic acid odor |
| T = 6 M | dark blue capsule; white free-flowing fine powder with few clumps | faint acetic acid odor |
| T = 11 M (25° C. 60% RH) | dark blue capsule; white free-flowing fine powder | faint acetic acid odor |
| T = 11 M (30° C. 60% RH) | dark blue capsule; white free-flowing fine powder | faint acetic acid odor |

TABLE 74

Physical Characteristics of Batch 14070 (100.0 mg)

| Time point | Appearance | Odor |
|---|---|---|
| T = 0 | Burnt orange capsule with gray bar on cap, black bar on body; off-white, free- flowing fine powder with few clumps | faint acetic acid odor |
| T = 1 M | Burnt orange capsule with gray bar on cap, black bar on body; off-white, free- flowing fine powder with few clumps | faint acetic acid odor |
| T = 2 M | Burnt orange capsule with gray bar on cap, black bar on body; off-white, free- flowing fine powder with few clumps | faint acetic acid odor |
| T = 3 M | Burnt orange capsule with gray bar on cap, black bar on body; off-white, free- flowing fine powder with few clumps | faint acetic acid odor |
| T = 4.5 M | Burnt orange capsule with gray bar on cap, black bar on body; off-white, free- flowing fine powder with few clumps | faint acetic acid odor |
| T = 6 M | Burnt orange capsule with gray bar on cap, black bar on body; off-white, free- flowing fine powder with few clumps | faint acetic acid odor |
| T = 11 M | Burnt orange capsule with gray bar on cap, black bar on body; off-white, free- flowing fine powder | faint acetic acid odor |

TABLE 75

Loss on Drying

| Time | Batch D14089 (0.2 mg) T = 0, 2.7% | | Batch D14084 (1 mg) T = 0, 3.9% | | Batch D14072 (10 mg) T = 0, 4.4% | | Batch D14070 (100 mg) T = 0, 5.2% | |
|---|---|---|---|---|---|---|---|---|
| Condition | 25/60 | 30/65 | 25/60 | 30/65 | 25/60 | 30/65 | 25/60 | 30/65 |
| T = 1 M | 3.7% | 3.5% | 5.1% | 4.2% | 5.3% | 4.7% | 5.8% | 5.4% |
| T = 2 M | 3.5% | 3.1% | 4.2% | 4.3% | 4.6% | 4.5% | 5.5% | 5.1% |
| T = 3 M | 3.1% | 3.3% | 4.3% | 4.3% | 4.5% | 4.5% | 5.5% | 5.2% |
| T = 4.5 M | 3.1% | 3.5% | 4.2% | 4.4% | 4.5% | 4.5% | 5.3% | 5.3% |
| T = 6 M | 4.7% | 4.1% | 5.1% | 4.9% | 5.0% | 4.7% | 5.8% | 5.6% |
| T = 11 M | 3.7% | 4.3% | 4.5% | 5.0% | 4.6% | 4.7% | 5.5% | 5.6% |

TABLE 76

Deliverable Mass (Reported as Percent)

| Time | | Batch D14089 (0.2 mg) | | Batch D14084 (1 mg) | | Batch D14072 (10 mg) | | Batch D14070 (100 mg) | |
|---|---|---|---|---|---|---|---|---|---|
| Condition | | 25/60 | 30/65 | 25/60 | 30/65 | 25/60 | 30/65 | 25/60 | 30/65 |
| T = 0 | Ave | 100.5 | | 100.2 | | 100.1 | | 100.1 | |
|  | % RSD | 0.4 | | 0.3 | | 0.2 | | 0.1 | |
| T = 1 M | Ave | 100 | 100.2 | 99.8 | 99.9 | 100.1 | 99.9 | 100.0 | 99.9 |
|  | % RSD | 0.6 | 0.3 | 0.4 | 0.3 | 0.1 | 0.1 | 0.1 | 0.1 |
| T = 2 M | Ave | 100.2 | 100.5 | 100.1 | 99.1 | 100.1 | 100.0 | 100.0 | 100.0 |
|  | % RSD | 0.2 | 0.2 | 0.3 | 2.4 | 0.1 | 0.1 | 0.1 | 0.1 |
| T = 3 M | Ave | 100.0 | 100.0 | 99.9 | 99.5 | 100.1 | 100.1 | 100.1 | 100.0 |
|  | % RSD | 3.4 | 0.4 | 0.5 | 0.5 | 0.2 | 0.1 | 0.1 | 0.0 |
| T = 4.5 M | Ave | 100.0 | 100.1 | 99.9 | 100.0 | 100.0 | 100.0 | 100.0 | 99.9 |
|  | % RSD | 0.4 | 0.3 | 0.3 | 0.4 | 0.1 | 0.1 | 0.1 | 0.1 |
| T = 6 M | Ave | 98.7 | 99.1 | 99.2 | 99.2 | 99.6 | 99.8 | 99.5 | 99.6 |
|  | % RSD | 0.8 | 0.6 | 0.6 | 0.4 | 0.3 | 0.1 | 0.1 | 0.3 |
| T = 11 M | Ave | 100.2 | 100.1 | 100.0 | 99.8 | 100.0 | 100.0 | 99.9 | 99.9 |
|  | % RSD | 0.2 | 0.5 | 0.2 | 0.8 | 0.1 | 0.1 | 0.1 | 0.1 |

Formulations for the batches are given in Tables 57 through 60 above. Appearance and Odor are summarized in Tables 71-74. Loss on Drying results are presented in Table 75. Deliverable Mass results are provided in Table 76. Tables 77 and 78 provide data about the egg protein after 11 months, showing that at 11 months the HPLC assay results (Table 77) are not significantly different from those at 1 month, 2 months, etc.

TABLE 77

Assay (HPLC)

| Time | Batch D14089 (0.2 mg) | | Batch D14084 (1 mg) | | Batch D14072 (10 mg) | | Batch D14070 (100 mg) | |
|---|---|---|---|---|---|---|---|---|
| Condition | 25/60 | 30/65 | 25/60 | 30/65 | 25/60 | 30/65 | 25/60 | 30/65 |
| T = 0 | 95.5 | | 100.0 | | 102.4 | | 110.0 | |
| T = 1 M | 113.5 | 113.8 | 97.5 | 96.6 | 97.4 | 96.3 | 106.3 | 107.2 |
| T = 2 M | 87.9 | 85.9 | 96.6 | 94.9 | 97.9 | 96.2 | 104.3 | 101.8 |
| T = 3 M | 86.0 | 79.9 | 96.7 | 92.5 | 100.5 | 98.0 | 102.8 | 105.0 |
| T = 4.5 M | 83.5 | 78.8 | 88.3 | 89.3 | 93.3 | 89.3 | 97.5 | 99.6 |
| T = 6 M | 87.7 | 80.1 | 91.1 | 85.8 | 94.9 | 89.8 | 102.7 | 100.8 |
| T = 11 M | 82.2 | 71.6 | 90.3 | 80.4 | 92.0 | 87.3 | 118.2 | 117.9 |

TABLE 78

Potency of Ovomucoid (ELISA)

| Time | Batch D14089 (0.2 mg) | | Batch D14084 (1 mg) | | Batch D14072 (10 mg) | | Batch D14070 (100 mg) | |
|---|---|---|---|---|---|---|---|---|
| Condition | 25/60 | 30/65 | 25/60 | 30/65 | 25/60 | 30/65 | 25/60 | 30/65 |
| T = 0 | Data not available at T = 0; Method Development was still in progress. | | | | | | | |
| T = 1 M | 91.1 | 85.4 | 89.3 | 73.8 | 96.2 | 107.2 | 89.9 | 115.2 |
| T = 2 M | 41.3 | 42.2 | 49.9 | 51.5 | 81.8 | 96.3 | 100.1 | 106.1 |
| T = 3 M | 65.0 | 69.2 | 67.3 | 93.9 | 71.8 | 91.2 | 94.5 | 85.4 |
| T = 4.5 M | 69.3 | 76.6 | 88.9 | 81.3 | 90.2 | 94.8 | 90.3 | 96.8 |
| T = 6 M | 99*  75** | 83*  63** | 90** | 93** | 86** | 84** | 91** | 73** |
| T = 11 M | 100*  84** | 105**  85** | 111*  93** | 121*  102** | 76** | 76** | 78** | 85** |

*With place spiked standard
**With regular standard

The results of the 11 month stability study show that the dosage, moisture content, total protein and ovomucoid potency stays the same within acceptable variation. Therefore, the formulation provides an environment that allows the moisture content to stay stable. However, Table 78 shows that there was some loss in potency at high temperature, suggesting the formulations should be kept no higher than at room temperature for best stability.

Example 11: Manufacturing Protocol

The following materials were screened through a 20-mesh screen and added to a 16 quart V-blender: Dried Egg White protein and ProSolve SMCC50 (Silicified. Microcrystalline Cellulose, NF). The material was blended for 5 minutes. the contents of the 16 quart V-shell were discharged and screened through a 60-mesh screen. The screened material was returned to the 16 quart V-shell. Rinse the empty bag with ProSolv® SMCC50 and screen the rinse material through a 60 mesh, return the screened material to the 16 quart V-shell and blend for 10 minutes. Repeat.

Screen the following materials in order through a 20 mesh screen and add to the 16 quart V-blender: ProSolv® SMCC50. Blend for 15 minutes. Screen the following materials in order through a 20-mesh screen and add to the 16 quart V-blender: ProSolv® SMCC HD90 and Mannitol, NF (Pearlitol® 200SD). Blend the combined material for 15 minutes. Pass Magnesium Stearate, NF (Hyqual® Vegetable Source) through a 40 mesh screen and add to the blend. Blend for 10 minutes. Discharge the combined blend into an appropriately sized container lined with 2 polyethylene bags. Analyze the protein content and uniformity of the blend and package appropriately into a capsule or pouch.

VII. Conclusion

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

All publications, patents, and patent applications mentioned in this specification are herein incorporated by reference to the same extent as if each individual publication, patent, or patent application was specifically and individually indicated to be incorporated by reference.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while process steps, formulation components or functions are presented in a given order, alternative embodiments may include these in a different order, or substantially concurrently. The teachings of the disclosure provided herein can be applied to other compositions, not only the compositions described herein. The various embodiments described herein can be combined to provide further embodiments.

Specific elements of any of the foregoing embodiments can be combined or substituted for elements in other embodiments. Furthermore, while aspects, associated with certain embodiments of the disclosure have been described in the context of these embodiments, other embodiments may also exhibit such aspects, and not all embodiments need necessarily exhibit such aspects to fall within the scope of the disclosure. Accordingly, the disclosure is not limited, except as by the appended claims.

What is claimed is:

1. A method of manufacturing a packaged pharmaceutical formulation for the treatment of egg allergy in a subject, comprising: a) determining the concentrations of ovomucoid, ovalbumin, and lysozyme proteins in a composition of egg white protein by one or more analytical methods; b) comparing the concentrations of the proteins to the concentrations of a reference standard; c) selecting a composition for treatment of egg allergy in a subject; and d) packaging the selected composition in a container, wherein the selected composition contains at least the concentrations of ovomucoid, ovalbumin, and lysozyme protein as the reference standard.

2. The method of claim 1, wherein the analytic method is size exclusion chromatography.

3. The method of claim 2, wherein the size exclusion chromatography is performed using high-performance liquid chromatography (HPLC).

4. The method of claim 1, wherein the one or more analytical methods comprises an enzyme-linked immunosorbent assay (ELISA).

5. The method of claim 1, wherein the one or more analytical methods comprises a high-performance liquid chromatography (HPLC) assay.

6. The method of claim 5, wherein the one or more analytical methods further comprises an enzyme-linked immunosorbent assay (ELISA).

7. The method of claim 1, comprising determining a concentration of total protein in the composition of egg white protein.

8. The method of claim 1, wherein the concentrations of ovomucoid, ovalbumin, and lysozyme proteins in the composition of egg white protein are determined after a storage period.

9. The method of claim 8, wherein the storage period is 3 or more months.

10. The method of claim 1, wherein the concentration of ovomucoid in the selected composition is about 0.16 mg to about 0.24 mg ovomucoid for 1.0 mg of total egg protein.

11. The method of claim 1, wherein the concentration of ovalbumin in the selected composition is about 0.46 mg to about 0.54 mg ovalbumin for 1.0 mg of total egg protein.

12. The method of claim 1, wherein the concentration of lysozyme in the selected composition is about 0.01 mg to about 0.09 mg lysozyme for 1.0 mg of total egg protein.

13. The method of claim 1, wherein the container is a capsule.

14. The method of claim 1, wherein the container is a sachet.

15. The method of claim 1, wherein the packaging the selected composition comprises dosing the selected composition at a target unit weight of egg white protein.

16. The method of claim 15, wherein the target unit weight of egg white protein is between about 0.2 mg and about 1000 mg egg white protein.

17. The method of claim 16, wherein the target unit weight of egg white protein is about 0.2 mg egg white protein.

18. The method of claim 16, wherein the target unit weight of egg white protein is about 1.0 mg egg white protein.

19. The method of claim 16, wherein the target unit weight of egg white protein is about 10 mg egg white protein.

20. The method of claim 16, wherein the target unit weight of egg white protein is about 100 mg egg white protein.

21. The method of claim 16, wherein the target unit weight of egg white protein is about 300 mg egg white protein.

\* \* \* \* \*